US012365921B2

(12) United States Patent
Sato et al.

(10) Patent No.: US 12,365,921 B2
(45) Date of Patent: Jul. 22, 2025

(54) LIPID NANOPARTICLE

(71) Applicant: NATIONAL UNIVERSITY CORPORATION HOKKAIDO UNIVERSITY, Sapporo (JP)

(72) Inventors: Yusuke Sato, Sapporo (JP); Hideyoshi Harashima, Sapporo (JP); Manabu Tokeshi, Sapporo (JP); Masatoshi Maeki, Sapporo (JP)

(73) Assignee: National University Corporation Hokkaido University, Sapporo (JP)

( * ) Notice: Subject to any disclaimer, the term of this patent is extended or adjusted under 35 U.S.C. 154(b) by 687 days.

(21) Appl. No.: 17/595,156

(22) PCT Filed: May 27, 2020

(86) PCT No.: PCT/JP2020/020895
§ 371 (c)(1),
(2) Date: Nov. 10, 2021

(87) PCT Pub. No.: WO2020/241679
PCT Pub. Date: Dec. 3, 2020

(65) Prior Publication Data
US 2022/0213509 A1 Jul. 7, 2022

(30) Foreign Application Priority Data
May 30, 2019 (JP) .................... 2019-101203

(51) Int. Cl.
*C12N 15/88* (2006.01)
*B82Y 5/00* (2011.01)
*B82Y 40/00* (2011.01)

(52) U.S. Cl.
CPC ............... *C12N 15/88* (2013.01); *B82Y 5/00* (2013.01); *B82Y 40/00* (2013.01)

(58) Field of Classification Search
CPC ............ C12N 15/88; B82Y 5/00; B82Y 40/00
See application file for complete search history.

(56) References Cited

U.S. PATENT DOCUMENTS

| 2020/0129431 A1 | 4/2020 | Harashima et al. |
| 2021/0129103 A1 | 5/2021 | Tokeshi et al. |

FOREIGN PATENT DOCUMENTS

| CN | 106754912 A * | 5/2017 | |
| EP | 3147277 A1 * | 3/2017 | ......... A61K 31/7105 |
| WO | WO-2017053879 A1 * | 3/2017 | ......... A61K 31/7105 |
| WO | WO-2018081728 A1 * | 5/2018 | ......... C07K 14/4702 |
| WO | 2018107028 A1 | 6/2018 | |
| WO | 2018190423 A1 | 10/2018 | |
| WO | 2018213708 A1 | 11/2018 | |
| WO | 2018230710 A1 | 12/2018 | |

OTHER PUBLICATIONS

Machine translation of CN-10675491-A (Year: 2017).*
Wang et al.; Efficient delivery of genome-editing proteins using bioreducible lipid nanoparticles; CrossMark; PNAS; Mar. 15, 2016 vol. 113 No. 11 2868-2873 (Year: 2016).*
Wang et al.; Efficient delivery of genome-editing proteins using bioreducible lipid nanoparticles; CrossMark; PNAS; Mar. 15, 2016 vol. 113 No. 11 2868-2873; supporting information (Year: 2016).*
Maeki et al.; Advances in microfluidics for lipid nanoparticles and extracellular vesicles and applications in drug delivery systems; Elsevier; Advanced Drug Delivery Reviews 128 (2018) 84-100 (Year: 2018).*
Yang et al.; A microfluidic method to synthesize transferrin-lipid nanoparticles loaded with siRNA LOR-1284 for therapy of acute myeloid leukemia; CrossMark; Nanoscale, 2014, 6,9742-9751 (Year: 2014).*
DOPE; https://www.echelon-inc.com/product/dope-181-181-pe/; site accessed Jun. 2024 (Year: 2021).*
https://www.synthego.com/guide/how-to-use-crispr/sgrna#:~:text=sgRNA%20is%20an%20abbreviation%20for,vivo%20from%20a%20DNA%20template. site accessed Jun. 2024 (Year: 2021).*
Google Search sgRNA accessed 2025 (Year: 2025).*
Office Action for Chinese Patent Application No. 202080050354.0, mailed Nov. 16, 2023 (19 pages).
Cho et al., Lecithin nano-liposomal particle as a CRISPR/Cas9 complex delivery system for treating type 2 diabetes. Nanobiotechnol. 2019; 17:19.
International Search Report issued in International Application No. PCT/JP2020/020895, mailed Aug. 18, 2020.
Lee et al., "Nanoparticle delivery of Cas9 ribonucleoprotein and donor DNA in vivo induces homology-directed DNA repair," Nat Biomed Eng. 2017; 1: 889-901.
Leung et al., "Lipid Nanoparticles Containing siRNA Synthesized by Microfluidic Mixing Exhibit an Electron-Dense Nanostructured Core," J. Phys. Chem. C. 2012; 116: 18440-18450.
Li et al., "Intracellular delivery and biodistribution study of CRISPR/Cas9 ribonucleoprotein loaded bioreducible lipidoid nanoparticles," Biomaterials Science. 2019; vol. 7.

(Continued)

*Primary Examiner* — Robert A Wax
*Assistant Examiner* — John W Lippert, III
(74) *Attorney, Agent, or Firm* — Licata & Tyrrell P.C.; Kathleen A. Tyrrell

(57) ABSTRACT

The present invention addresses the problem of providing a lipid nanoparticle in which a nucleic acid, etc., required in genome editing is encapsulated and which can be produced by an alcohol dilution method using flow channels and contributes to high genome editing efficiency. The present invention pertains to a lipid nanoparticle which comprises a lipid component, a DNA nuclease, a guide RNA and a single-stranded oligonucleotide, wherein: the lipid component comprises a pH-sensitive cationic lipid, a neutral phospholipid and a polyalkylene glycol-modified lipid; the ratio of the pH-sensitive cationic lipid relative to the total lipids constituting the lipid nanoparticle is 30-50 mol %; the ratio of the neutral phospholipid relative to the total lipids constituting the lipid nanoparticle is 20-50 mol %; and the ratio of the polyalkylene glycol-modified lipid relative to the total lipids constituting the lipid nanoparticle is 1-4 mol %.

10 Claims, 15 Drawing Sheets

Specification includes a Sequence Listing.

(56) References Cited

OTHER PUBLICATIONS

Li et al., "Combinatorial library of chalcogen-containing lipidoids for intracellular delivery of genome-editing proteins," Biomaterials. 2018; 178: 652-662.

Mout et al., "Efficient Gene Editing through Direct Cytosolic Delivery of CRISPR/Cas9-Ribonucleoprotein," ACS Nano. 2017; 11(3): 2452-2458.

Richardson et al., "Non-homologous DNA increases gene discruption efficiency by altering DNA repair outcomes," Nature Communications. 2016; 7: 12463.

Stroock et al., "Chaotic Mixer for Microchannels," SCIENCE. 2002; 295: 647-651.

Sun et al., "Efficient Delivery of CRISPR-Cas9 for Genome Editing via Self-Assembled DNA Nanoclews," Angew Chem Int Ed Engl. 2015; 54(41): 12029-12033.

Wang et al., "Efficient delivery of genome-editing proteins using bioreducible lipid nanoparticles," PNAS. 2016; 113(11): 2868-2873.

Office Action for Chinese Patent Application No. 202080050354.0, mailed Jul. 7, 2023 (21 pages).

Sato et al., "Understanding structure-activity relationships of ph-sensitive cationic lipids facilitates the rational identification of promising lipid nanoparticles for delivering siRNAs in vivo", Journal of Controlled Release. 2019; 295:140-152.

Chinese Office Action issued Apr. 30, 2024, in corresponding Chinese application 202080050354.0.

English machine translation of Chinese Office Action issued Apr. 30, 2024, in corresponding Chinese application 202080050354.0.

Supplementary European Search Report for European Patent Application No. 20815073.0, mailed Dec. 21, 2022.

Wang et al., "Supporting Information: Efficient delivery of genome-editing proteins using bioreducible lipid nanoparticles," Proceedings of the National Academy of Sciences. 2016; 113(11):2868-73.

Newly prepared English machine translation of Chinese Office Action issued Apr. 30, 2024, in corresponding Chinese application 202080050354.0.

Japanese Office Action in corresponding Japanese Patent Application No. 2021-522808, dated Apr. 3, 2024, with English machine translation.

Japanese Office Action in corresponding Japanese Patent Application No. 2021-522808, dated Aug. 28, 2024, with English machine translation.

* cited by examiner (A)

(B)

LIPID NANOPARTICLE

TECHNICAL FIELD

The present invention relates to a lipid nanoparticle useful as a carrier of RNA-protein complex (ribonucleoprotein; RNP) available in genome editing by CRISPR systems.

The present invention claims priority on the basis of Japanese Patent Application No. 2019-101203, filed in Japan on May 30, 2019, the contents of which are incorporated herein by reference.

BACKGROUND OF THE INVENTION

Genome editing techniques are biotechnologies which make it possible to selectively introduce a mutation or insert an arbitrary DNA sequence containing a gene into an arbitrary target genomic DNA region. The application of genome editing techniques to medical treatments has been highly desired because such an application leads to the realization of fundamental treatment of various refractory diseases such as hereditary diseases and infectious diseases. Among these, the CRISPR (clustered regularly interspaced short palindromic repeats)/Cas9 (CRISPR-associated protein 9) system, which is a third-generation genome editing technique, currently attracts the most attention because of its excellent gene knockout efficiency and ease of design. The system serves as an RNP composed of a Cas9 protein having DNA double-strand break (DSB) activity and a gRNA (guide RNA), which is a chimeric RNA composed of crRNA (CRISPR RNA) and tracrRNA (trans-activating CRISPR RNA) derived from bacteria. Accordingly, it is possible to induce knockout of target genes by expressing the RNP in a target cell or delivering the RNP into a target cell. It is further possible to induce gene knockin by simultaneously delivering a donor DNA.

Examples of the delivery procedure into a target cell in genome editing techniques include: a procedure in which an RNP is expressed in the cell by introducing DNA or RNA; and a procedure in which an RNP is directly introduced into the cell. In the case of the former procedure, delivery techniques using viral vectors or non-viral vectors, for example, have been established to some extent, and therefore the procedure can be conducted relatively easily, but the Cas9 protein expresses for a relatively long-term period, and therefore a mutation in an untargeted DNA region (off-target mutation) tends to occur. In contrast, in the case of the latter procedure, the RNP rapidly degrades and disappears after a mutation is introduced in a target DNA region, and therefore the off-target mutation is suppressed to the minimum. Particularly, in the case of genome editing accompanied with DSB, the suppression of the off-target mutation is extremely important because effects thereof are maintained permanently as long as edited cells survive.

There are several reports relating to the development of techniques that allow delivery of RNPs. Examples thereof include: a method in which DNA Nanoclews are used (Non-Patent Document 1); a method in which reducible lipid nanoparticles in vivo are used (Non-Patent Document 2); a method in which conjugates with gold nanoparticles are used (Non-Patent Document 3); a method in which lipidoids are used (Non-Patent Document 4); and a method in which lecithin nano-liposomal particles are used (Non-Patent Document 5). CRISPR-Gold has been reported as an example in which gene knockin is induced (Non-Patent Document 6). However, problems in which, for example, a high concentration of Cas9 is required to induce gene knockdown in cultured cells remain in genome editing efficiency.

In contrast, there is a method based on an alcohol dilution method using flow channels as a preparation method of lipid nanoparticles in which a nucleic acid or the like is encapsulated. For example, it has been reported that lipid nanoparticles having a diameter of approximately 30 nm can be prepared reproducibly by using microflow channels equipped with a built-in three-dimensional micromixer that allows instantaneous mixing of two liquids to be realized (Non-Patent Document 7). It has also been reported that the use of a flow channel structure having a simple two-dimensional structure in which baffles (baffle plates) having a fixed width relative to a flow channel width are disposed alternately from two sides on a micro-sized flow channel through which a feedstock solution is passed makes it possible to form a nano-sized lipid particle formation system, the particle size controllability of which is higher than that of a flow channel structure using a conventional three-dimensional mixer (Patent Document 1). In recent years, these preparation methods of lipid nanoparticles have been applied mainly to prepare lipid nanoparticles (LNP) carrying lipid-soluble drugs or nucleic acids such as siRNA (short interfering RNA) or mRNA. For example, lipid nanoparticles containing a pH-sensitive cationic lipid as a constituent lipid have been reported as lipid nanoparticles which serve as carriers to efficiently deliver nucleic acids such as siRNA into target cells (Patent Document 2).

DOCUMENTS OF RELATED ART

Patent Documents

Patent Document 1: International Patent Application Publication No. 2018/190423
Patent Document 2: International Patent Application Publication No. 2018/230710

Non-Patent Documents

Non-Patent Document 1: Sun et al., Angewandte Chemie International Edition, 2015, vol. 54, p. 12029-12033.
Non-Patent Document 2: Wang et al., Proceedings of the National Academy of Sciences of the United States of America, 2016, vol. 113, p. 2868-2873.
Non-Patent Document 3: Mout et al., American Chemical Society Nano, 2017, vol. 11, p. 2452-2458.
Non-Patent Document 4: Li et al., Biomaterials, 2018, vol. 178, p. 652-662.
Non-Patent Document 5: Cho et al., Journal of Nanobiotechnology, 2019, vol. 17, p. 19.
Non-Patent Document 6: Lee et al., Nature Biomedical Engineering, 2017, vol. 1, p. 889-901.
Non-Patent Document 7: Leung et al., Journal of Physical Chemistry C Nanomater Interfaces, 2012, vol. 116(34), p. 18440-18450.
Non-Patent Document 8: Stroock et al., Science, 2002, vol. 295, p. 647-651

SUMMARY OF THE INVENTION

Problems to be Solved by the Invention

Proteins such as RNP tend to be inactivated irreversibly by various physical parameters such as organic solvents such as alcohol, or the pH, salt concentration, or temperature of a buffer during preparation of particles, as compared to low molecular drugs or nucleic acids which have been used conventionally. Therefore, there have been no previous reports on the production of lipid nanoparticle formulations carrying RNP based on the alcohol dilution method.

The present invention aims to provide lipid nanoparticles which encapsulate RNPs or the like which are required to conduct genome editing, can be produced by an alcohol dilution method using a flow channel, and are excellent in genome editing efficiency.

Means to Solve the Problems

The present inventors found in genomic editing by the CRISPR/Cas9 system that an RNP, which is a complex of crRNA, tracrRNA and Cas9 protein can be efficiently loaded on a lipid nanoparticle having a lipid membrane structure of a particular constitution containing a pH-sensitive cationic lipid by making the RNP form a complex with a single-stranded oligonucleotide (ssON) containing a base sequence region complementary to the crRNA, thereby negatively charging the complex, and thus completed the present invention.

The present invention provides the following lipid nanoparticle.

(1) A lipid nanoparticle containing: lipid components; a DNA nuclease; a guide RNA, and a single-stranded oligonucleotide, wherein the lipid components contain: a pH-sensitive cationic lipid of the following general formula (I):

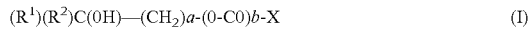

$(R^1)(R^2)C(OH)—(CH_2)a\text{-}(O\text{-}CO)b\text{-}X$  (I)

(in the formula (I), a is an integer of 3 to 5; b is 0 or 1; $R^1$ and $R^2$ are each independently a group of the following general formula (A)):

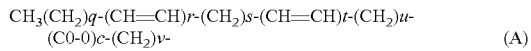

$CH_3(CH_2)q\text{-}(CH=CH)r\text{-}(CH_2)s\text{-}(CH=CH)t\text{-}(CH_2)u\text{-}(CO\text{-}O)c\text{-}(CH_2)v\text{-}$  (A)

(in the formula (A), q is an integer of 1 to 9; r is 0 or 1; s is an integer of 1 to 3; t is 0 or 1; u is an integer of 1 to 8; c is 0 or 1; v is an integer of 4 to 12; and q+2r+s+2t+u+c+v is an integer of 19 or more, with the proviso that groups in which both b and c are 0, q is an integer of 3 to 5, both r and t are 1, s is 1, and u+v is an integer of 6 to 10 are excluded);

X is a group of the following general formula (B):

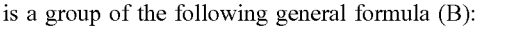

$—(CH_2)d\text{-}N(R^3)(R^4)$  (B)

(in the formula (B), d is an integer of 0 to 3; and $R^3$ and $R^4$ are each independently a $C_{1-4}$ alkyl group or a $C_{2-4}$ alkenyl group (1 or 2 hydrogen atoms of the $C_{1-4}$ alkyl group or the $C_{2-4}$ alkenyl group may be substituted with a phenyl group), $R^3$ and $R^4$ may be bonded together to form a 5-membered to 7-membered non-aromatic hetero ring (1 or 2 hydrogen atoms of the ring may be substituted with a $C_{1-4}$ alkyl group or a $C_{2-4}$ alkenyl group)), or a 5-membered to 7-membered non-aromatic hetero ring group (a carbon atom of the group is bonded to (O—CO)b-, and 1 or 2 hydrogen atoms of the ring may be substituted with a $C_{1-4}$ alkyl group or a $C_{2-4}$ alkenyl group)); a neutral phospholipid; and a polyalkylene glycol-modified lipid, the ratio of the pH-sensitive cationic lipid relative to the total amount of lipids constituting the lipid nanoparticle is 30% by mol to 50% by mol, the ratio of the neutral phospholipid relative to the total amount of lipids constituting the lipid nanoparticle is 20% by mol to 50% by mol, and the ratio of the polyalkylene glycol-modified lipid relative to the total amount of lipids constituting the lipid nanoparticle is 1% by mol to 4% by mol.

(2) The lipid nanoparticle according to (1), wherein the neutral phospholipid is a neutral glycerophospholipid having a $C_{12-24}$ saturated or unsaturated fatty-acid residue.

(3) The lipid nanoparticle according to (1), wherein the neutral phospholipid is a phosphatidylethanolamine having a $C_{12-24}$ unsaturated fatty-acid residue.

(4) The lipid nanoparticle according to any one of (1) to (3), wherein the pH-sensitive cationic lipid is a polyethylene glycol-modified lipid.

(5) The lipid nanoparticle according to any one of (1) to (4), wherein the DNA nuclease is a Cas9 protein, and
the guide RNA is composed of crRNA and tracrRNA.

(6) The lipid nanoparticle according to (5), wherein the Cas9 protein is a protein having either RuvC nuclease activity or HNH nuclease activity.

(7) The lipid nanoparticle according to any one of (1) to (4), wherein the DNA nuclease is a Cpf1 protein.

(8) A genome editing method including introducing the lipid nanoparticle of any one of (1) to (7) into cells.

(9) A preparation method of the lipid nanoparticle of any one of (1) to (7) including using a flow channel structure, wherein the flow channel structure includes a first introducing passage configured to introduce a first fluid and a second introducing passage configured to introduce a second fluid, which are mutually independent and join together while each having fixed lengths, to form a single dilution flow channel, the dilution flow channel includes a two-dimensionally bent-flow channel portion in at least a portion thereof, the bent-flow channel portion is configured such that an axial direction of the dilution flow channel upstream therefrom or an extending direction thereof is defined as an X direction, a width direction of the dilution flow channel that perpendicularly intersects with the X direction is defined as a Y direction, and the flow channel width of the dilution flow channel upstream therefrom is defined as $y_0$, and at least two structural elements which define flow channel width of the dilution flow channel by alternately protruding from two side surfaces, facing each other in the Y direction, of the dilution flow channel towards a center of the flow channel at a fixed height $h_1, h_2, \ldots$ of $\frac{1}{2}y_0$ or more and less than $1_{y0}$ in an approximate Y direction (approximate +Y direction or approximate −Y direction) and at a fixed width $X_1, X_2, \ldots$ in the X direction are provided at fixed intervals $d_1, d_2, \ldots$, and a lipid solution in which lipid components are dissolved in ethanol and which is introduced from the first introducing passage; and an aqueous solution which contains a DNA nuclease, a guide RNA and a single-stranded oligonucleotide, and which is introduced from the second introducing passage, and which has a pH of at least 5.0, have a total flow quantity of 1 μL/minute to 100 mL/minute, and a ratio of a flow rate of the lipid solution to a flow rate of the aqueous solution is at least 7.

(10) The preparation method of the lipid nanoparticle according to (9), wherein the flow channel structure further includes a third introducing passage configured to introduce a third fluid, and the first introducing passage, the second introducing passage, and the third introducing passage join together while each having fixed lengths to form a single dilution flow channel such that the first fluid introduced from the first introducing passage contacts with the third fluid introduced from the third introducing passage before joining the second fluid introduced from the second introducing passage.

Effects of the Invention

The lipid nanoparticle according to the present invention makes it possible to conduct efficiently genome editing of target cells, since the RNP is loaded on the lipid nanoparticle having a lipid membrane structure of a particular constitution containing a pH-sensitive cationic lipid. In addition, the lipid nanoparticle according to the present invention may be prepared by an alcohol dilution method, since the RNP loaded on the lipid membrane structure contains ssON, and is negatively charged.

EMBODIMENTS FOR CARRYING OUT THE INVENTION

Figure 1A:
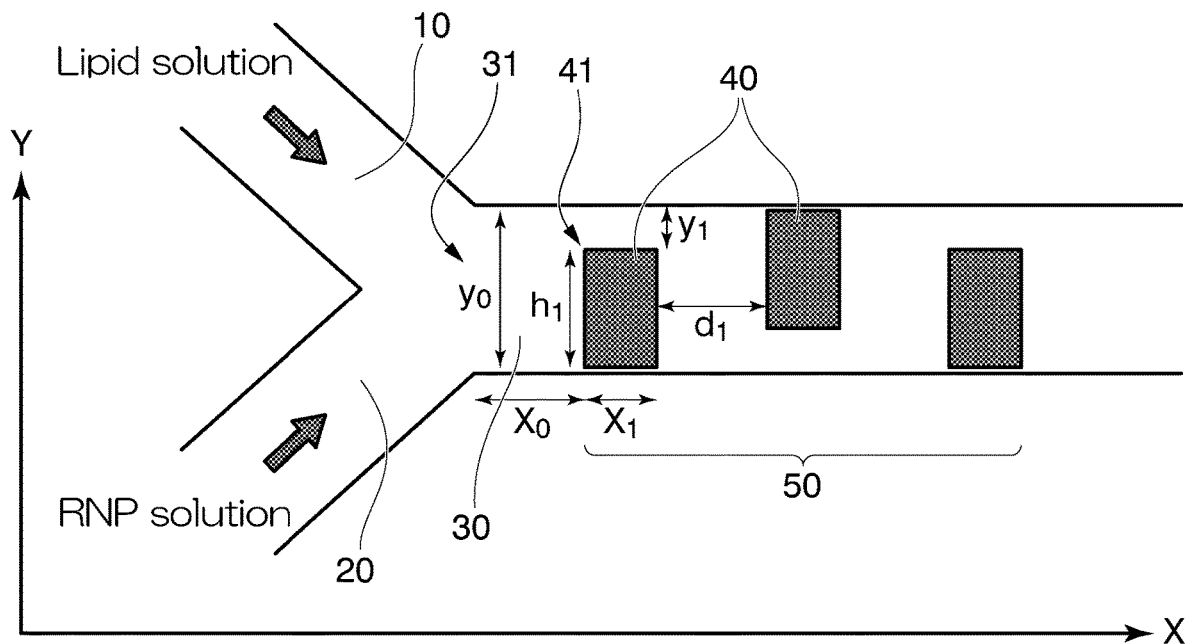
FIG. 1A is a drawing schematically showing the structure of the flow channel in one embodiment available to prepare the lipid nanoparticle according to the present invention.

A lipid nanoparticle according to the present invention is to be used as a carrier to introduce an RNP into a target cell in a CRISPR system, and is a lipid nanoparticle in which the RNP, which is a complex composed of DNA nuclease, guide RNA (gRNA), and ssON, which are used in a genome editing procedure, is loaded on a lipid membrane structure of a particular constitution containing a pH-sensitive cationic lipid. Examples of the RNP to be loaded on the lipid nanoparticle include a complex composed of Cas9 protein, crRNA, tracrRNA, and ssON. Since the RNP is directly loaded on the lipid nanoparticle to be introduced into a target cell, the off-target mutation is suppressed in comparison with the method of introducing a gene encoding DNA nuclease, such as Cas9 protein, to allow expression thereof.

[DNA Nuclease]

In the present invention and the present specification, the DNA nuclease loaded on the lipid nanoparticle is an enzyme which binds to DNA in a gRNA-dependent manner, and then recognizes and cleaves double-stranded DNA formed by pairing with a portion of the gRNA. Examples of the DNA nuclease include Cas9 and Cpf1.

<Cas9 Protein>

In the present invention and the present specification, a Cas9 protein is a protein which binds to DNA in a gRNA-dependent manner and has at least one selected from the group consisting of RuvC nuclease activity and HNH nuclease activity. The Cas9 protein having both RuvC nuclease activity and HNH nuclease activity cleaves a duplex of genomic DNA. The Cas9 protein having either RuvC nuclease activity or HNH nuclease activity cleaves only one of a duplex of genomic DNA.

The Cas9 protein used in the present invention may be a wild-type Cas9 protein derived from a bacterium having a CRISPR system, or an engineered protein obtained by the modification of the wild-type protein. Examples of the bacterium having a CRISPR system include *Streptococcus pyogenes, Staphylococcus aureus, Neisseria meningitidis, Campylobacter jejuni, Geobacillus stearothermophilus, Streptococcus thermophilus*, and *Treponema denticola*. Examples of the engineered protein obtained by the modification of the wild-type Cas9 protein include a mutant in which a mutation that inactivates either RuvC nuclease activity or HNH nuclease activity is introduced. Examples of such a mutant include a mutant (Cas9 (D10A)) in which the $10^{th}$ aspartic acid of the wild-type Cas9 protein is replaced with alanine. Since the Cas9 (D10A) serves as a DNA nickase, it is also referred to as Cas9 nickase (Cas9n). Additional examples of the engineered protein include a mutant in which a mutation that does not affect the nuclease activity of the wild-type Cas9 protein is introduced.

The Cas9 protein available in the present invention may be a protein in which various peptides are added to a wild-type Cas9 protein or an engineered protein, or a chimeric protein in which another protein is fused to a wild-type Cas9 protein or an engineered protein. Examples of the peptides include tag peptides such as His tag, Myc tag, and Flag tag, and signal peptides such as nuclear transfer signal peptides. Examples of another protein to be fused to a wild-type or engineered Cas9 protein include GST and fluorescent proteins.

<Cpf1 Protein>

In the present invention and the present specification, a Cpf1 protein is a protein which binds to DNA in a gRNA-dependent manner and has only RuvC nuclease activity. The Cas9 protein having both RuvC nuclease activity and HNH nuclease activity cleaves a duplex of genomic DNA to form a blunt end, whilst the Cpf1 protein forms a 5'-protruding end.

The Cpf1 protein available in the present invention may be a wild-type Cpf1 protein derived from a bacterium having a CRISPR/Cpf1 system, or an engineered protein obtained by modifying the wild-type protein. Examples of the bacterium having a CRISPR/Cpf1 system include Acidaminococcus sp., and Lachnospiraceae bacterium. Examples of the engineered protein obtained by modifying the wild-type Cpf1 protein include a mutant in which a mutation which increases the nuclease activity is introduced, and an engineered protein in which a mutation which does not affect nuclease activity is introduced.

The Cpf1 protein available in the present invention may be a protein in which various peptides are added to a wild-type Cpf1 protein or an engineered protein, or a chimeric protein in which another protein is fused to a wild-type Cpf1 protein or an engineered protein. Examples of the peptides and another protein include the same as mentioned for the Cas9 protein.

[gRNA]

In the present invention and the present specification, gRNA is RNA having a base sequence pairable with a target sequence on genomic DNA to be cleaved by a DNA nuclease (base sequence of a target of genome editing). The "base sequence that can pair with a target sequence" is generally a base sequence that is homologous (identical) or complementary to a target sequence so as to suppress recognition of a region other than the target sequence. The gNRA may consist of a single RNA or a complex of at least two RNAs.

<crRNA and tracrRN>

In the case where the DNA nuclease to be loaded on the lipid nanoparticle is the Cas9 protein, crRNA and tracrRNA may be used as the gRNA. The crRNA is a single strand RNA which is derived from a bacterium having a CRISPR system and contains: a region of a base sequence complementary to a part of tracrRNA (region bindable with tracrRNA) and a region of a base sequence homologous or complementary to a target sequence on genomic DNA (region bindable with genomic DNA). The tracrRNA is a single strand RNA which is similarly derived from a bacterium having a CRISPR system, contains a region of a base sequence complementary to a part of the crRNA (region bindable with crRNA), and can hybridize to the crRNA on the region to form a hairpin structure. The hairpin structure is recognized by the Cas9 protein and an RNP is formed. The crRNA and the tracrRNA may be each independent single strand RNA, or may be bonded together via an appropriate RNA linker to form a single strand RNA. Examples of the bacterium having a CRISPR system include the same as mentioned above. The Cas9 protein, the crRNA and the tracrRNA may be derived from the same type of bacterium, or different types of bacteria. The crRNA and the tracrRNA may consist of natural RNA, or a part or the entirety thereof may contain modified RNA or an artificial nucleic acid, unless the CRISPR/Cas9 system is impaired.

<gRNA Used with Cpf1 Protein>

In the case where the DNA nuclease loaded on the lipid nanoparticle is Cpf1 protein, the gRNA may be RNA containing a target sequence in a similar manner to crRNA, and no tracrRNA is required. Thus, gRNA can be shortened in comparison with the case where the Cas9 protein is used. The gRNA may also consist of natural RNA, or a part or the entirety thereof may contain modified RNA or an artificial nucleic acid, unless the CRISPR/Cpf1 system is impaired.

<Target Sequence>

The base sequence of the region immediately followed by the PAM sequence is generally selected as the target sequence. The PAM sequence is a sequence recognized by a DNA nuclease such as the Cas9 protein, and is determined depending on the used DNA nuclease such as the Cas9 protein. Examples of the PAM sequence recognized by the Cas9 protein include 5'-NGG (N: A, G, C, or T). Examples of the PAM sequence recognized by the Cpf1 protein include 5'-TTTV (V: A, G, or C), and 5'-TTTN (N: A, G, C, or T). The base length of the target sequence in the gRNA such as crRNA is not particularly limited, and may be, for example, approximately 15 bases to 30 bases, and more preferably 18 bases to 22 bases.

[ssON]

The ssON available in the present invention includes a region pairable with a part of the gRNA. Thus, a region pairable with the gRNA constituting a complex with the DNA nuclease to be loaded on the lipid nanoparticle is included. Thus, an RNP which is a complex of the DNA nuclease, gRNA and ssON is formed. The ssON may be an oligonucleotide consisting of DNA, an oligonucleotide consisting of RNA, or a chimeric oligonucleotide containing both DNA and RNA. The ssON may consist of natural RNA or DNA, or a part or the entirety thereof may contain a modified nucleic acid or an artificial nucleic acid, unless the CRISPR system is impaired.

In the case where the DNA nuclease loaded on the lipid nanoparticle is a Cas9 protein, a region of the base sequence complementary to a partial region of the crRNA other than the region bindable with tracrRNA is contained. The ssON and the crRNA are hybridized via the region complementary to the crRNA (region bindable with crRNA). In other words, the RNP loaded on the lipid nanoparticle according to the present invention is formed by hybridizing the crRNA with the tracrRNA and hybridizing the crRNA with the ssON to form a triple complex, followed by forming a complex of the triple complex and the Cas9 protein. The region hybridizable with the ssON in the crRNA (region bindable with the ssON) is not particularly limited, provided that the region allows the crRNA to hybridize simultaneously with the tracrRNA and the ssON to form the triple complex and allows the triple complex to form a hairpin structure recognizable by the Cas9 protein. For example, the region bindable with the ssON in the crRNA may contain a part or the entirety of the genomic DNA binding region, or may be identical to the genomic DNA binding region. In the case of a double nicking method using a Cas9 nickase (Cas9n) in which either RuvC nuclease activity or HNH nuclease activity is inactivated, two types of guide RNA are used. In the case of a lipid nanoparticle in which the loaded DNA nuclease is the Cas9n and an RNP that allows double nicking is loaded, two types of ssON which are each hydridizable to the guide RNA are used.

In the case where an intended gene fragment is knocked in a cleaved genomic DNA by the CRISPR system, the ssON may be used as a donor DNA to be knocked in. For example, an ssON including a region in which a 40 bp to 60 bp homologous sequence region (homology arm) that allows homologous recombination is added at both ends of the gene fragment to be knocked-in in addition to the region bindable with the gRNA, such as crRNA, serves as a donor DNA.

The Cas9 protein and the Cpf1 protein are positively charged unlike nucleic acids, and therefore the loading efficiency thereof on a lipid nanoparticle containing a pH-sensitive cationic lipid as a lipid component constituting the lipid membrane is low. In contrast, the lipid nanoparticle according to the present invention contains not only gRNA such as crRNA and tracrRNA but also ssON as nucleic acids which form complexes with DNA nuclease such as Cas9 protein. Thus, the RNP contains a large amount of nucleic acids and the positive charge of the RNP is suppressed to increase the negative charge thereof, thereby realizing efficient loading on the lipid nanoparticle containing a pH-sensitive cationic lipid. The base length of the ssON available in the present invention may be a length sufficient to negatively charge the RNP, and may be appropriately determined taking into account the base length of gRNA, such as crRNA and tracrRNA, or the type of Cas9 protein or the like. The length of the ssON may be, for example, approximately 50 base length to 500 base length.

Determination of target sequences on genomic DNA, design of base sequence of gRNA such as crRNA and tracrRNA, design of base sequence of ssON, or the like, may be conducted by conventional methods utilizing commonly used molecular biological tools based on base sequence information of genomic DNA. For example, the design of gRNA may be conducted by utilizing a design tool such as CRISPR Design Tool (Horizon Discovery) or TrueDesign Genome Editor (Invitrogen).

[Lipid Component]

The lipid nanoparticle according to the present invention is a lipid nanoparticle in which an RNP is loaded on the lipid membrane structure. At least a pH-sensitive cationic lipid, a neutral phospholipid, and a polyalkylene glycol-modified lipid are contained as lipid components constituting the lipid membrane structure.

<pH-Sensitive Cationic Lipid>

The pH-sensitive cationic lipid contained in the lipid nanoparticle according to the present invention is a cationic lipid of the following general formula (I) (hereinafter, may be referred to as "pH-sensitive cationic lipid according to the present invention").

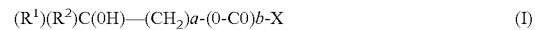

$(R^1)(R^2)C(OH)—(CH_2)a-(O-CO)b-X$ (I)

In the general formula (I), a is an integer of 3 to 5, and preferably 4.

b is 0 or 1. In the case where b is 0, the group of —O—CO— is absent, and a single bond is meant.

In the general formula (I), $R^1$ and $R^2$ are each independently a group of the following general formula (A). In the general formula (A), q is an integer of 1 to 9; r is 0 or 1; s is an integer of 1 to 3; t is 0 or 1; u is an integer of 1 to 8; c is 0 or 1; and v is an integer of 4 to 12. In the case where both b and c are 0, the cases where q is an integer of 3 to 5, both r and t are 1, s is 1, and u+v is an integer of 6 to 10 are excluded.

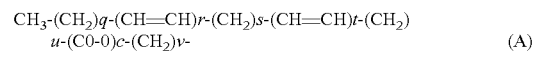

$CH_3-(CH_2)q-(CH=CH)r-(CH_2)s-(CH=CH)t-(CH_2)u-(C0-O)c-(CH_2)v-$ (A)

It is preferable that the hydrocarbon chains of $R^1$ and $R^2$ in the pH-sensitive cationic lipid according to the present invention be relatively long chains from the viewpoint of stability of the lipid nanoparticle according to the present invention. It is specifically preferable that $R^1$ and $R^2$ in the pH-sensitive cationic lipid according to the present invention be groups having a carbon number of at least 20, that is, in the general formula (A), q+2r+s+2t+u+c+v be an integer of 19 or more. Among them, q+2r+s+2t+u+c+v in the pH-sensitive cationic lipid according to the present invention is preferably an integer of 19 to 33, more preferably an integer of 19 to 31, even more preferably 21 to 31, and even more preferably an integer of 21 to 27.

It is preferable that $R^1$ and $R^2$ of the pH-sensitive cationic lipid according to the present invention be a group of the general formula (A): in which r is 1, t is 0, q is an integer of 5 to 11, and preferably an integer of 6 to 10, s+u is an integer of 5 to 11, and preferably an integer of 6 to 10, c is 1, v is an integer of 4 to 12, and q+s+u+v is an integer of 16 or more; in which r is 0, t is 1, q+s is an integer of 5 to 11, and preferably an integer of 6 to 10, u is an integer of 5 to 8, c is 1, v is an integer of 4 to 12, and q+s+u+v is an integer of 16 or more; in which both r and t are 0, q+s+u is an integer of 13 to 23, and preferably an integer of 15 to 21, c is 1, v is an integer of 4 to 12, and q+s+u+v is an integer of 18 or more; or in which both r and t are 0, q+s+u is an integer of 13 to 23, and preferably 15 to 21, c is 1, v is an integer of 6 to 10, and q+s+u+v is an integer of 18 or more.

Although $R^1$ and $R^2$ in the pH-sensitive cationic lipid according to the present invention may be any of groups of the general formula (A) and may be identical to or different from each other, it is preferable that $R^1$ and $R^2$ be identical to each other.

In the general formula (I), X is a group of the following general formula (B) or a 5-membered to 7-membered non-aromatic hetero ring group. The 5-membered to 7-membered non-aromatic hetero ring group as X bonds with a group of (O—CO)b- via a carbon atom thereof.

$$-(CH_2)d\text{-}N(R^3)(R^4) \qquad (B)$$

In the general formula (B), d is an integer of 0 to 3. In the case where d is 0, there is no group of —(CH$_2$)—, and a single bond is meant.

In the general formula (B), $R^3$ and $R^4$ are each independently a $C_{1-4}$ alkyl group (alkyl group having 1 to 4 carbon atoms) or a $C_{2-4}$ alkenyl group (alkenyl group having 1 to 4 carbon atoms). One or two hydrogen atoms of the $C_{1-4}$ alkyl group or the $C_{2-4}$ alkenyl group as $R^3$ and $R^4$ may be substituted with a phenyl group.

Examples of the $C_{1-4}$ alkyl group include a methyl group, an ethyl group, a propyl group, an isopropyl group, a n-butyl group, an isobutyl group, and a t-butyl group. Examples of the $C_{2-4}$ alkenyl group include a vinyl group, a 1-propenyl group, a 2-propenyl group, a 1-methylvinyl group, a 2-methyl-1-propenyl group, a 1-butenyl group, a 2-butenyl group, and a 3-butenyl group.

In the general formula (B), $R^3$ and $R^4$ may be bonded together to form a 5-membered to 7-membered non-aromatic hetero ring. Examples of the 5-membered to 7-membered non-aromatic hetero ring formed by $R^3$ and $R^4$ bonded together include a 1-pyrrolidinyl group, a 1-piperidinyl group, a 1-morpholinyl group, and a 1-piperazinyl group. One or two hydrogen atoms in the 5-membered to 7-membered non-aromatic hetero ring formed by $R^3$ and $R^4$ bonded together may be substituted with a $C_{1-4}$ alkyl group or a $C_{2-4}$ alkenyl group. In the case where 2 hydrogen atoms in the ring may be substituted with a $C_{1-4}$ alkyl group or a $C_{2-4}$ alkenyl group, the hydrogen atoms may be substituted with groups identical to or different from each other.

In the case where X is a 5-membered to 7-membered non-aromatic hetero ring group in the general formula (I), examples of the hetero atom included in the hetero ring group include a nitrogen atom, an oxygen atom, and a sulfur atom. One hetero atom, or at least two hetero atoms identical to or different from each other may constitute the hetero ring in the hetero ring group. Although the hetero ring in the hetero ring group may be a saturated hetero ring and may contain one double bond or at least two double bonds, the hetero ring is not an aromatic ring.

The pH-sensitive cationic lipid according to the present invention is preferably a lipid of the general formula (I), in which a is an integer of 3 to 5, b is 1, X is a 5-membered to 7-membered non-aromatic hetero ring group (of which a carbon atom is bonded with (O—CO)b-), preferably a 1-pyrrolidinyl group, a 1-piperidinyl group, a 1-morpholinyl group, or a 1-piperazinyl group (of which a carbon atom is bonded with (O—CO)b-, and 1 hydrogen atom may be substituted with a $C_{1-4}$ alkyl group or a $C_{2-4}$ alkenyl group), $R^1$ and $R^2$ are each independently a group of the general formula (A), in which r is 1, t is 0, q is an integer of 5 to 11, preferably is an integer of 6 to 10, s+u is an integer of 5 to 11, preferably is an integer of 6 to 10, c is 1, v is an integer of 4 to 12, and q+s+u+v is an integer of 16 or more; a lipid of the general formula (I), in which a is an integer of 3 to 5, b is 1, X is a 5-membered to 7-membered non-aromatic hetero ring group (of which a carbon atom is bonded with (O—CO)b-), preferably a 1-pyrrolidinyl group, a 1-piperidinyl group, a 1-morpholinyl group, or a 1-piperazinyl group (of which a carbon atom is bonded with (O—CO)b-, and one hydrogen atom may be substituted with a $C_{1-4}$ alkyl group or a $C_{2-4}$ alkenyl group), $R^1$ and $R^2$ are each independently a group of general formula (A), in which r is 0, t is 1, q+s is an integer of 5 to 11, preferably is an integer of 6 to 10, u is an integer of 5 to 8, c is 1, v is an integer of 4 to 12, and q+s+u+v is an integer of 16 or more; a lipid of the general formula (I) in which a is an integer of 3 to 5, b is 0, X is a group of the general formula (B), in which d is 0, $R^3$ and $R^4$ are each independently a $C_{1-4}$ alkyl group or a $C_{2-4}$ alkenyl group (1 or 2 hydrogen atoms of the $C_{1-4}$ alkyl group or the $C_{2-4}$ alkenyl group as $R^3$ and $R^4$ may be substituted with a phenyl group), $R^1$ and $R^2$ are each independently a group of the general formula (A), in which r is 1, t is 0, q is an integer of 5 to 11, preferably is an integer of 6 to 10, s+u is an integer of 5 to 11, preferably is an integer of 6 to 10, c is 1, v is an integer of 4 to 12, q+s+u+v is an integer of 16 or more; or a lipid of the general formula (I), in which a is an integer of 3 to 5, b is 0, X is a group of the general formula (B), in which d is 0, $R^3$ and $R^4$ are each independently a $C_{1-4}$ alkyl group or a $C_{2-4}$ alkenyl group (1 or 2 hydrogen atoms of the $C_{1-4}$ alkyl group or the $C_{2-4}$ alkenyl group as $R^3$ and $R^4$ may be substituted with a phenyl group), $R^1$ and $R^2$ are each independently a group of the general formula (A), in which r is 0, t is 1, q+s is an integer of 5 to 11, preferably is an integer of 6 to 10, u is an integer of 5 to 8, c is 1, v is an integer of 4 to 12, and q+s+u+v is an integer of 16 or more. Among these lipids, a lipid in which $R^1$ and $R^2$ are identical to each other is more preferable as the pH-sensitive cationic lipid of the general formula (I), and a lipid in which $R^1$ and $R^2$ are identical to each other and a is 4 is particularly preferable.

Although the pKa of the pH-sensitive cationic lipid of the general formula (I) is not particularly limited, the pKa is adjusted to, for example, approximately 4.0 to 9.0, preferably approximately 4.5 to 8.5, and more preferably approximately 6 to 8, and each substituent is preferably selected to obtain the pKa within the range.

The pH-sensitive cationic lipid of the general formula (I) may be prepared further easily by the method mentioned in examples of the present specification, for example. The lipid of the general formula (I) may be easily prepared by appropriately selecting feedstock compounds, reagents, and reaction conditions, with reference to the preparation method.

<Neutral Phospholipid>

The neutral phospholipid contained in the lipid component of the lipid nanoparticle according to the present invention (hereinafter, may be referred to as "neutral phospholipid according to the present invention") is a lipid in which the charge is neutral as a whole and a phosphate group and a positively charged-group are connected via a suitable linking group. Examples of the positively-charged group include an ammonium group and a quaternary ammonium group.

Glycerophospholipid or sphingophospholipid is preferable as the neutral phospholipid according to the present invention. Examples of the neutral glycerophospholipid include phosphatidylethanolamine, phosphatidylcholine, cardiolipin, and plasmalogen. Examples of the neutral sphingophospholipid include sphingomyelin, ceramide phosphoryl glycerol, and ceramide phosphoryl ethanolamine. Although the fatty-acid residue of the neutral glycerophospholipid or the neutral sphingophospholipid is not particularly limited, examples thereof include $C_{12\text{-}24}$ saturated or unsaturated fatty-acid residues, and $C_{14\text{-}20}$ saturated or unsaturated fatty-acid residues are preferable. Specific examples thereof include acyl groups derived from fatty acids such as lauric acid, myristic acid, palmitic acid, palmitoleic acid, stearic acid, oleic acid, linoleic acid, linolenic acid, arachidic acid, arachidonic acid, behenic acid, and lignoceric acid. In the case where the glycerolipid or the sphingolipid has at least two fatty-acid residues, all fatty-acid residues may be identical to or different from each other.

Glycerophospholipids having a $C_{12\text{-}24}$ saturated or unsaturated fatty-acid residue are preferable, neutral glycerophospholipids or neutral sphingophospholipids having a $C_{12\text{-}24}$ unsaturated fatty-acid residue are more preferable, and neutral glycerophospholipids having a $C_{12\text{-}24}$ unsaturated fatty-acid residue are further preferable as the neutral phospholipids according to the present invention from the viewpoint that the genome editing efficiency can be further improved. Among these, phosphatidylethanolamines having a $C_{12\text{-}24}$ unsaturated fatty-acid residue are preferable, phosphatidylethanolamines having a $C_{14\text{-}20}$ fatty-acid residue are further preferable, and dioleoylphosphatidylethanolamine (DOPE) is particularly preferable.

<Polyalkylene Glycol-Modified Lipid>

Although the polyalkylene glycol-modified lipid contained in the lipid component of the lipid nanoparticle according to the present invention (hereinafter, may be referred to as "polyalkylene glycol-modified lipid according to the present invention") is not particularly limited, provided that the lipid is modified by polyalkylene glycol, both the pH-sensitive cationic lipid and the neutral phospholipid are excluded. The polyalkylene glycol is a hydrophilic polymer, and the surface of the lipid nanoparticle can be modified by the polyalkylene glycol by constituting the lipid nanoparticle using the polyalkylene glycol-modified lipid as a lipid membrane constitution lipid. The surface modification by the polyalkylene glycol may improve the stability, such as blood retention, of the lipid nanoparticle.

Examples of the polyalkylene glycol include polyethylene glycol, polypropylene glycol, polytetramethylene glycol, and polyhexamethylene glycol. The weight-average molecular weight of the polyalkylene glycol is, for example, approximately 300 to 10,000, preferably approximately 500 to 10,000, and more preferably approximately 1,000 to 5,000.

For example, stearylated polyethylene glycol (such as PEG45 stearate (STR-PEG45)) may be used to modify the lipid by polyethylene glycol. In addition, although a polyethylene glycol derivative, such as N-[carbonyl-methoxypolyethylene glycol-2000]-1,2-dipalmitoyl-sn-glycero-3-phosphoethanolamine, n-[carbonyl-methoxypolyethylene glycol-5000]-1,2-dipalmitoyl-sn-glycero-3-phosphoethanolamine, N-[carbonyl-methoxypolyethylene glycol-750]-1, 2-distearoyl-sn-glycero-3-phosphoethanolamine, N-[carbonyl-methoxypolyethylene glycol-2000]-1,2-distearoyl-sn-glycero-3-phosphoethanolamine, or N-[carbonyl-methoxypolyethyleneglycol-5000]-1,2-distearoyl-sn-glycero-3-phosphoethanolamine may be used, the polyalkylene glycolated lipid is not limited thereto.

<Other Lipid>

Lipids generally used to form liposomes may be used as lipids other than the pH-sensitive cationic lipid according to the present invention, the neutral phospholipid according to the present invention, and the polyalkylene glycol-modified lipid according to the present invention, among the constitution lipids of the lipid nanoparticle according to the present invention. Examples of such lipids include positively or negatively charged phospholipids, sterols, and saturated or unsaturated fatty acids. These may be used alone or in combination of at least two thereof.

Examples of the positively or negatively charged phospholipids include phosphatidylserine, phosphatidylinositol, phosphatidylglycerol, ceramide phosphorylglycerol phosphate, and phosphatidic acid. Examples of the sterols include: sterols derived from animals, such as cholesterol, cholesterol succinic acid, lanosterol, dihydrolanosterol, desmosterol, and dihydrocholesterol; sterols derived from plants (phytosterol), such as stigmasterol, sitosterol, campesterol, and brassicasterol; and sterols derived from microorganisms such as timosterol, and ergosterol.

<Lipid Constitution>

The pH-sensitive cationic lipid according to the present invention, the neutral lipid, and the polyalkylene glycol-modified lipid according to the present invention, constituting the lipid nanoparticle according to the present invention, may each be only one type or at least two types. In the case where at least two types of the pH-sensitive cationic lipid according to the present invention constitute the lipid nanoparticle according to the present invention, the amount of the pH-sensitive cationic lipid according to the present invention means the total amount of lipid molecules corresponding to the pH-sensitive cationic lipid according to the present invention, among lipid molecules constituting the lipid nanoparticle. Similarly, in the case where at least two types of the neutral lipid constitute the lipid nanoparticle according to the present invention, the amount of the neutral lipid according to the present invention means the total amount of lipid molecules corresponding to the neutral lipid according to the present invention, among lipid molecules constituting the lipid nanoparticle. In the case where at least two types of the polyalkylene glycol-modified lipid according to the present invention constitute the lipid nanoparticle according to the present invention, the amount of the polyalkylene glycol-modified lipid according to the present invention means the total amount of lipid molecules corresponding to the polyalkylene glycol-modified lipid according to the present invention, among lipid molecules constituting the lipid nanoparticle.

There is a tendency that the larger the ratio of the pH-sensitive cationic lipid according to the present invention relative to the total amount of lipid molecules (lipid components) constituting the lipid nanoparticle, the smaller the particle size of the lipid nanoparticle, and the higher the encapsulation efficiency of RNP. In addition, there is a tendency that the larger the ratio of the neutral phospholipid according to the present invention relative to the total amount of lipid molecules constituting the lipid nanoparticle, the higher the encapsulation efficiency of RNP. In addition, there is a tendency that the presence of a small amount of the polyalkylene glycol-modified lipid according to the present invention in the lipid molecules constituting the lipid nanoparticle sufficiently decreases the particle size of the lipid nanoparticle, sufficiently enhances the encapsulation efficiency of RNP, and sufficiently enhances the genome editing efficiency. It is preferable that the ratio of the pH-sensitive cationic lipid according to the present invention relative to the total amount of lipids constituting the lipid nanoparticle according to the present invention ([the amount of the pH-sensitive cationic lipid according to the present invention (mol)]/([the amount of the total lipids constituting the lipid nanoparticle (mol)])×100%) be 30% by mol to 50% by mol, the ratio of the neutral phospholipid according to the present invention relative to the total amount of lipids constituting the lipid nanoparticle ([the amount of the neutral phospholipid according to the present invention (mol)]/([the amount of the total lipids constituting the lipid nanoparticle (mol)])×100%) be 20% by mol to 50% by mol, and the amount of the polyalkylene glycol-modified lipid according to the present invention relative to the total amount of lipids constituting the lipid nanoparticle ([the amount of the polyalkylene glycol-modified lipid according to the present invention (mol)]/([the amount of the total lipids constituting the lipid nanoparticle (mol)])×100%) be 1.0% by mol to 4.0% by mol, and more preferable that the ratio of the amount of the pH-sensitive cationic lipid according to the present invention relative to the total amount of lipids constituting the lipid nanoparticle according to the present invention be 40% by mol to 50% by mol, the ratio of the amount of the neutral phospholipid according to the present invention relative to the total amount of lipids constituting the lipid nanoparticle be 20% by mol to 50% by mol, and the ratio of the amount of the polyalkylene glycol-modified lipid according to the present invention relative to the total amount of lipids constituting the lipid nanoparticle be 1.5% by mol to 2.0% by mol, so as to further enhance the genome editing efficiency.

<Surface Modification>

The surface of the lipid nanoparticle according to the present invention may be modified appropriately, as needed.

The blood retention of the lipid nanoparticle according to the present invention can be enhanced by modifying the surface thereof by a hydrophilic polymer or the like. The lipid modified by the modification group may be used as a constitution lipid of the lipid nanoparticle to modify the surface thereof.

In the case where the lipid nanoparticle according to the present invention is prepared, glycophorin, ganglioside GM1, phosphatidylinositol, ganglioside GM3, glucuronic acid derivatives, glutamic acid derivatives, or polyglycerin phospholipid derivatives may be used as lipid derivatives so as to enhance the blood retention. Dextran, pullulan, ficoll, polyvinyl alcohol, styrene-maleic anhydride alternating copolymers, divinyl ether-maleic anhydride alternating copolymers, amylose, amylopectin, chitosan, mannan, cyclodextrin, pectin, or carrageenan may be used in addition to polyalkylene glycol to modify the surface of the hydrophilic polymer so as to enhance the blood retention.

In addition, the surface of the lipid nanoparticle may be modified using a trisaccharide or higher oligosaccharide, for example, so as to promote nuclear translocation of the lipid nanoparticle according to the present invention. Although the type of the trisaccharide or higher oligosaccharide is not particularly limited, an oligosaccharide compound in which approximately 3 to 10 sugar units are bonded may be used, for example, and preferably an oligosaccharide compound in which approximately 3 to 6 sugar units are bonded may be used. Among these, an oligosaccharide compound which is a trimer to hexamer of glucose may be used preferably, and an oligosaccharide compound which is a trimer or tetramer of glucose may be used further preferably. More specifically, isomaltotriose, isopanose, maltotriose, maltotetraose, maltopentaose, or maltohexaose may be preferably used, and among these, maltotriose, maltotetraose, maltopentaose, or maltohexaose, in which glucoses are linked by α1-4 bonds, is further preferably. Maltotriose or maltotetraose is particularly preferable, and maltotriose is most preferable. Although the amount of the modified surface of the lipid nanoparticle by the oligosaccharide compound is not particularly limited, the amount thereof relative to the total amount of lipids is, for example, approximately 1% by mol to 30% by mol, preferably 2% by mol to 20% by mol, and more preferably approximately 5% by mol to 10% by mol.

Although the method of modifying the surface of the lipid nanoparticle by the oligosaccharide compound is not particularly limited, a liposome in which the surface of a lipid nanoparticle is modified with a monosaccharide such as galactose or mannose is known (International Patent Application Publication No. 2007/102481), and therefore the surface modification method disclosed in the publication may be adopted, for example. The entire disclosure of the publication is incorporated herein by reference.

In addition, the lipid nanoparticle according to the present invention may be provided with one property or at least two properties of temperature change sensitivity, membrane permeability, gene expression capability, pH-sensitivity, and the like. An appropriate provision of such properties makes it possible to improve the retention of the lipid nanoparticle in the blood and decrease the ratio of lipid nanoparticles captured by reticuloendothelial tissue such as liver or spleen, and allows the lipid nanoparticle to escape efficiently from the endosome after endocytosis in a target cell and then to translocate into the nucleus, which makes it possible to realize high genome editing activity in the nucleus.

The lipid nanoparticle according to the present invention may be modified by a substance such as an antibody which can specifically bind to a receptor or an antigen on the cell surface to improve the efficiency of delivering substances into the nucleus of cells. It is preferable, for example, that a monoclonal antibody against a biological component which is specifically expressed on a target tissue or organ be placed on the surface of the lipid nanoparticle. The method thereof is described, for example, in STEALTH LIPOSOME (pp. 233-244, issued by CRC Press, Inc., and edited by Danilo Lasic and Frank Martin) or the like. The monoclonal antibody may be bonded on the surface of the membrane of the lipid nanoparticle by containing, as a constitutional component of the lipid nanoparticle, a lipid derivative which can react with a mercapto group in the monoclonal antibody or a fragment thereof (such as Fab fragment, F(ab')2 fragment, or Fab' fragment), such as a lipid derivative having a maleimide structure, such as poly(ethylene glycol)-α-distearoylphosphatidylethanolamine-ω-maleimide, or α-[N-(1, 2-distearoyl-sn-glycero-3-phosphoryl-ethyl)carbamyl)-ω-[3-[2-(2,5-dihydro-2,5-dioxo-1H-pyrol-1-yl) ethanecarboxamide]propyl]-poly(oxy-1,2-ethanedil).

The surface of the lipid nanoparticle according to the present invention may be modified by polypeptides including consecutive plural arginine residues (hereinafter, referred to as "polyarginine"). As the polyarginine, a polypeptide including 4 to 20 consecutive arginine residues may be preferably used, a polypeptide consisting of 4 to 20 consecutive arginine residues may be more preferably used, and octaarginine or the like may be particularly preferably used. The efficiency of delivering RNPs encapsulated in liposomes into cells can be improved by modifying the surface of lipid nanoparticles such as liposomes by polyarginine such as octaarginine (Journal of Controlled Release, 98, pp. 317-323, 2004; International Patent Application Publication No. 2005/32593). The modification of the lipid nanoparticle surface by polyarginine may be readily conducted by the method disclosed in the above-mentioned publications, for example, by using lipid-modified polyarginine, such as stearylated octaarginine, as a constitution lipid of the lipid nanoparticle. The disclosure of the above-mentioned publications and the disclosure of documents cited by the publications are included herein by reference.

[Other Components]

The lipid nanoparticle according to the present invention may further contain one or at least two selected from the group consisting of: antioxidants such as tocopherol, propyl gallate, ascorbyl palmitate, and butylated hydroxytoluene; charged substances, and membrane polypeptides. Examples of the charged substances which can provide a positive charge include: saturated or unsaturated aliphatic amines such as stearylamine and oleylamine; saturated or unsaturated cationic synthetic lipids such as dioleoyl trimethylammonium propane; and cationic polymers. Examples of the charged substances which can provide a negative charge include dicetylphosphate, cholesteryl hemisuccinate, phosphatidylserine, phosphatidylinositol, and phosphatidic acid. Examples of the membrane polypeptides include peripheral membrane polypeptides and integral membrane polypeptides. The amount of these substances is not particularly limited, and may be appropriately determined depending on the intended purpose.

[Lipid Nanoparticle]

The lipid nanoparticle according to the present invention is a lipid membrane structure constituted by lipid components, and RNP is loaded thereon. It is preferable that the ratio of RNP loaded on the lipid nanoparticle according to the present invention relative to the total amount of lipids constituting the lipid nanoparticle ([the amount of RNP (mol)]/([the amount of the total lipids constituting the lipid nanoparticle (mol)])×100%) be $1.8\times10^{-2}$% by mol to $3.6\times10^{-2}$% by mol, from the viewpoint of further increase in the encapsulation ratio of RNP into the lipid nanoparticle.

It is preferable that the average particle size of the lipid nanoparticle according to the present invention be 80 nm or less, more preferably 50 nm or less, even more preferably 40 nm or less, even more preferably 30 nm or less, and particularly preferably 10 nm to 30 nm, since a high delivery efficiency tends to be obtained even in the case where target cells are present at a relatively deep portion within an organism. The average particle size of the lipid nanoparticle means the number-weighted average particle size measured by dynamic light scattering (DLS). The measurement by the dynamic light scattering method can be conducted by a conventional method using a commercially available DLS device or the like.

The polydispersity index (PDI) of the lipid nanoparticle according to the present invention is approximately 0.05 to 0.1, preferably approximately 0.06 to 0.08, and more preferably approximately 0.07. The zeta potential may be within a range of 5.5 mV to 6.0 mV, and preferably approximately 5.8 mV.

Although the form of the lipid nanoparticle according to the present invention is not particularly limited, examples of the form in which the lipid nanoparticles are dispersed in an aqueous solvent include monolayer membrane liposomes, multilayer liposomes, spherical micelles, and amorphous layered structures. The lipid nanoparticle according to the present invention is preferably a monolayer membrane liposome or a multilayer liposome.

[Preparation Method]

The preparation method of the lipid nanoparticle according to the present invention is not particularly limited, and an arbitrary method available to a person skilled in the art may be adopted. For example, a lipid membrane is formed by dissolving all lipid components in an organic solvent such as chloroform, followed by evaporating to dryness under reduced pressure using an evaporator or spray drying using a spray dryer, and then an aqueous solvent containing RNP and the like is added to the resultant dried mixture, followed by emulsifying the resultant mixture by an emulsifier such as a homogenizer, an ultrasonic emulsifier, or a high-pressure injection emulsifier. The liposomes may also be prepared by a well-known preparation method thereof, such as a reverse-phase evaporation method. In the case where the size of the lipid nanoparticle is desired to be controlled, extrusion (extrusion filtration) may be conducted under high pressure using a membrane filter, the pore size of which is uniform.

The lipid nanoparticle according to the present invention may be prepared by alcohol dilution using a flow channel. Although a three-dimensional micro mixer-embedded micro flow channel that can achieve instantaneous mixing of two liquids may be used as the flow channel used to prepare the lipid nanoparticle, a flow channel structure having a simple two-dimensional structure in which baffles (baffle plates) having a fixed width relative to the flow channel width are alternately disposed from two side faces in a micro-sized flow channel through which feedstock solutions are flowed, as disclosed in Patent Document 1, is preferably used because a nano-sized lipid particle formation system having high particle size controllability can be formed.

Specifically, it is preferable that a flow channel structure as shown in FIG. 1A (hereinafter, may be referred to as "flow channel structure according to the present invention") be used. In the upstream side (left side of the drawing), a first introducing passage 10 configured to introduce the first fluid and a second introducing passage 20 configured to introduce the second fluid are mutually independent and join together while each having fixed lengths to form a single dilution flow channel 30. The dilution flow channel 30 has a two-dimensionally bent-flow channel portion 50 in at least a portion thereof, and the bent-flow channel portion 50 is configured such that, in the case where the axial direction of the dilution flow channel upstream therefrom or the extending direction thereof is defined as the X direction, the width direction of the dilution flow channel that perpendicularly intersects with the X direction is defined as the Y direction, and the flow channel width of the dilution flow channel upstream therefrom is defined as $y_0$, and at least two structural elements 40 which define flow channel width of the dilution flow channel by alternately protruding from two side surfaces, facing each other in the Y direction, of the dilution flow channel towards the center of the flow channel at a fixed height $h_1, h_2, \ldots$ of $\frac{1}{2}y_0$ or more and less than $1_{y0}$ in an approximate Y direction (approximate +Y direction or approximate $-Y$ direction) and at a fixed width $X_1, X_2, \ldots$ in the X direction are provided at fixed intervals $d_1, d_2, \ldots$. In other words, the flow channel width $y_1, y_2, \ldots$ of the dilution flow channel is restricted to $\frac{1}{2}y_0$ or less, and particularly, $\frac{1}{2}y_0$ or less to $\frac{1}{40}y_0$ or more between a fixed width $x_1, x_2, \ldots$ in the X direction at the site where the structural elements 40 are present.

Furthermore, although the flow channel structure according to the present invention conceptually has a form in which roughly rectangular baffles are alternately disposed from two side faces in the micro-sized flow channel as exemplified in FIG. 1A and explained above, the flow channel structure is not limited in actuality to that composed by arranging separate baffles in a flow channel in this manner. In other words, there are no particular limitations on the configuration of the structural elements 40 provided that a flow channel of a similar form is formed so as to correspond to the flow channel formed by arranging such baffles, and, for example, a flow channel having a two-dimensional structure in which the walls of the flow channel structure are bent in a prescribed shape (while maintaining a nearly fixed wall thickness) while being integrally formed to bend and expand so as to be defined as previously described may be formed such that the structural elements 40 are constituted in the manner previously described, and such an aspect is naturally included in the flow channel structure according to the present invention. The flow channel having a two-dimensional structure can be formed relatively easily by injection molding, cast molding or molding using a three-dimensional printer using, for example, a thermoplastic resin, a thermosetting resin, an ultraviolet curable resin or a metal or vitreous material.

Although the flow channel width $y_0$ of the dilution flow channel 30 after the first introducing passage 10 and the second introducing passage 20 join together is partly influenced by the particle size of the nano-sized lipid particles to be formed, the flow channel width $y_0$ is representatively approximately 20 μm to 1000 and more preferably 100 μm to 200 μm. It is a condition required to some extent that a lipid solution be diluted with a dilution medium at the flow channel width $y_0$ within the above-mentioned range, so as to obtain a lipid particle having a particle size within a range of a desired nano-size, specifically, for example, approximately 10 nm to 100 nm.

The height $h_1, h_2 \ldots$ (the length in the Y direction) of each structural element 40, relative to the flow channel width $y_0$ of the dilution flow channel 30 on the upstream side therefrom, is $\frac{1}{2}y_0$ or more and less than $1y_0$, preferably $\frac{1}{2}y_0$ to $\frac{39}{40}y_0$, and more preferably $\frac{1}{2}y_0$ to $\frac{3}{4}y_0$, and the presence of each structural element 40 decreases the flow channel width $y_1, y_2, \ldots$ from the flow channel width $y_0$ of the dilution flow channel 30 on the upstream side therefrom to a width of less than $\frac{1}{2}y_0$ and greater than 0. The respective height $h_1, h_2, \ldots$ of the plurality of structural elements 40 provided in the bent flow channel site 50 is not necessarily required to be identical to each other, and may be different from each other provided that the above-mentioned prescribed conditions are satisfied. The flow channel widths $y_1, y_2, \ldots$ formed as a result thereof may also be different from each other. For example, an aspect may be employed in which each width $h_1, h_2, \ldots$ of each structural element 40 gradually becomes longer and each flow channel width $y_1, y_2, \ldots$ becomes narrower in the downstream direction. The efficiency of molecular diffusion improves as a result of the height $h_1, h_2, \ldots$ (length in the Y direction) of each structural element 40 being a prescribed height and the flow channel widths $y_1, y_2, \ldots$ of the sites where these structural elements 40 are present being held to a width of less than $\frac{1}{2}y_0$.

Although the respective height $h_1, h_2, \ldots$ of the structural elements 40 is influenced by other conditions such as the size of the lipid particles to be obtained, the number of structural elements 40, the width $x_1, x_2, \ldots$ (length in the X direction) of each mixer structural element 40 or the distance $d_1, d_2, \ldots$ between each adjacent structural element 40, and there are no particular limitations thereon, in the case where, for example, the flow channel width $y_0$ of the upstream dilution flow channel is 200 μm, the respective height $h_1$, $h_2, \ldots$ of the structural elements 40 is preferably 100 μm or more and less than 200 μm, specifically. Thus, the flow channel width $y_1, y_2, \ldots$ at the location where each structural element 40 is present is approximately less than 100 μm, which is less than $\frac{1}{2}y_0$ and greater than 0.

In addition, although the width $x_1, x_2, \ldots$ (length in the X direction) of each structural element 40 is influenced by other conditions such as the size of the lipid particles to be obtained, the number of the structural elements 40, the height $h_1, h_2, \ldots$ (length in the Y direction) of each structural element 40, or the interval $d_1, d_2, \ldots$ between each adjacent structural element 40, the width $x_1, x_2, \ldots$ (length in the X direction) of each structural element 40 relative to the flow channel width $y_0$ of the upstream dilution flow channel is preferably a length of about $\frac{1}{10}y_0$ or more and $5y_0$ or less. Specifically, in the case where, for example, the flow channel width $y_0$ of the upstream dilution flow channel is 20 μm to 1000 μm, and typically 200 μm, the width $x_1, x_2, \ldots$ is desirably about 20 μm to 1000 μm. The respective width $x_1, x_2, \ldots$ of the structural elements 40 is not necessarily required to be identical to each other, and may be different from each other provided that the above-mentioned prescribed conditions are satisfied. For example, an aspect may be employed in which the width $x_1, x_2, \ldots$ gradually becomes longer in the downstream direction.

In addition, although the interval $d_1, d_2, \ldots$ between each adjacent structural element 40 is influenced by other conditions such as the size of the lipid particles to be obtained, the number of the structural elements 40, the height $h_1, h_2, \ldots$ (length in the Y direction) of each structural element 40 or the width $x_1, x_2, \ldots$ (length in the X direction) of each structural element 40, the interval $d_1, d_2, \ldots$ between each adjacent structural element 40, relative to the flow channel width $y_0$ of the upstream dilution flow channel is preferably a length of about $\frac{1}{10}y_0$ to $5y_0$. Specifically, in the case where, for example, the flow channel width $y_0$ of the upstream dilution flow channel is 20 μm to 1000 μm, and typically 200 μm, the interval $d_1, d_2, \ldots$ between each adjacent structural element 40 is preferably about 20 μm to 1000 μm. The interval $d_1, d_2, \ldots$ between each adjacent structural element 40 is not necessarily required to be identical to each other and may be different from each other provided that the above-mentioned prescribed conditions are satisfied. For example, an aspect may be employed in which the interval $d_1, d_2, \ldots$ gradually becomes narrower in the downstream direction.

Furthermore, in the flow channel structure according to the present invention, in the case where the axial direction of the upstream dilution flow channel or the extending direction thereof is defined as the X direction and the width direction of the dilution flow channel that perpendicularly intersects with the X direction is defined as the Y direction, although each structural element 40 is alternately extended from two sidewalls towards the center of the flow channel in an approximate Y direction (approximate +Y direction or approximate −Y direction) and has wall surfaces approximately at a right angle relative to the flow channel direction (X direction), the angle being not necessarily required to be 90° exactly, an effective configuration can be obtained even if inclined to a certain degree, and there are no particular limitations thereon, but the angle is specifically allowed to be within a range of about 30° to 150°, more preferably 40° to 140° and particularly preferably 80° to 100°. Although the shape of the corner portion of each structural element 40 in the center side of the flow channel is permitted to be rounded to a certain degree, and there are no particular limitations thereon, there are cases in which rounding of, for example, R50 µm or less, and more preferably R20µm) or less is permitted. However, the tolerances are preferably as small as possible, in terms of obtaining uniform nano-sized lipid particles having a higher degree of controllability. In addition, although the X direction, which is the axial direction of the upstream dilution flow channel in the flow channel structure or the extending direction thereof, is represented with a straight line for the sake of convenience in the embodiment shown in FIG. 1A, the X direction merely indicates the axial direction of the dilution flow channel, is not limited to the straight line in actuality, and may also, for example, be curved at a certain curvature. Furthermore, in such cases, the Y direction, which is the width direction of the dilution flow channel that perpendicularly intersects with the X direction, indicates a direction perpendicular to the X direction at a site of the unit length thereof.

Since the flow channel structure according to the present invention is a flow channel structure having a two-dimensional structure as mentioned above, the size in the depth direction of the flow channel thereof (the paper thickness-direction in FIG. 1A) is not particularly limited, but the size is, for example, approximately 10 µm to 1000 µm, and preferably approximately 50 µm to 200 µm.

There is no particular limitation on the flow channel available to prepare the lipid nanoparticle according to the present invention by an alcohol dilution method, provided that the dilution flow channel 30 in the flow channel structure shown in FIG. 1A allows the generation of three-dimensional flow. For example, the flow channel structure according to the present invention may be a chaotic micro mixer (staggered herringbone mixer) (Non-Patent Document 8) which generates chaotic flow by grooves or microspikes formed on the wall surface of the flow channel in at least a portion of the dilution flow channel 30, instead of the two-dimensionally bent-flow channel portion 50.

In the case where the first introducing passage 10 configured to introduce the first fluid and the second introducing passage 20 configured to introduce the second fluid join together while each having fixed lengths to form a single dilution flow channel in the flow channel structure according to the present invention, as shown in FIG. 1A, a lipid solution in which the lipid components are dissolved in ethanol is introduced from the first introducing passage, and an aqueous solution containing Cas9 protein, crRNA, tracrRNA and ssON (RNP-containing aqueous solution) is introduced from the second introducing passage. In the dilution flow channel, the lipid solution is diluted with the RNP-containing aqueous solution to prepare RNP-loaded lipid nanoparticles.

The flow channel structure according to the present invention includes plural introducing passages which are mutually independent and join together while each having fixed lengths to form a single dilution flow channel, and thus the flow channel structure may include three introducing passages. In the case where the flow channel structure according to the present invention includes three introducing passages, the first introducing passage, the second introducing passage, and the third introducing passage may join together while each having fixed lengths to form a single dilution flow channel such that the first fluid introduced from the first introducing passage contacts the third fluid introduced from the third introducing passage before joining the second fluid introduced from the second introducing passage.

Figure 1B:
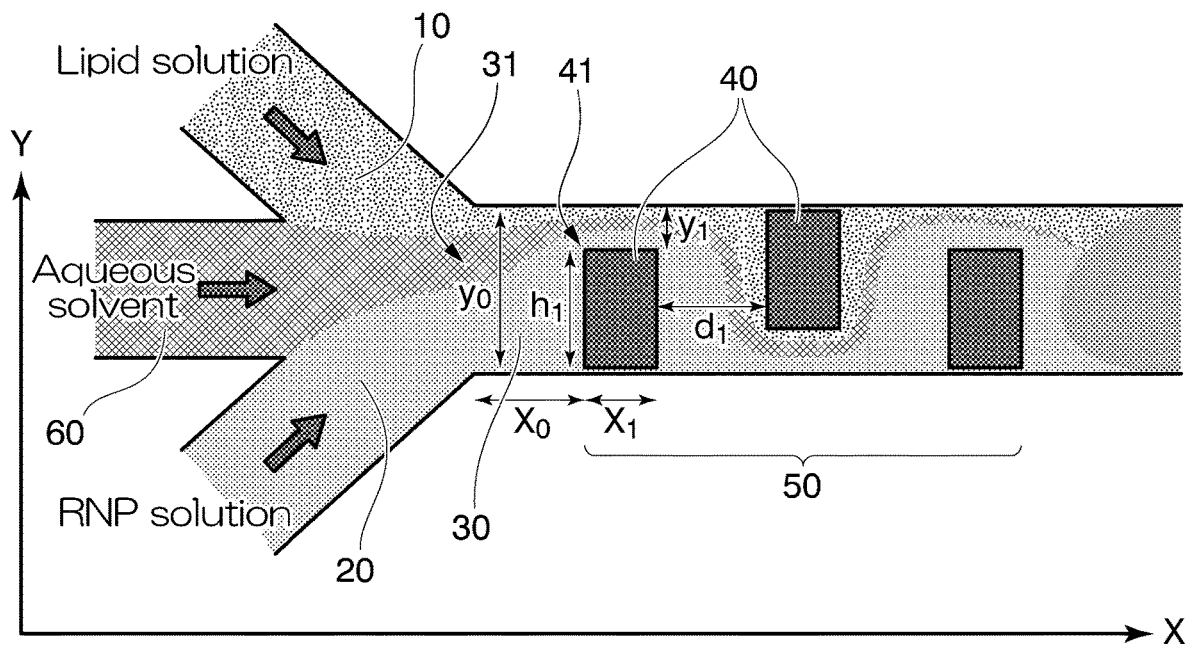
FIG. 1B is a drawing schematically showing the structure of the flow channel in one embodiment available to prepare the lipid nanoparticle according to the present invention.

In the case where, for example, introducing passages, the distance between which to the confluence in the dilution flow channel 30 is the longest, are defined as the first introducing passage 10 and the second introducing passage 20, and the remaining introducing passage is defined as the third introducing passage 60, as shown in FIG. 1B, a lipid solution in which the lipid components are dissolved in ethanol is introduced from the first introducing passage 10, an RNP-containing aqueous solution is introduced from the second introducing passage 20, and an aqueous solvent used to prepare the RNP-containing aqueous solution is introduced from the third introducing passage 60. The lipid solution introduced from the first introducing passage 10 firstly joins the aqueous solvent introduced from the third introducing passage 60, and then joins the RNP-containing aqueous solution introduced from the second introducing passage 20. Since the direct contact of the RNP-containing aqueous solution with the lipid solution which is a highly concentrated ethanol solution can be avoided, aggregation of the protein in the RNP-containing aqueous solution by the highly concentrated ethanol in the dilution flow channel 30, particularly near an inlet thereof, can be suppressed.

The dilution in the flow channel structure according to the present invention depends on the molecular diffusion. The faster the dilution rate of the lipid solution serving as feedstock, the smaller the size of lipid particles formed becomes. Thus, the dilution rate of the feedstock solution can be controlled by adjusting the width, the length and the arrangement of the structural elements (baffles), thereby making it possible to form lipid nanoparticles having a higher degree of particle size controllability than in the prior art.

The RNP-containing aqueous solution can be prepared by dissolving the Cas9 protein, crRNA, tracrRNA and ssON in the aqueous solvent. The aqueous solvent is not particularly limited, provided that the aqueous solvent is an aqueous solvent which allows RNP to be mixed with the lipid solution while maintaining the genome editing activity, and allows the formed lipid nanoparticles to disperse stably. Examples of the aqueous solvent include: buffers such as phosphate buffer, citrate buffer, and phosphate-buffered saline; physiological saline, and cultivation medium. The aqueous solvent (dispersion medium) may further contain: a monosaccharide, such as glucose, galactose, mannose, fructose, inositol, ribose, or xylose sugar; a disaccharide, such as lactose, sucrose, cellobiose, trehalose, or maltose; a trisaccharide, such as raffinose or melezitose; a polysaccharide such as cyclodextrin; a sugar alcohol, such as erythritol, xylitol, sorbitol, mannitol, or maltitol; or a polyhydric alcohol, such as glycerine, diglycerine, polyglycerine, propylene glycol, polypropylene glycol, ethylene glycol, diethylene glycol, triethylene glycol, polyethylene glycol, ethylene glycol monoalkyl ether, diethylene glycol monoalkyl ether, or 1,3-butylene glycol.

In the case where the pH of the RNP-containing aqueous solution is low, the genome editing activity of the lipid nanoparticle loaded with the formed RNP may decrease. Thus, the pH of the RNP-containing aqueous solution is preferably at least 5.0, more preferably within a range of 5.0 to 8.5, even more preferably within a range of 5.0 to 8.0, and even more preferably within a range of 5.0 to 7.5. Alternatively, the pH of the RNP-containing aqueous solution is preferably at least 6, more preferably within a range of 6 to 8.5, even more preferably within a range of 6 to 8, and even more preferably within a range of 6 to 7.5.

The flow rate ratio of the lipid solution and the RNP-containing aqueous solution affects the dilution rate of the lipid solution, thereby affecting the size of the resultant lipid particle. When the lipid nanoparticle according to the present invention is prepared, the ratio of the flow rate of the RNP-containing aqueous solution to the flow rate of the lipid solution is preferably at least 7, more preferably 7 to 10, and even more preferably 7 to 9, from the viewpoint of the manufacturability of lipid nanoparticles, in which the average particle size is sufficiently small and the efficiency of incorporation into target cells is high.

There is no particular limitation on the total flow quantity of the lipid solution and the RNP-containing aqueous solution, and the total flow quantity may be adjusted appropriately within a range of 1 µL/minute to 100 mL/minute. When the lipid nanoparticle according to the present invention is prepared, the total flow quantity of the lipid solution and the RNP-containing aqueous solution is preferably within a range of 50 µL/minute to 1 mL/minute, more preferably within a range of 50 µL/minute to 800 µL/minute, even more preferably within a range of 50 µL/minute to 600 µL/minute, and even more preferably 50 µL/minute to 500 µL/minute.

The lipid nanoparticle according to the present invention is a carrier that delivers RNP which allows genome editing into target cells. The genome editing may be conducted by introducing the lipid nanoparticles according to the present invention into target cells. In the case where the target cells are culture cells, the lipid nanoparticles according to the present invention are added to culture medium. In the case where the target cells are cells in the animal body, the lipid nanoparticles according to the present invention are administered to the animal. Although there is no particular limitation on the administration route, parenteral administration, such as intravenous administration, enteral administration, intramuscular administration, subcutaneous administration, transdermal administration, nasal administration, or pulmonary administration is preferable.

There is no particular limitation on the animal to be administered with the lipid nanoparticle according to the present invention, and the animal may be human or an animal other than human. Examples of the non-human animal include: mammals such as cows, pigs, horses, sheep, goats, monkeys, dogs, cats, rabbits, mice, rats, hamsters, and guinea pigs; and birds such as chickens, quails, and ducks.

EXAMPLES

Although the present invention will be explained below in further detail by way of examples, the present invention is not limited to the following examples.

Reference Example 1

Conditions for preparing RNP-loaded lipid nanoparticles were investigated using a manufacturing device including a flow channel structure as shown in FIG. 1A. Specifically, the pH of buffer in which RNP was dissolved, the flow rate ratio (FRR) of an RNP solution to ethanol, and the total flow rate (TFR) of ethanol and the RNP solution were investigated.

Figure 2:
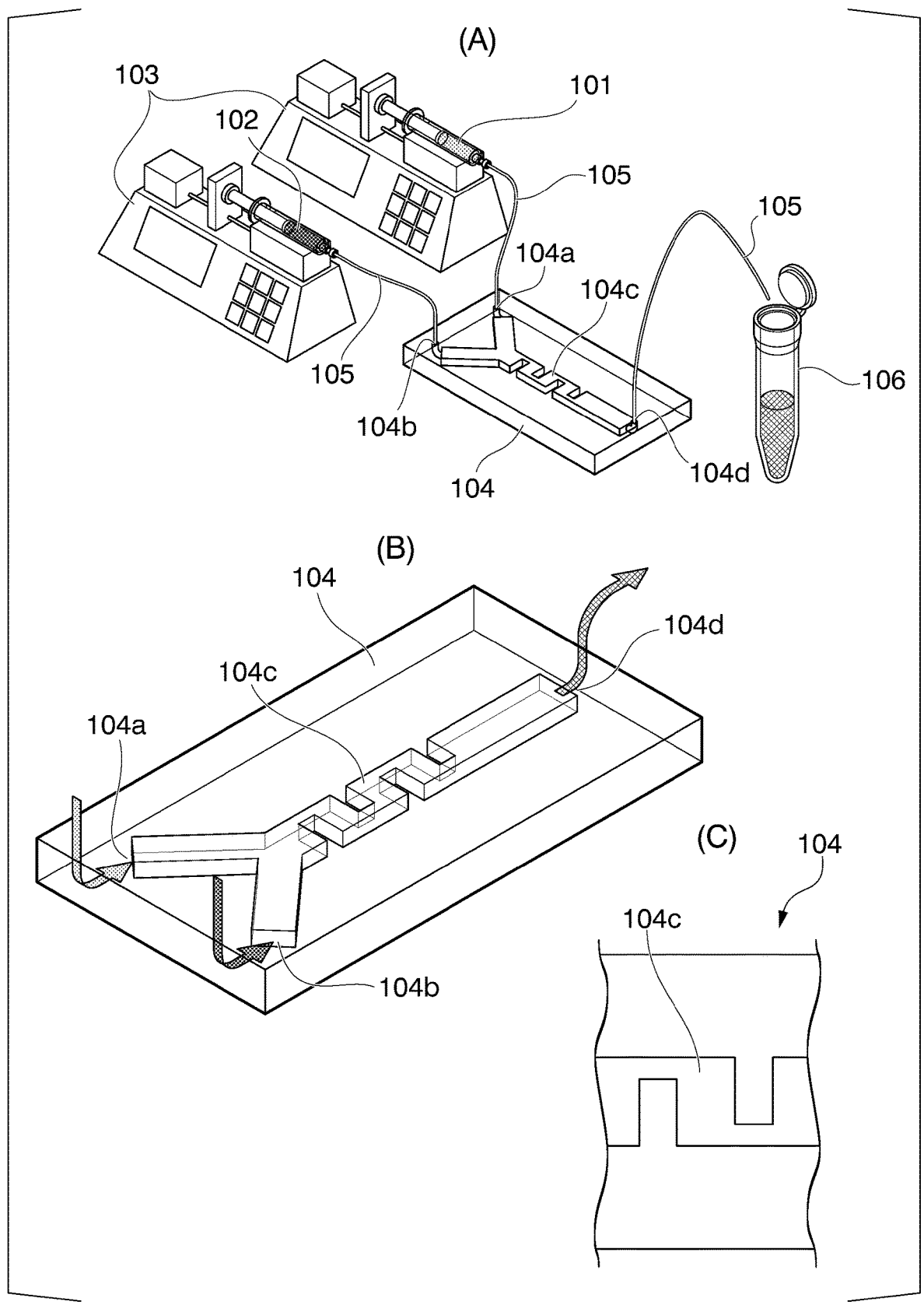
FIG. 2 is a schematic drawing of the flow channel structure used in Reference Example 1 and Example 1.

A manufacturing device actually used is schematically shown in FIG. 2. FIG. 2(A) is a schematic drawing of the entire structure, FIG. 2(B) is a perspective drawing of a mixer-embedded micro flow channel (flow channel structure), and FIG. 2(C) is a partially-enlarged view of a dilution flow channel 104c. As shown in FIG. 2(A), a syringe 101 in which a lipid solution was put and a syringe 102 in which an RNP solution was put were each placed in flow quantity control devices 103 and connected via tubes 105 at an inlet 104a of a first introducing passage and an inlet 104b of a second introducing passage in a mixer-embedded micro flow channel 104, and a collection container 106 configured to collect the produced lipid nanoparticles was connected with an outlet 104d of the dilution flow channel 104c via a tube 105.

Ethanol was used instead of the lipid solution to exclude the effects of lipid in the investigation of the conditions. A solution (RNP solution) in which a Cas9 protein derived from *Streptococcus pyogenes* (160 kDa) (product name: "Alt-R S.p. Cas9 Nuclease V3", manufactured by Integrated DNA technologies, Inc.), a crRNA (SEQ. ID. NO. 2, 36 base length, the $1^{st}$ to $20^{th}$ region of the base sequence thereof was complementary to the target sequence) including a base sequence complementary to the target sequence (SEQ. ID. NO. 1, 20 base length) in GFP (green fluorescent protein) gene, and a tracrRNA (SEQ. ID. No. 3, 67 base length) were dissolved in a buffer at a molar ratio of 1:1:1 was used as the RNP solution. The crRNA and the tracrRNA were obtained by amplifying by PCR using the genomic DNA of GFP-stably expressing HeLa (HeLa-GFP) cells as a template. MES buffer (20 mM MES, 50 mM NaCl, pH 6.0) was used as a buffer having a pH of 6, and citrate buffer (20 mM citric acid, 50 mM NaCl, pH 4.0, 5.0, or 5.5) was used as a buffer having a pH of 4.0, 5.0, or 5.5.

The RNP solution and ethanol were each sent into a micro flow channel of a manufacturing device shown in FIG. 2 and a solution exhausted from a dilution flow channel was collected to lead the collected solution to a dialysis membrane (MWCO: 12,000 to 14,000), followed by conducting dialysis in PBS(−) at 4° C. for 2 hours or more to replace the buffer and remove alcohol. The concentration of the Cas9 protein in the RNP solution was quantified by fluorescamine after the dialysis, and then the RNP solution was mixed with a double-stranded DNA (dsDNA) (SEQ. ID. NO. 4, 0.25 pmol) including the target sequence such that the amount based on the Cas9 protein became 2 or 5 equivalents (molar ratio), followed by reacting the mixture at 37° C. for 1 hour. After the reaction, the reactant solution was subjected to agarose electrophoresis to evaluate the DNA cleavage efficiency. A dsDNA unmixed with RNP was used as a negative control, and a sample obtained by adding an RNP unintroduced into the micro flow channel to a dsDNA was used as a positive control. The relative cleavage activity of each sample was calculated by setting the cleavage activity of a sample prepared by adding 5 equivalents of RNP relative to the target dsDNA as the positive control as 1. The quantitative analysis was conducted using an image analysis software of Image J.

The RNP solution was prepared using a buffer having a pH of 6.0, and effects of TFR were investigated at FRR of 9.0 and at TFR of 50 µL/minute to 500 µL/minute. The results are shown in Table 1. In the table, "N.C." indicates the result of the negative control and "P.C." indicates the result of the positive control. As shown in Table 1, a similar degree of cleavage activity to that of the positive control was confirmed at every total flow rate, and no effects on DNA cleavage activity by the total flow rate were confirmed, and therefore the following experiments were conducted at 500 µL/minute to realize a higher mixing rate.

TABLE 1

| | TFR (µL/minute) | | | | | | | | | |
|---|---|---|---|---|---|---|---|---|---|---|
| | N.C. | P.C. | | 50 | | 100 | | 250 | | 500 |
| RNP/dsDNA (mol) | — | 2 | 5 | 2 | 5 | 2 | 5 | 2 | 5 | 2 | 5 |
| Relative cleavage activity | 0.00 | 0.39 | 1.00 | 0.41 | 1.17 | 0.35 | 1.28 | 0.37 | 1.03 | 0.40 | 0.95 |

The RNP solution was prepared using a buffer having a pH of 6.0, and effects of FRR were investigated at TFR of 500 µL/minute and at FRR of 3.0 to 9.0. The results are shown in Table 2. As shown in Table 2, the decrease in DNA cleavage activity accompanying the decrease in FRR within a range of 5.0 or less was confirmed. In contrast, a similar degree of activity to that of the positive control was confirmed at FRR of 7.0 or more and thus no effects of sending the solution into the micro flow channel were confirmed. In view of the results, the following experiments were conducted at FFR of 9.0.

TABLE 2

| | FRR | | | | | | | | | |
|---|---|---|---|---|---|---|---|---|---|---|
| | N.C. | P.C. | | 3 | | 5 | | 7 | | 9 |
| RNP/dsDNA (mol) | — | 2 | 5 | 2 | 5 | 2 | 5 | 2 | 5 | 2 | 5 |
| Relative cleavage activity | 0.00 | 0.62 | 1.00 | 0.05 | 0.17 | 0.32 | 0.68 | 0.55 | 1.08 | 0.56 | 0.75 |

Effects of the pH of the RNP solution were investigated at TFR of 500 µL/minute and at FRR of 9.0, using a buffer having a pH of 4.0 to 6.0 to prepare the RNP solution. The results are shown in Table 3. As shown in Table 3, a similar degree of DNA cleavage activity to that of the positive control was maintained at pH of 6.0, whilst a significant decrease in DNA cleavage activity accompanying the decrease in pH within the range of 5.5 or less was confirmed. In view of the results, the following experiments were conducted using a buffer having a pH of 6.0 to prepare the RNP solution.

TABLE 3

| | pH | | | | | | | | | |
|---|---|---|---|---|---|---|---|---|---|---|
| | N.C. | P.C. | | 6.0 | | 5.5 | | 5.0 | | 4.0 |
| RNP/dsDNA (mol) | — | 2 | 5 | 2 | 5 | 2 | 5 | 2 | 5 | 5 |
| Relative cleavage activity | 0.00 | 0.35 | 1.00 | 0.47 | 1.14 | 0.18 | 0.45 | 0.13 | 0.38 | 0.11 |

Reference Example 2

Figure 3:
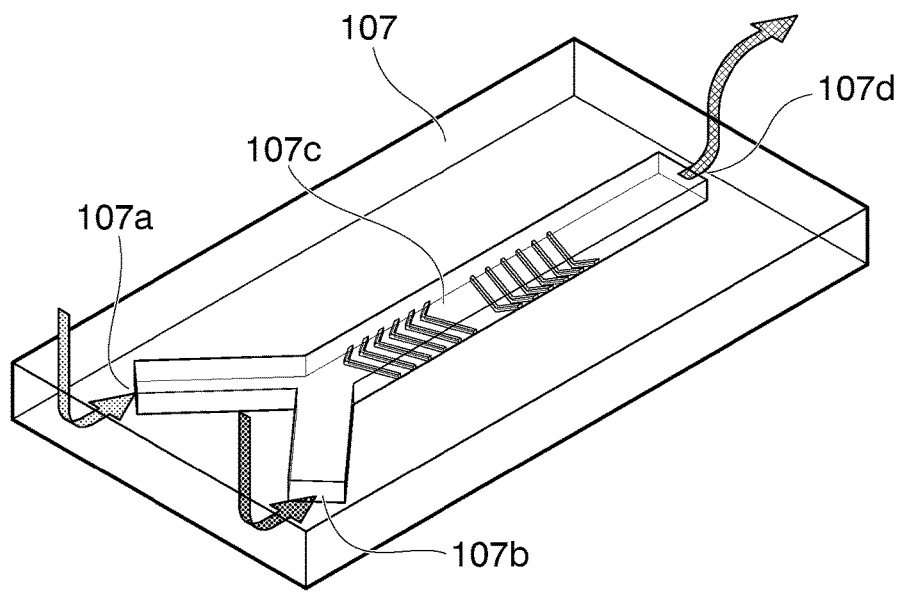
FIG. 3 is a schematic drawing of the flow channel structure used in Reference Example 2.
Figure 3:
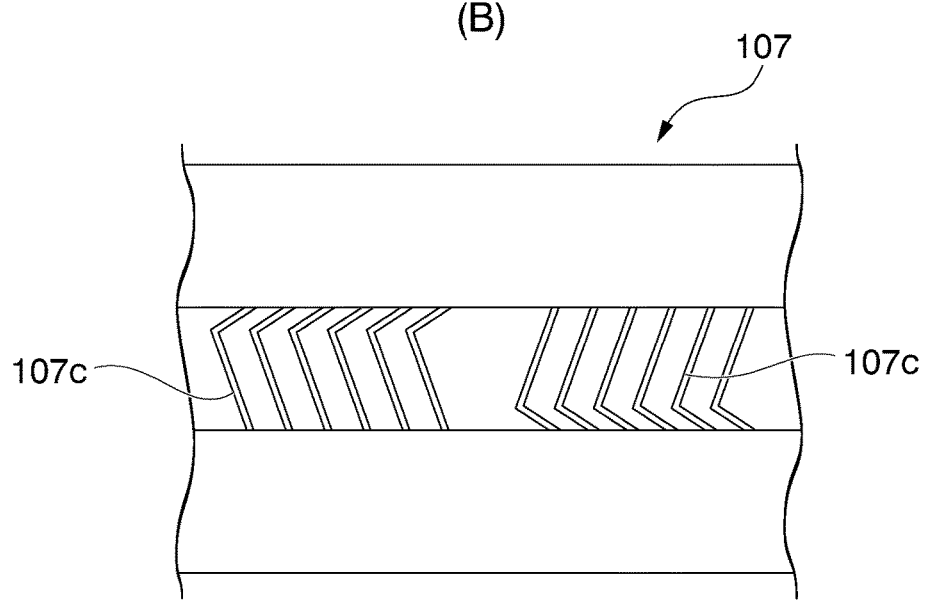

It was investigated whether the lipid nanoparticle according to the present invention could be prepared using a manufacturing device equipped with a chaotic mixer. Specifically, the pH of the buffer in which an RNP was dissolved, the flow rate ratio (FRR) of the RNP solution to ethanol, and the total flow rate (TFR) of ethanol and the RNP solution were investigated. The lipid nanoparticle was prepared using a manufacturing device in which the mixer-embedded micro flow channel 104 was the chaotic mixer-embedded micro flow channel 107 shown in FIG. 3 from the manufacturing devices used in Reference Example 1. FIG. 3(A) is a perspective drawing of the chaotic mixer-embedded micro flow channel (flow channel structure), and FIG. 3(B) is a partially-enlarged view of a dilution flow channel 107c.

Ethanol was used instead of a lipid solution so as to exclude the effects of lipid, and a solution obtained by dissolving a Cas9 protein (160 kDa) derived from *Streptococcus pyogenes*, a crRNA (SEQ. ID. NO. 2, 36 base length) including a base sequence complementary to the target sequence (SEQ. ID. NO. 1, 20 base length) in the GFP gene, and tracrRNA (SEQ. ID. NO. 3, 67 base length) in a buffer at a molar ratio of 1:1:1 was used as an RNP solution to investigate conditions, in a similar manner to that of Reference Example 1. MES buffer (20 mM MES, 50 mM NaCl, pH 6.0) was used as a buffer having a pH of 6 to 6.6, and citrate buffer (20 mM citric acid, 50 mM NaCl, pH 5.5) was used as a buffer having a pH of 5.5.

The RNP solution and ethanol were sent into the micro flow channel of the manufacturing device shown in FIG. 3 at TFR of 500 µL/minute and at FRR of 9 to collect the RNP solution exhausted from the dilution flow channel, followed by subjecting the collected solution to dialysis in a similar manner to that of Reference Example 1. The RNP solution after the dialysis was mixed with dsDNA such that the amount based on the Cas9 protein became 5 equivalents (molar ratio) in a similar manner to that of Reference Example 1, followed by reacting the mixture at 37° C. for 1 hour to evaluate the DNA cleavage activity. The relative cleavage activity of each sample was calculated by setting the cleavage activity of the positive control prepared by adding 5 equivalents of RNP to the target dsDNA as 1. The results are shown in Table 4. A similar degree of DNA cleavage activity to that of the positive control was maintained at pH of 6.0, whilst a significant decrease in DNA cleavage activity was confirmed at pH of 5.5, in a similar manner to that of Reference Example 1.

TABLE 4

| | pH | | | | |
|---|---|---|---|---|---|
| | 5.5 | 6.0 | 6.2 | 6.4 | 6.6 |
| Relative cleavage activity | 0.46 | 1.01 | 0.93 | 0.95 | 0.88 |

The RNP solution was prepared using a buffer having a pH of 6.0, and effects of FRR were similarly investigated at TFR of 500 μL/minute and at FRR of 5.0, 7.0, or 9.0. Results are shown in Table 5. The DNA cleavage activity was slightly low at FRR of 5.0, whilst a similar degree of DNA cleavage activity to that of the positive control was confirmed at FRR of 7.0 or more, and thus no effects of sending the solution into the micro flow channel were confirmed.

TABLE 5

| | FRR | | |
|---|---|---|---|
| | 5 | 7 | 9 |
| Relative cleavage activity | 0.83 | 0.94 | 1.00 |

It became apparent from the results that the lipid nanoparticle according to the present invention could be prepared using the manufacturing device shown in FIG. 3 under the same conditions as those of the case when the manufacturing device shown in FIG. 2 was used. In other words, it was suggested that the selectivity of the mixer structure was low to prepare the lipid nanoparticle according to the present invention.

Example 1

Lipid nanoparticles loaded with RNPs that allow knockout of the GFP gene, the lipid constitutions thereof being different from each other, were prepared to investigate the GFP knockout activity in HeLa-GFP cells. In addition, lipid nanoparticles loaded with RNPs that allow knockin to replace the GFP gene to the BFP (blue fluorescent protein) gene, the lipid constitutions thereof being different from each other, were prepared to investigate the GFP knockin activity in HeLa-GFP cells. The lipid nanoparticles were prepared using the manufacturing device used in Reference Example 1.

CL4H6 (pKa: 6.25 or less, Patent Document 2) was used as a pH-sensitive cationic lipid, and 1,2-distearoyl-sn-glycero-3-phosphatidylcholine (DSPC) or 1,2-dioleoyl-sn-glycero-3-phosphatidylethanolamine (DOPE) was used as a neutral phospholipid as lipids constituting the lipid nanoparticles. Cholesterol (chol) and 1,2-dimyristoyl-rac-glycero-3-methoxypolyethylene glycol-2000 (PEG-DMG) were used as additional lipids.

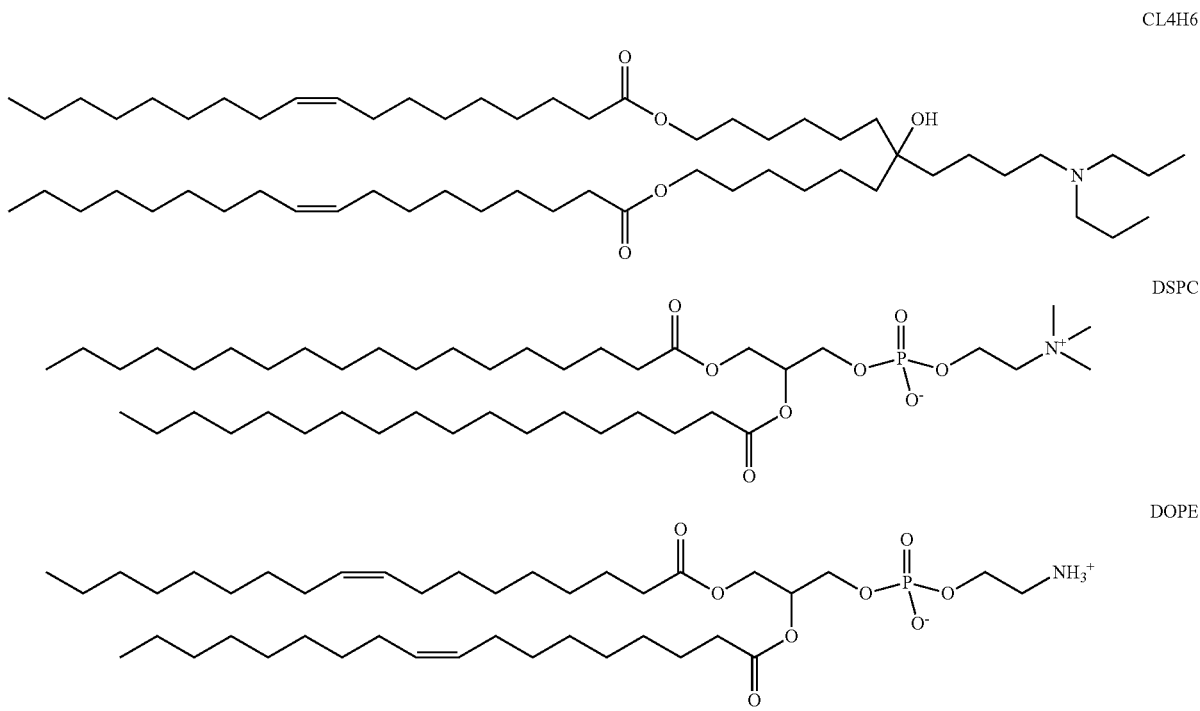

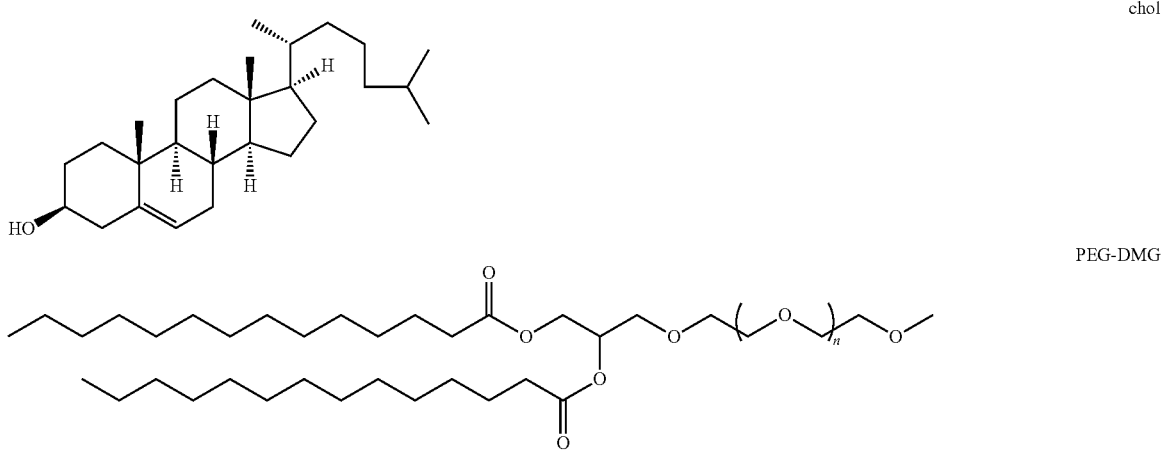

chol

PEG-DMG

Five types of lipid components having lipid constitutions shown in Table 6 were used to prepare the lipid nanoparticles.

TABLE 6

| | Lipid constitution (% by mol) |
|---|---|
| 10% (DSPC) | CL4H6/chol/DSPC/PEG-DMG = 50/40/10/2.5 |
| 20% (DSPC) | CL4H6/chol/DSPC/PEG-DMG = 50/30/20/2.5 |
| 10% (DOPE) | CL4H6/chol/DOPE/PEG-DMG = 50/40/10/2.5 |
| 20% (DOPE) | CL4H6/chol/DOPE/PEG-DMG = 50/30/20/2.5 |
| 0% | CL4H6/chol/DSPC/PEG-DMG = 50/50/0/2.5 |

The same Cas9 protein, crRNA, and tracrRNA, as those used in Reference Example 1 were used.

RNP available to conduct knockout of GFP was prepared using DNA having a 132-base length (SEQ. ID. NO. 5, the $68^{th}$ to $87^{th}$ region thereof consisted of a base sequence identical to the target sequence) composed of a base sequence identical to a partial region of genomic DNA including the target sequence (SEQ. ID. NO. 1) as ssON available to conduct knockout of GFP.

RNP available to conduct knockin to replace GFP with BFP was prepared using DNA (SEQ. ID. NO. 6) in which a mutation was introduced into 3 bases (the $65^{th}$, $67^{th}$ and $72^{th}$ bases) of the ssON used to conduct knockout as ssON available to conduct knockin of BFP. In the case where the introduction of the mutant sequence allows the homology-dependent repair (HDR) pathway to work, amino acids (threonine-tyrosine-glycine) constituting a fluorophore of GFP were replaced with amino acids (serine-histidine-glycine) constituting a fluorophore of BFP.

<Measurement of GFP Knockout Activity>

The RNP solution was prepared by dissolving 160 nM of Cas9 protein, 160 nM of crRNA, 160 nM of tracrRNA, and 160 nM of ssON in the buffer having a pH of 6.0, which was used in Reference Example 1, and then RNP solution was put into a syringe 102 connected with an inlet 104b of the second introducing passage. An ethanol solution containing lipids (the total amount of lipids: 8.20 mM) was put into a syringe 101 connected with an inlet 104a of the first introducing passage. The solutions were sent into the micro flow channel under conditions in which the FRR was 9.0 and the TFR was 500 µL/minute to prepare RNP-loaded lipid nanoparticles. The resultant RNP-loaded lipid nanoparticles were subjected to dialysis in a similar manner to Reference Example 1, followed by measuring the number-weighted average particle size (nm), the polydispersity index (PdI) and ζ potential (mV) using a particle counter "zetasizer nano ZS ZEN3600" (manufactured by Marvern Instruments Ltd.) by a dynamic light scattering method (n=3, mean±SD). In addition, the encapsulation ratio (%) of gRNA and ssON into the lipid nanoparticles and the concentration thereof in the lipid nanoparticle solution were measured by RiboGreen assay (measured by Thermo Fisher Scientific Inc.) (n=3, mean±SD). The ratio (recovery ratio: %) of the total amount of nucleic acids collected after conducting dilution using the device shown in FIG. 3 and purification by dialysis relative to the total amount of gRNA and ssON used to prepare the RNP-loaded lipid nanoparticles was calculated from the measured values of the concentration of gRNA and ssON in the lipid nanoparticle solution.

TABLE 7

| | Number-weighted average particle size (nm) | Zeta potential (mV) | PdI | Recovery ratio (%) | Encapsulation ratio (%) |
|---|---|---|---|---|---|
| 10% (DSPC) | 109.5 ± 41.1 | −10.9 ± 18.7 | 0.34 ± 0.31 | 91.4 ± 6.4 | 60.5 ± 33.2 |
| 20% (DSPC) | 122.9 ± 17.8 | −3.0 ± 5.1 | 0.16 ± 0.02 | 88.3 ± 7.5 | 66.7 ± 7.7 |
| 10% (DOPE) | 109.5 ± 25.8 | −11.1 ± 11.5 | 0.22 ± 0.03 | 80.2 ± 7.8 | 64.3 ± 9.4 |
| 20% (DOPE) | 78.4 ± 3.8 | −4.5 ± 5.6 | 0.25 ± 0.00 | 87.4 ± 13.1 | 86.9 ± 2.0 |
| 0% | 95.7 ± 21.8 | −8.2 ± 11.5 | 0.21 ± 0.01 | 86.0 ± 5.0 | 72.9 ± 9.7 |

The measurement results are shown in Table 7. In the lipid nanoparticles containing 20% of DOPE, the tendency in which the particle size was small and the encapsulation ratio was high was confirmed.

The RNP-loaded lipid nanoparticles were added to the culture medium of HeLa-GFP cells seeded the day before such that the concentration of the Cas9 protein became 0.3 nM, 1 nM, or 5 nM, and then cultured. After two days had passed from addition of the RNP-loaded lipid nanoparticles, the culture medium was replaced, and then the cells were collected after an additional day, followed by measuring the GFP knockout efficiency (%) (the ratio (%) of cells which did not express GFP fluorescence to the total cells) by flow cytometry. The commercially available transfection reagent "Lipofectamine RNAiMAX" (manufactured by Thermo Fisher Scientific Inc.), which had been actually used to introduce RNP, was used to conduct comparison.

Figure 4:
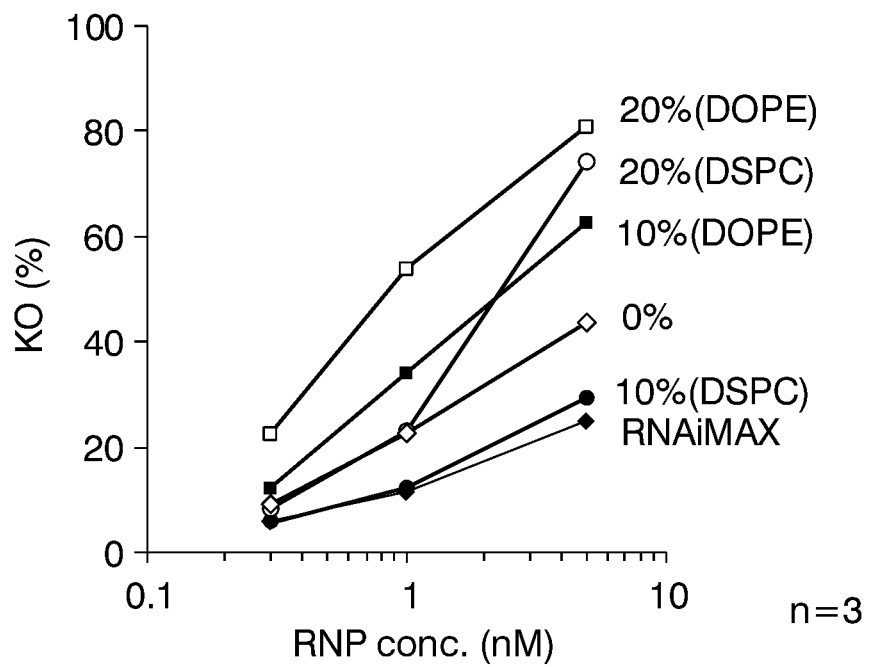
FIG. 4 is a drawing showing measurement results of GFP knockout efficiency (%) in HeLa-GFP cells by RNP-loaded lipid nanoparticles in Example 1.

The measurement results of the GFP knockout efficiency (%) of the RNP-loaded lipid nanoparticles (n=3, mean±SD) are shown in FIG. 4. The higher the amount of the neutral phospholipid, the higher the knockout activity exhibited. In addition, the RNP-loaded lipid nanoparticles containing DOPE as the neutral phospholipid exhibited higher knockout activity than that of the RNP-loaded lipid nanoparticles containing DSPC. In addition, the RNP-loaded lipid nanoparticles containing a high amount of the neutral phospholipid or the RNP-loaded lipid nanoparticles containing DOPE as the neutral phospholipid exhibited higher knockout activity than that of the "Lipofectamine RNAiMAX".

<Measurement of GFP Knockin Activity>

Figure 5:
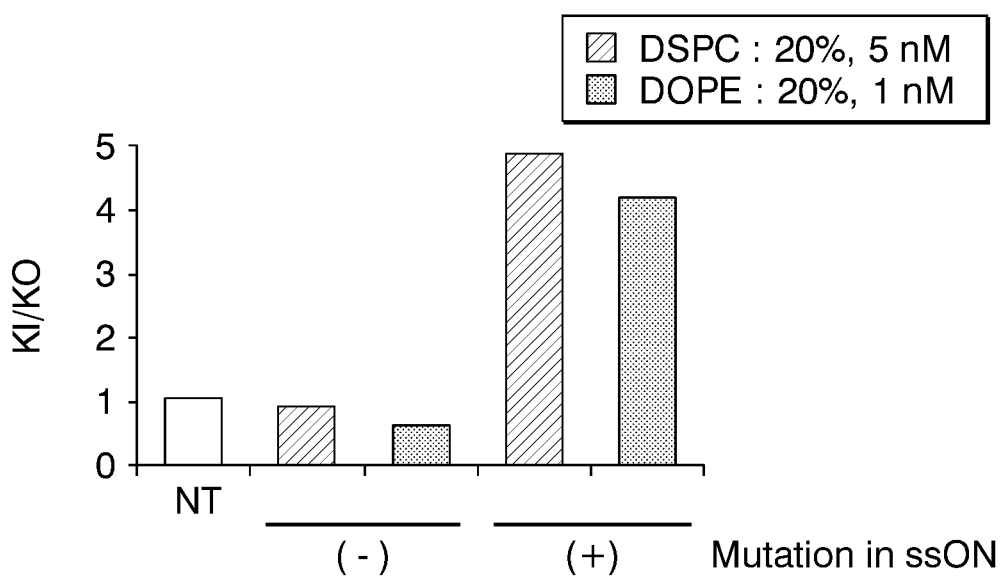
FIG. 5 is a drawing showing measurement results of the ratio of the knockin efficiency (%) to the knockout efficiency (%) ([KI (%)]/[KO (%)]) in HeLa-GFP cells by RNP-loaded lipid nanoparticles in Example 1.

RNP-loaded lipid nanoparticles were similarly prepared except that ssON available to conduct knockin was used instead of the ssON available to conduct knockout of GFP, and the amount of DSPC was 20% ("20% (DSPC)" in Table 6) or the amount of DOPE was 20% ("20% (DOPE)" in Table 6) in the lipid constitution. The RNP-loaded lipid nanoparticles were added to the culture medium of Hela-GFP cells seeded the day before such that the concentration of the Cas9 protein became 0.3 nM, 1 nM, or 5 nM, and then cultured. After two days had passed from addition of the RNP-loaded lipid nanoparticles, the culture medium was replaced, and then the cells were collected after an additional day, followed by measuring the knockin efficiency (%) (the ratio (%) of cells which expressed BFP fluorescence to the total cells) by flow cytometry. Since BFP has a shorter fluorescent wavelength than that of GFP, cells in which the GFP gene is modified by knockin to the BFP gene can be quantitatively distinguished by flow cytometry. Results of the ratio of the knockin efficiency (%) to the knockout efficiency (%) ([KI (%)]/[KO (%)]) of the RNP-loaded lipid nanoparticles are shown in FIG. 5. As a result, in the case where the ssON in which mutation was introduced was used, the gene knockin efficiency of every type of RNP-loaded lipid nanoparticles was 4% to 5%.

Example 2

Effects of formulation of lipid nanoparticles on gene knockout activity were investigated.

<Primary Screening>

Six factors composed of: the amount of the pH-sensitive cationic lipid (CL) (30% by mol, 40% by mol, or 50 by mol), the amount the neutral phospholipid (PL) (20% by mol, 35% by mol, or 50% by mol), the amount of PEG-DMG (1% by mol, 2.5% by mol, or 4% by mol), the type of the pH-sensitive cationic lipid (CL4H6 or CL15H6 (pKa: 7.25 or less, Patent Document 2)), the type of the neutral phospholipid (DSPC or DOPE), and the ratio of RNP/lipid ($1.8 \times 10^{-4}$ mol, $2.7 \times 10^{-4}$ mol, or $3.6 \times 10^{-4}$ mol) were investigated.

Three levels were selected for continuous variables and two levels were selected for categorical factors. Among 324 combinations which were whole combinations, 14 formulations listed in Table 8 were selected by a definitive screening plan, which was one of the Design of Experiment (DoE). The lipid constitution was as follows: the pH-sensitive cationic lipid (CL): the neutral phospholipid (PL):cholesterol:PEG-DMG=X:Y:(100-X-Y):Z (% by mol) (X: values in the column "CL (%)" in Table 8, and Y: values in the column "PL (%)" in Table 8).

TABLE 8

| Entry (No.) | CL (%) | PL (%) | PEG-DMG (%) | CL | PL | RNP/lipid (mol, ×10$^{-4}$) |
|---|---|---|---|---|---|---|
| A-1 | 50 | 20 | 2.5 | 15H6 | DOPE | 1.8 |
| A-2 | 30 | 35 | 4 | 4H6 | DOPE | 1.8 |
| A-3 | 30 | 50 | 1 | 15H6 | DSPC | 1.8 |
| A-4 | 50 | 50 | 4 | 15H6 | DSPC | 1.8 |
| A-5 | 40 | 20 | 1 | 4H6 | DSPC | 1.8 |
| A-6 | 40 | 35 | 2.5 | 15H6 | DOPE | 2.7 |
| A-7 | 50 | 50 | 1 | 4H6 | DOPE | 2.7 |
| A-8 | 30 | 20 | 4 | 15H6 | DSPC | 2.7 |
| A-9 | 40 | 35 | 2.5 | 4H6 | DSPC | 2.7 |
| A-10 | 40 | 50 | 4 | 15H6 | DOPE | 3.6 |
| A-11 | 30 | 20 | 1 | 4H6 | DOPE | 3.6 |
| A-12 | 50 | 20 | 4 | 4H6 | DOPE | 3.6 |
| A-13 | 50 | 35 | 1 | 15H6 | DSPC | 3.6 |
| A-14 | 30 | 50 | 2.5 | 4H6 | DSPC | 3.6 |

CL15H6

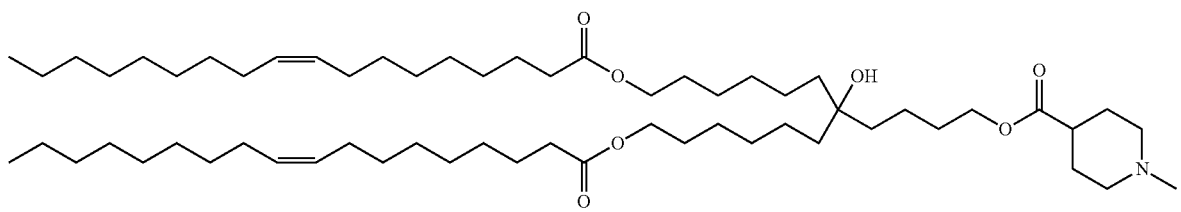

RNP-loaded lipid nanoparticles available to conduct knockout of GFP were prepared in a similar manner to that of the RNP-loaded lipid nanoparticles available to conduct knockout of GFP prepared in Example 1, except that the ratios of the lipid components, the lipids, and RNP are shown in Table 8. The resultant RNP-loaded lipid nanoparticles were measured in terms of the number-weighted average particle size (nm), PdI, and the encapsulation ratio (%) of gRNA and ssON into the lipid nanoparticles in the same way as that of Example 1.

Figure 6:
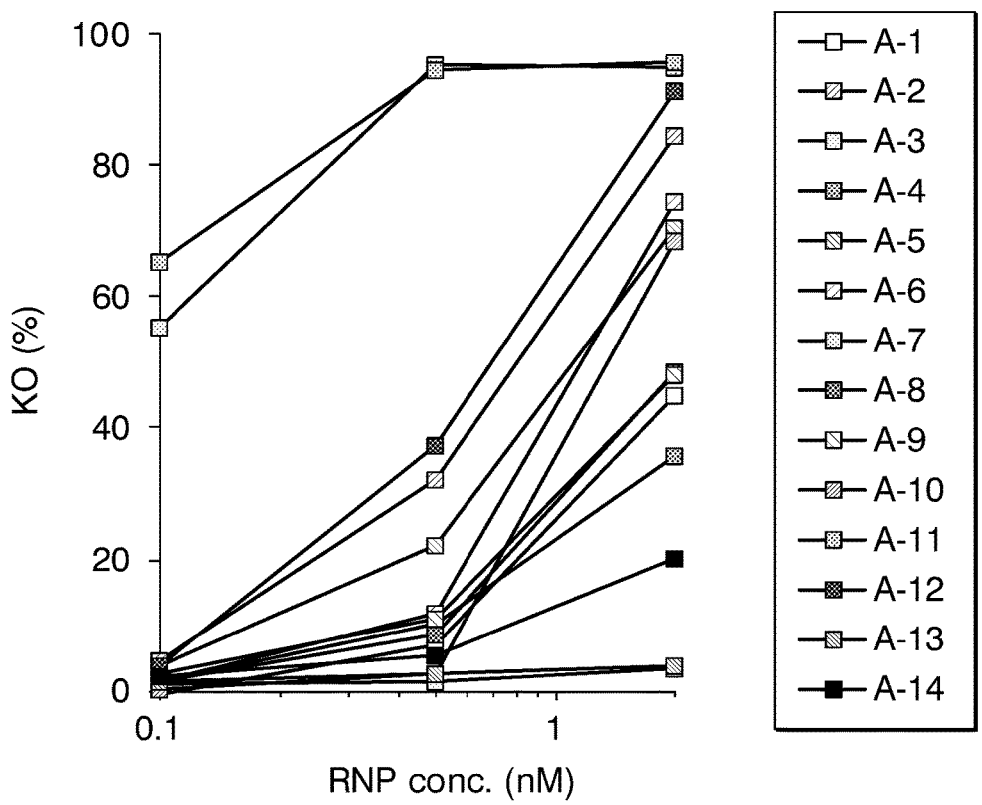
FIG. 6 is a drawing showing measurement results of GFP knockout efficiency (%) in HeLa-GFP cells by RNP-loaded lipid nanoparticles at the primary screening in Example 2.

The RNP-loaded lipid nanoparticles were added to the culture medium of Hela-GFP cells seeded the day before such that the concentration of the Cas9 protein became 0.1 nM, 0.5 nM, or 2 nM, and then cultured. After two days had passed from addition of the RNP-loaded lipid nanoparticles, the culture medium was replaced, and then the cells were collected after additional three days, followed by measuring the GFP knockout efficiency (%) by flow cytometry in the same way as that of Example 1. Results are shown in Table 9. In addition, the measurement results of the GFP knockout efficiency (%) are shown in FIG. 6.

TABLE 9

| Entry (No.) | Response | | | |
|---|---|---|---|---|
| | Number-weighted average particle size (nm) | PdI | Encapsulation ratio (%) | KO activity (%) |
| A-1 | 95.08 | 0.164 | 94.3 | 17.04 |
| A-2 | 246.4 | 0.124 | 76.1 | 40.57 |
| A-3 | 693.8 | 0.35 | 67.3 | 1.91 |
| A-4 | 112 | 0.212 | 92.3 | 15.79 |
| A-5 | 348.9 | 0.074 | 50.1 | 32.11 |

TABLE 9-continued

| Entry (No.) | Response | | | |
|---|---|---|---|---|
| | Number-weighted average particle size (nm) | PdI | Encapsulation ratio (%) | KO activity (%) |
| A-6 | 136.1 | 0.234 | 98.7 | 29.23 |
| A-7 | 244.9 | 0.128 | 100.8 | 81.92 |
| A-8 | 282.4 | 0.17 | 72.9 | 19.61 |
| A-9 | 205.7 | 0.089 | 65.5 | 20.62 |
| A-10 | 106.5 | 0.199 | 94.6 | 23.89 |
| A-11 | 251.5 | 0.082 | 87.5 | 85.26 |
| A-12 | 75.98 | 0.226 | 87.5 | 44.25 |
| A-13 | 601.4 | 0.098 | 75.7 | 2.606 |
| A-14 | 276.2 | 0.018 | 59.0 | 9.27 |

Figure 7:
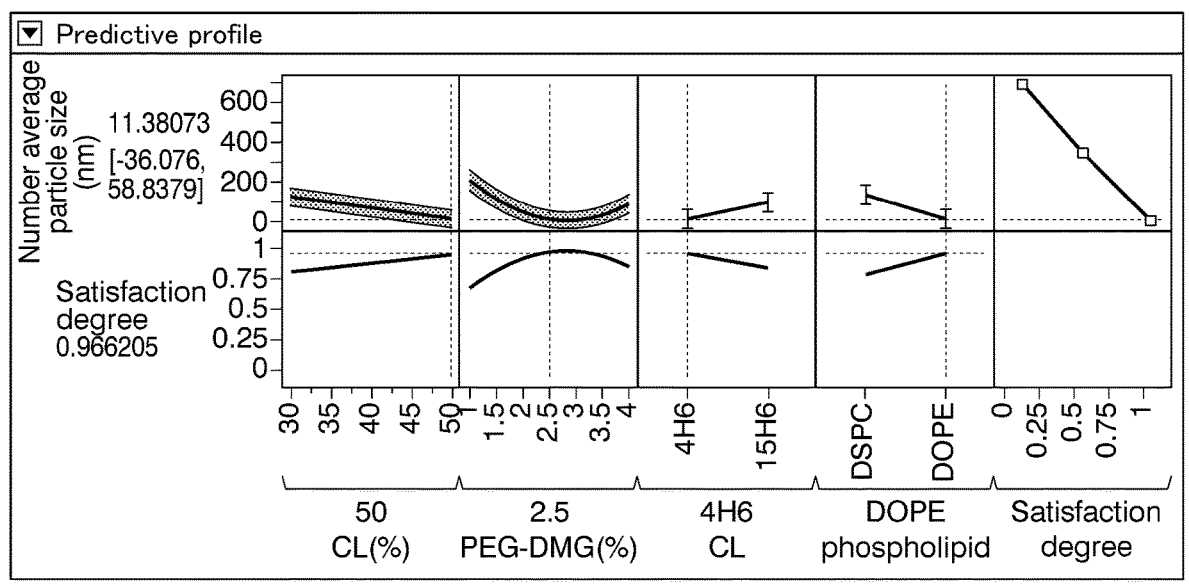
FIG. 7 is a drawing showing a predictive profile of the number-weighted average particle size when factors which significantly affect the number-weighted average particle size at the primary screening in Example 2 are changed.

Statistical analysis was performed on the number-weighted average particle size. Results of the principal effect that significantly affected the number-weighted average particle size and the interaction between two factors are shown in Table 10, and the predictive profile of the number-weighted average particle size when factors that significantly affected the number-weighted average particle size were changed is shown in FIG. 7. The amount of the pH-sensitive cationic lipid, the amount of PEG-DMG, the type of the pH-sensitive cationic lipid, and the neutral phospholipid were detected as factors that significantly affect the particle size. More specifically, it became apparent that the particle size was reduced by increasing the amount of the pH-sensitive cationic lipid, approximating the amount of PEG-DMG 2.5% by mol, using CL4H6 as the pH-sensitive cationic lipid, or using DOPE as the neutral phospholipid. Particularly, it became apparent that the amount of the PEG lipid and the type of the neutral phospholipid were factors which had a great impact thereon.

TABLE 10

| | | Test of effects | | | | |
|---|---|---|---|---|---|---|
| | Factors | Number of parameter | Freedom degree | Square sum | F value | p value (Prove > F) |
| Principal effect | CL (%) (30, 50) | 1 | 1 | 31276.76 | 40.1352 | 0.0007 |
| | PEG-DMG (%) (1, 4) | 1 | 1 | 151341.29 | 194.2054 | <0.0001 |
| | CL | 1 | 1 | 24720.48 | 31.7220 | 0.0013 |
| | Phospholipid | 1 | 1 | 52557.16 | 67.4428 | 0.0002 |
| Interaction between two factors | CL (%) * PEG-DMG (%) | 1 | 1 | 7309.61 | 9.3799 | 0.0221 |
| | PEG-DMG (%) * CL | 1 | 1 | 77784.48 | 99.8152 | <0.0001 |
| | PEG-DMG (%) * PEG-DMG (%) | 1 | 1 | 52309.15 | 67.1246 | 0.0002 |

Figure 8:
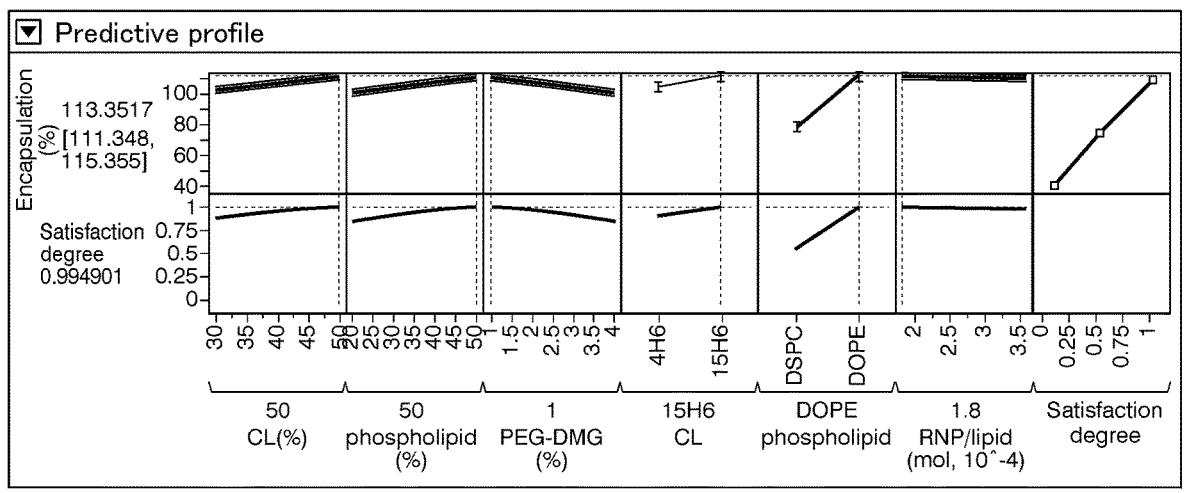
FIG. 8 is a drawing showing a predictive profile of the encapsulation ratio when factors which significantly affect the encapsulation ratio at the primary screening in Example 2 are changed.

Statistical analysis was similarly performed on the encapsulation ratio. Results of the principal effect that significantly affected the encapsulation ratio and the interaction between two factors are shown in Table 11, and the predictive profile of the encapsulation ratio when factors that significantly affected the encapsulation ratio were changed is shown in FIG. 8. As a result, it became apparent that all factors significantly affect the encapsulation ratio. More specifically, it became apparent that the encapsulation ratio was improved by increasing the amount of the pH-sensitive cationic lipid, increasing the amount of the neutral phospholipid, decreasing the amount of PEG-DMG, using CL15H6 as the pH-sensitive cationic lipid, using DOPE as the neutral phospholipid, and decreasing the ratio of RNP/lipid. The type of neutral phospholipid was a factor which had the greatest impact thereon.

TABLE 11

| | | Test of effects | | | | |
|---|---|---|---|---|---|---|
| | Factors | Number of parameter | Freedom degree | Square sum | F value | p value (Prove > F) |
| Principal effect | CL (%) (30, 50) | 1 | 1 | 273.0400 | 470.7347 | <0.0001 |
| | Phospholipid (%) (20, 50) | 1 | 1 | 107.4924 | 185.3222 | 0.0002 |
| | PEG-DMG (%) (1, 4) | 1 | 1 | 6.8200 | 11.7580 | 0.0266 |
| | CL | | | 348.6864 | 601.1528 | <0.0001 |
| | Phospholipid | | | 1563.4561 | 2695.477 | <0.0001 |
| | RNP/lipid (mol) (1.8, 3.6 ×10$^{-4}$) | 1 | 1 | 14.1151 | 24.3352 | 0.0079 |
| Interaction between two factors | Phospholipid (%)* RNP/lipid (mol) | 1 | 1 | 77.9284 | 134.3525 | 0.0003 |
| | PEG-DMG (%) * Phospholipid | 1 | 1 | 296.1108 | 510.5100 | <0.0001 |
| | CL* RNP/lipid (mol) | 1 | 1 | 6.0364 | 10.4071 | 0.0321 |

Figure 9:
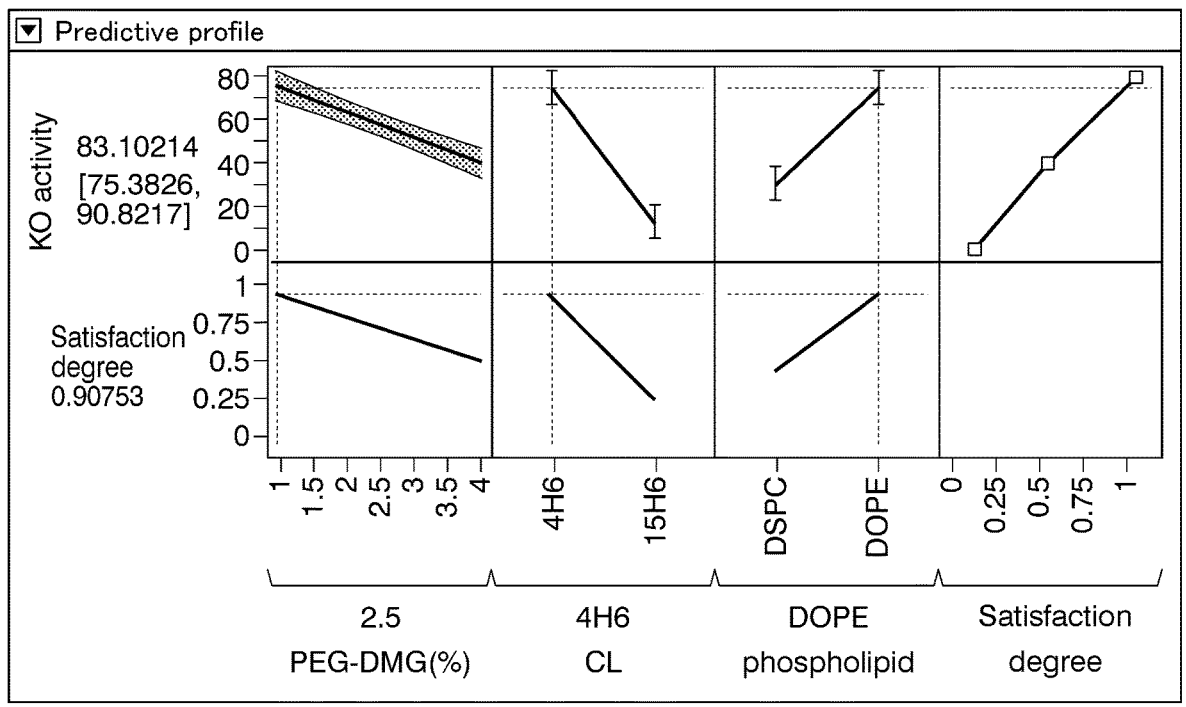
FIG. 9 is a drawing showing a predictive profile of the gene knockout activity when factors which significantly affect the gene knockout activity at the primary screening in Example 2 are changed.

Statistical analysis was similarly performed on the gene knockout activity (%). Results of the principal effect that significantly affected the gene knockout activity (%) and the interaction between two factors are shown in Table 12, and the predictive profile of the gene knockout activity (%) when factors that significantly affected the gene knockout activity (%) were changed is shown in FIG. 9. The amount of PEG-DMG, the type of the pH-sensitive cationic lipid, and the type of the neutral phospholipid were identified as factors which significantly affected the knockout activity. More specifically, it became apparent that the gene knockout activity was improved by making the amount of the PEG-DMG be approximately 1% by mol, using CL4H6 as the pH-sensitive cationic lipid, and using DOPE as the neutral phospholipid. Particularly, the type of the cationic lipid and the type of the neutral phospholipid were factors which had a great impact thereon.

TABLE 12

| | | Test of effects | | | | |
|---|---|---|---|---|---|---|
| | Factors | Number of parameter | Freedom degree | Square sum | F value | p value (Prove > F) |
| Principal effect | PEG-DMG (%) (1, 4) | 1 | 1 | 417.5155 | 17.2980 | 0.0032 |
| | CL | | | 1730.8645 | 71.7111 | <0.0001 |
| | Phospholipid | 1 | 1 | 2984.3383 | 123.6435 | <0.0001 |
| Interaction between two factors | PEG-DMG (%) * CL | 1 | 1 | 1679.3493 | 69.5768 | <0.0001 |
| | CL * Phospholipid | 1 | 1 | 1180.6233 | 48.9142 | 0.0001 |

The formulations A-7 and A-11 in which conditions to improve the gene knockout activity were satisfied exhibited actually higher knockout activity than that of other lipid nanoparticles (FIG. 6) and the $IC_{50}$ (50% inhibitory concentration) of RNP thereof was 0.1 nM or less (Cas9 protein concentration equivalent). In addition, the maximum knockout efficiency reached 95% or more (FIG. 6).

<Secondary Screening>

The secondary screening was conducted based on the results of the primary screening. The experimental system was evaluated in the same experimental system as that of the primary screening.

Nine formulations as shown in Table 13 were selected from all 27 combinations by a definitive screening plan in which 3 factors of the amount of the pH-sensitive cationic lipid (CL) (30% by mol, 40% by mol, or 50% by mol), the amount of the neutral phospholipid (PL) (20% by mol, 35% by mol, or 50% by mol), and the amount of the PEG-DMG (1.0% by mol, 2.0% by mol, or 3.0% by mol) were investigated at 3 levels. The lipid constitution was as follows: the pH-sensitive cationic lipid (CL): the neutral phospholipid (PL):cholesterol:PEG-DMG=X:Y:(100-X-Y):Z (% by mol) (X: values in the column "CL (%)" in Table 13, and Y: values in the column "PL (%)" in Table 13). CL4H6 was used as the pH-sensitive cationic lipid, and DOPE was used as the neutral phospholipid.

TABLE 13

| | Factors | | | Response | | |
|---|---|---|---|---|---|---|
| | | | | Number-weighted | Encapsulation | KO |
| Entry (No.) | CL (%) | PL (%) | PEG-DMG (%) | average particle size (nm) | ratio (%) | activity (%) |
| B-1 | 30 | 20 | 1 | 379.6 | 83.6 | 77.6 |
| B-2 | 30 | 35 | 2 | 137.2 | 85.1 | 65.7 |
| B-3 | 30 | 50 | 3 | 93.3 | 83.2 | 42.5 |
| B-4 | 40 | 20 | 2 | 134.4 | 84.4 | 70.6 |
| B-5 | 40 | 35 | 3 | 41.4 | 88.6 | 52.0 |
| B-6 | 40 | 50 | 1 | 253.6 | 96.6 | 87.8 |
| B-7 | 50 | 20 | 3 | 75.6 | 84.5 | 49.5 |
| B-8 | 50 | 35 | 1 | 243.4 | 97.4 | 84.6 |
| B-9 | 50 | 50 | 2 | 100.7 | 94.1 | 73.2 |

RNP-loaded lipid nanoparticles used to conduct GFP knockout were prepared in the same way as that of the primary screening except that the ratio of the lipid components, the lipid and the RNP was adjusted as shown in Table 13, and the number-weighted average particle size (nm), PdI, and the encapsulation ratio (%) of gRNA and ssON into lipid nanoparticles of the resultant RNP-loaded lipid nanoparticles were measured. In addition, the GFP knockout efficiency (%) was measured by adding the RNP-loaded lipid nanoparticles to Hela-GFP cells in a similar manner to that of the primary screening. Results are shown in Table 13.

Figure 10:
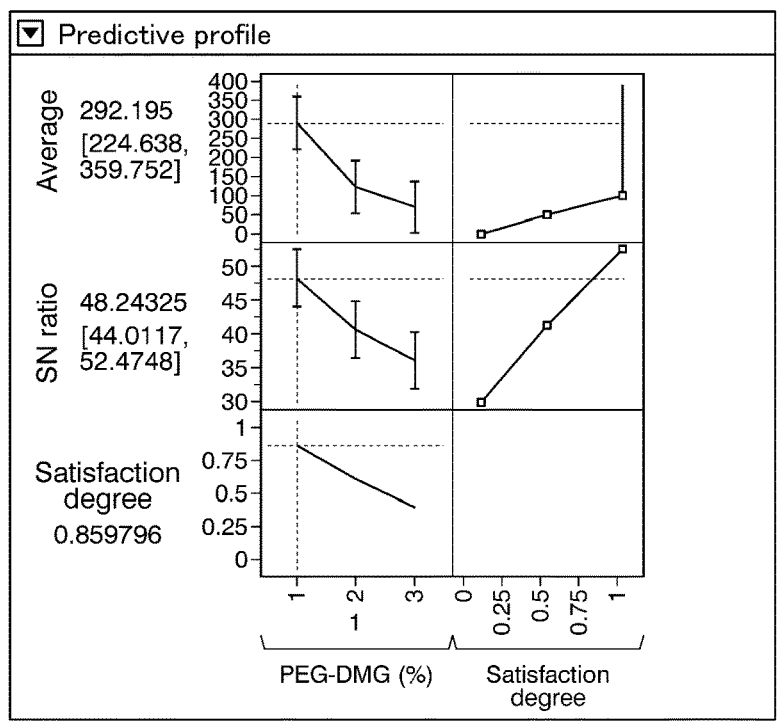
FIG. 10 is a drawing showing a predictive profile of the number-weighted average particle size when factors which significantly affect the number-weighted average particle size at the secondary screening in Example 2 are changed.

Statistical analysis was performed on the number-weighted average particle size. Results of the principal effect that significantly affected the number-weighted average particle size are shown in Table 14, and the predictive profile of the number-weighted average particle size when factors that significantly affected the number-weighted average particle size were changed is shown in FIG. 10. It became apparent that the particle size was reduced by increasing the amount of the PEG lipid.

TABLE 14

| | | Test of effects | | | | |
|---|---|---|---|---|---|---|
| | Factors | Number of parameter | Freedom degree | Square sum | F value | p value (Prove > F) |
| Principal effect | PEG-DMG (%) (1, 2, 3) | 2 | 2 | 80497.321 | 17.6005 | 0.0031 |

Figure 11:
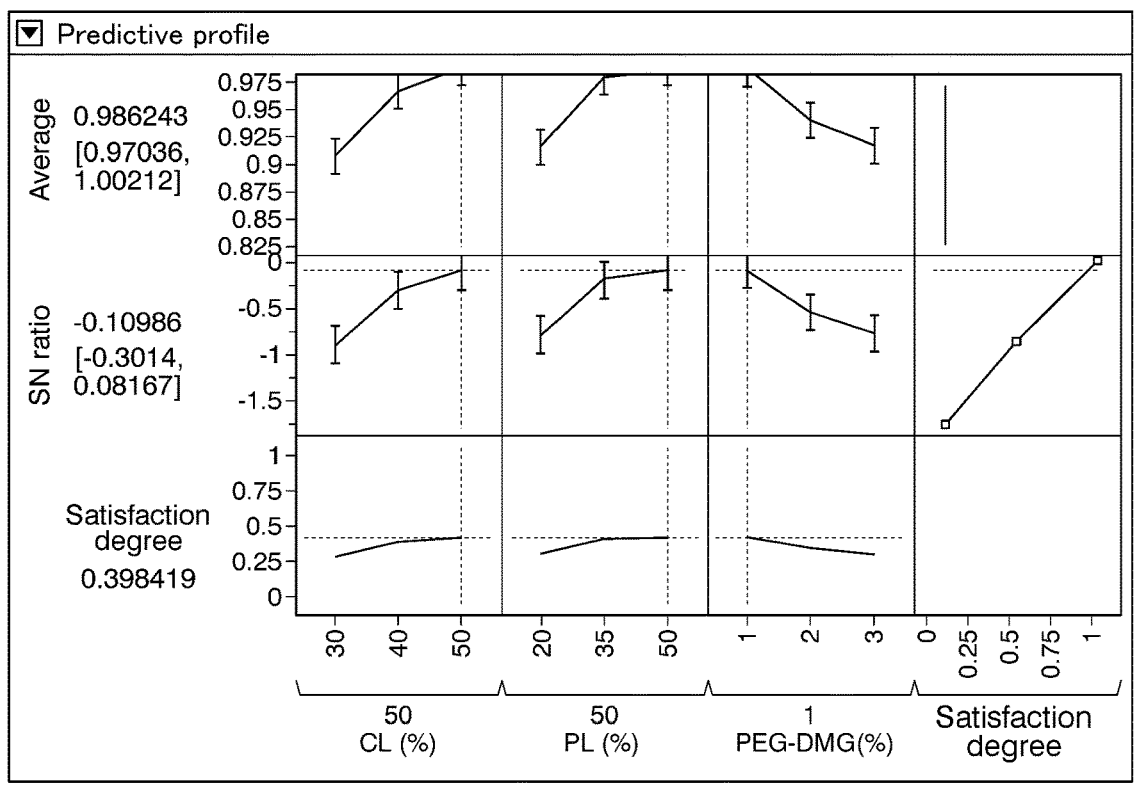
FIG. 11 is a drawing showing a predictive profile of the encapsulation ratio when factors which significantly affect the encapsulation ratio at the secondary screening in Example 2 are changed.

Statistical analysis was similarly performed on the encapsulation ratio. Results of the principal effect that significantly affected the encapsulation ratio are shown in Table 15, and the predictive profile of the encapsulation ratio when factors that significantly affected the encapsulation ratio were changed is shown in FIG. 11. As a result, it became apparent that the encapsulation ratio was improved by increasing the amount of the pH-sensitive cationic lipid, increasing the amount of the neutral phospholipid, or decreasing the amount of PEG-DMG.

TABLE 15

| | | Test of effects | | | | |
|---|---|---|---|---|---|---|
| | Factors | Number of parameter | Freedom degree | Square sum | F value | p value (Prove > F) |
| Principal effect | CL (%) (30, 40, 50) | 2 | 2 | 0.00866781 | 189.1389 | 0.0053 |
| | PL (%) (20, 35 50) | 2 | 2 | 0.00624187 | 136.2028 | 0.0073 |
| | PEG-DMG (%) (1, 2, 3) | 2 | 2 | 0.00665894 | 145.3037 | 0.0068 |

Figure 12:
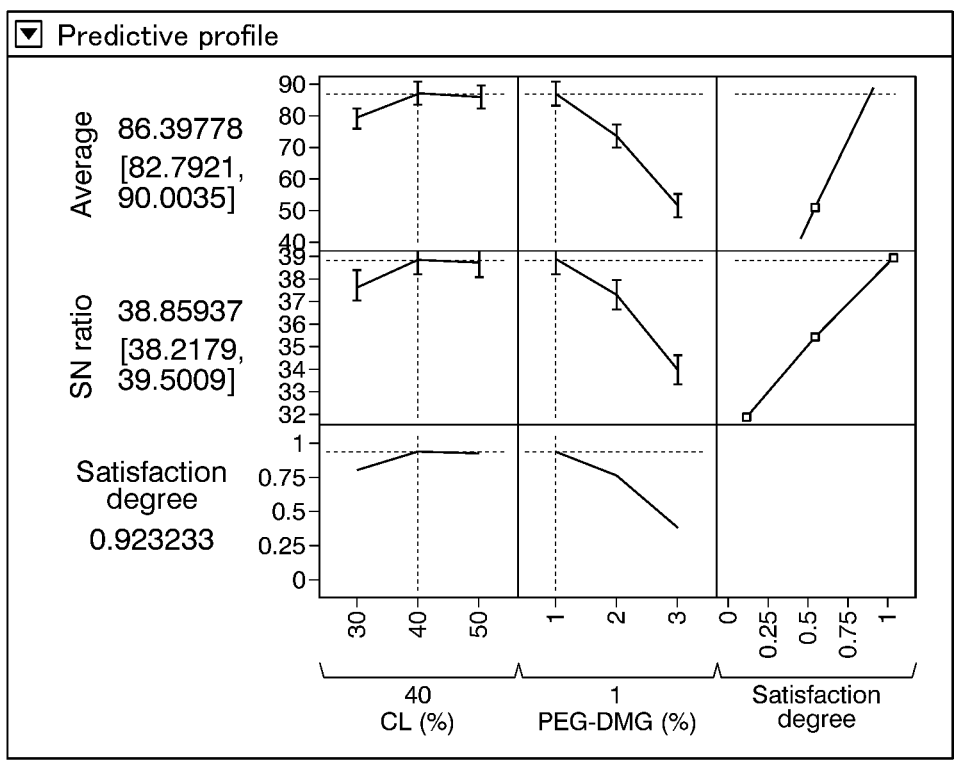
FIG. 12 is a drawing showing a predictive profile of the gene knockout activity when factors which significantly affect the gene knockout activity at the secondary screening in Example 2 are changed.

Statistical analysis was similarly performed on the gene knockout activity (%). Results of the principal effect that significantly affected the gene knockout activity (%) are shown in Table 16, and the predictive profile of the gene knockout activity (%) when factors that significantly affected the gene knockout activity (%) were changed is shown in FIG. 12. It became apparent that the gene knockout activity was improved by decreasing the amount of PEG-DMG or increasing the amount of the pH-sensitive cationic lipid to 40% by mol or more.

TABLE 16

| | | Test of effects | | | | |
|---|---|---|---|---|---|---|
| | Factors | Number of parameter | Freedom degree | Square sum | F value | p value (Prove > F) |
| Principal effect | CL (%) (30, 40, 50) | 2 | 2 | 119.4482 | 19.6730 | 0.0085 |
| | PEG-DMG (%) (1, 2, 3) | 2 | 2 | 1908.5049 | 314.3286 | <0.0001 |

It became apparent from the results that favorable RNP-loaded lipid nanoparticles in which the number-weighted average particle size was small, the encapsulation efficiency of RNP was high, and the gene knockout activity (%) was high were obtained by using CL4H6 as the pH-sensitive cationic lipid in an amount of 40% by mol to 50% by mol, using DOPE as the neutral phospholipid in an amount of 20% by mol to 50% by mol, using the PEG lipid in an amount of 1.5% by mol to 2.0% by mol, and adjusting the ratio of RNP/lipid to $3.6 \times 10^{-4}$ mol or more.

Example 3

The cytotoxicity and the storage stability of the RNP-loaded lipid nanoparticles B-4 and B-9 prepared in Example 2 were investigated.

<Evaluation of Cytotoxicity>

The RNP-loaded lipid nanoparticles were added to the culture medium of HeLa-GFP cells seeded the day before such that the concentration of the Cas9 protein became 0.3 nM, 0.5 nM, or 1 nM, and then cultured. After one day had passed from addition of the RNP-loaded lipid nanoparticles, the WST-8 assay was conducted. The WST-8 assay was conducted using a cell counting kit (product name: "Cell Counting Kit-8", manufactured by DOJINDO LABORATORIES). The WST-8 assay was similarly conducted using HeLa-GFP cells in the culture medium in which PBS(−) was added instead of the RNP-loaded lipid nanoparticles as a control.

Figure 13:
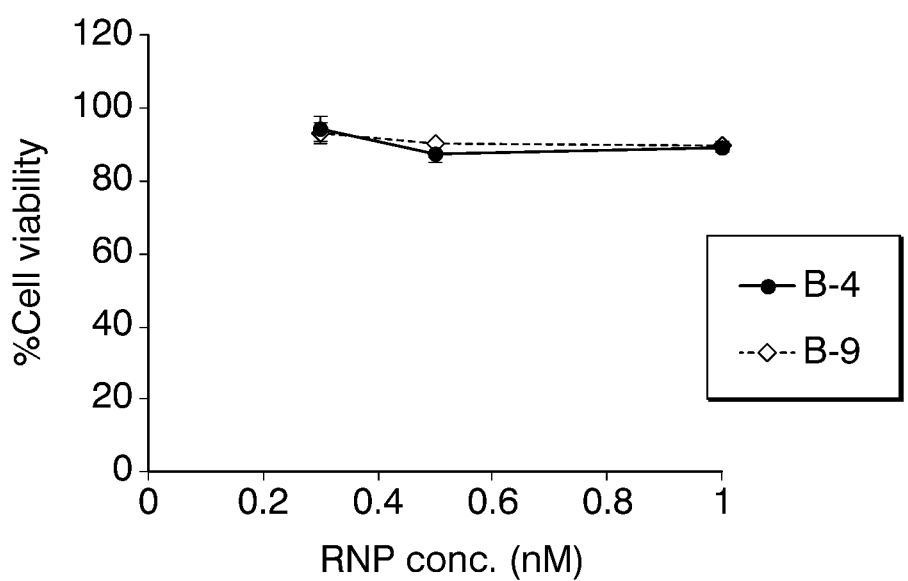
FIG. 13 is a drawing showing measurement results of the cell viability (%) of cells to which RNP-loaded lipid nanoparticle B-4 or B-9 was added in Example 3.

The cell viability of the cells to which the RNP-loaded lipid nanoparticles were added ([measured value of the WST-8 assay in the cells to which the RNP-loaded lipid nanoparticles were added]/[measured value of the WST-8 assay in the control cells]×100:%) was calculated. Results are shown in FIG. 13. The cell viability of the cells in which the RNP-loaded lipid nanoparticles B-4 or B-9 were introduced was approximately 100%, regardless of the amount of the RNP-loaded lipid nanoparticles. Thus, the RNP-loaded lipid nanoparticles did not exhibit significant cytotoxicity of the Hela cells.

<Evaluation of Storage Stability>

The RNP-loaded lipid nanoparticles B-9 prepared in Example 2 were stored at 4° C. and the physical property and the knockout activity after the storage were investigated.

Specifically, the zeta potential and PdI were measured over time. In addition, the GFP knockout activity was investigated by adding the RNP-loaded lipid nanoparticle B-9 before storage at 4° C. or after storage at 4° C. for 2 weeks to the culture medium such that the concentration of the Cas9 protein became 0.3 nM to allow introduction thereof into HeLa-GFP cells. The zeta potential, PdI, and the GFP knockout activity thereof were measured in the same way as that of Example 1.

Figure 14:
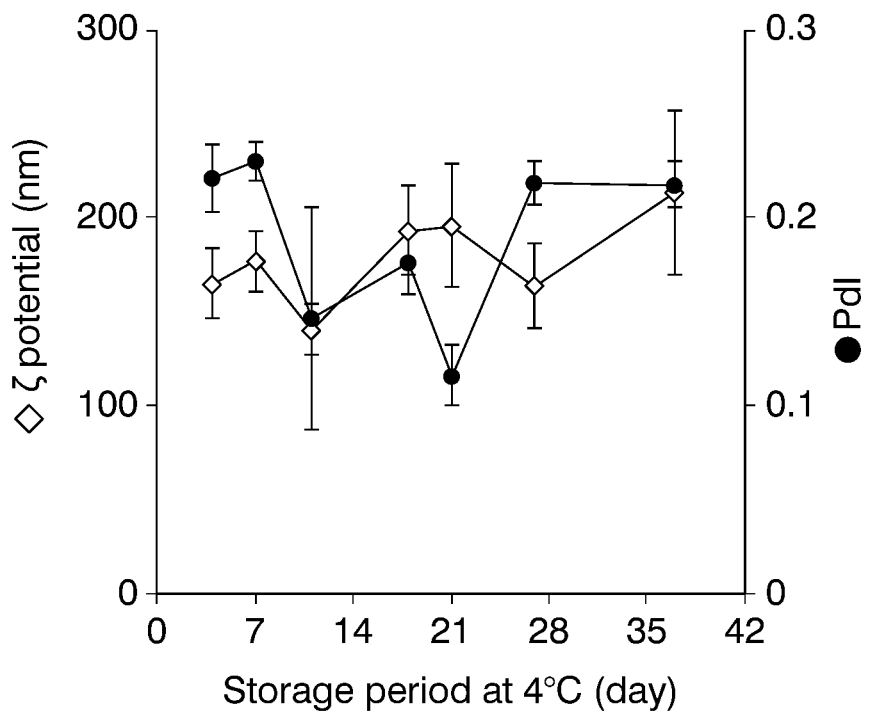
FIG. 14 is a drawing showing temporal measurement results of zeta potential and PdI of cells to which the RNP-loaded lipid nanoparticle B-9 was added and then stored at 4° C. in Example 3.
Figure 15:
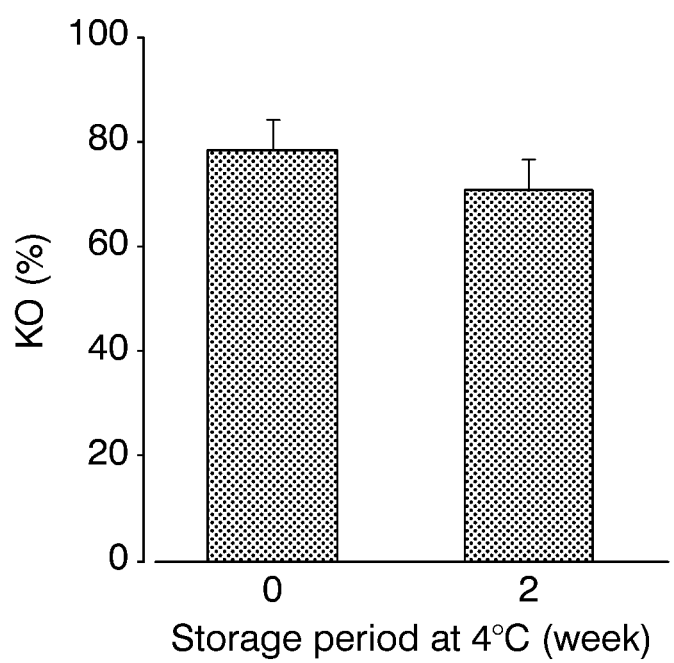
FIG. 15 is a drawing showing measurement results of the GFP knockout efficiency (%) in HeLa-GFP cells by the RNP-loaded lipid nanoparticle B-9 before or after being stored at 4° C. in Example 3.

The measurement results of the zeta potential and PdI are shown in FIG. 14, and the measurement results of the GFP knockout activity are shown in FIG. 15. As a result, both the physical property and the knockout activity of the RNP-loaded lipid nanoparticle B-9 stored at 4° C. were maintained for at least 2 weeks after production at a level similar to that before storage. It was confirmed from the results that the RNP-loaded lipid nanoparticles according to the present invention had a practically sufficient storage stability.

Example 4

Effects of the base length of ssON loaded on the RNP-loaded lipid nanoparticle on the knockout activity were investigated.

As the ssON used to conduct knockout of GFP, DNA having a 132-base length (SEQ. ID. NO. 5), used in Example 2, DNA having a 20-base length (base sequence which was identical to the 68$^{th}$ to 87$^{th}$ region of SEQ. ID. NO. 5), DNA having a 60-base length (base sequence which was identical to the 48$^{th}$ to 107$^{th}$ region of SEQ. ID. NO. 5), or RNA obtained from DNA having a 60-base length (SEQ. ID. NO. 7) was used.

Figure 16A:
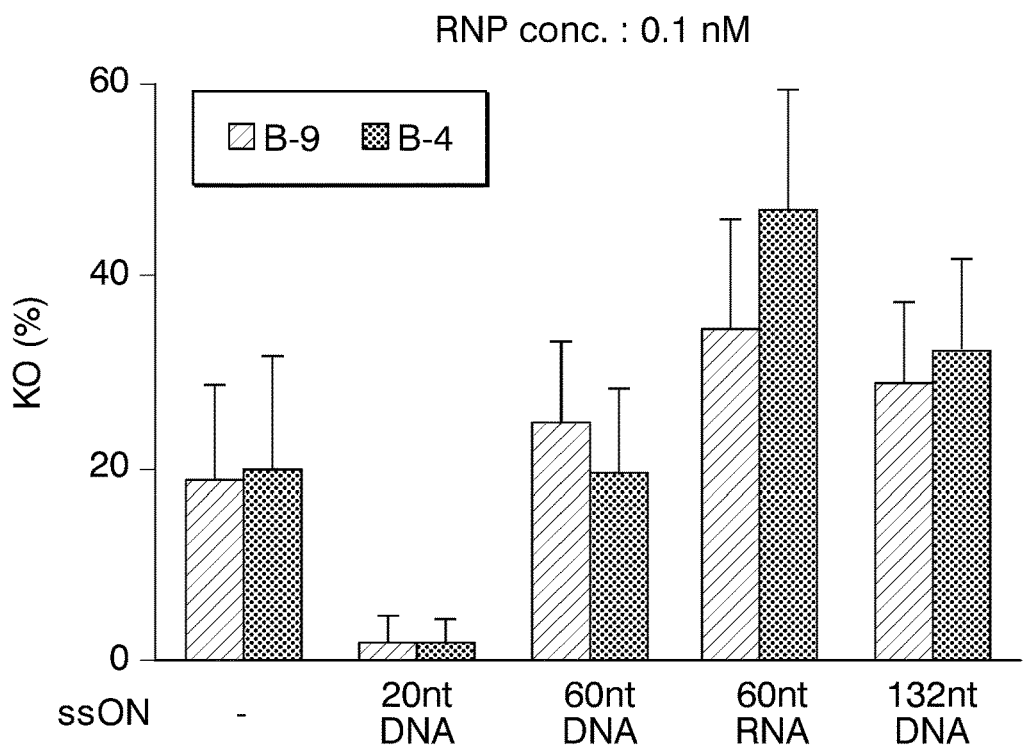
FIG. 16A is a drawing showing measurement results of the GFP knockout efficiency (%) in HeLa-GFP cells cultured in the medium in which the RNP-loaded lipid nanoparticle B-4 or B-9 was added such that the concentration of Cas9 protein was 0.1 nM in Example 4.
Figure 16B:
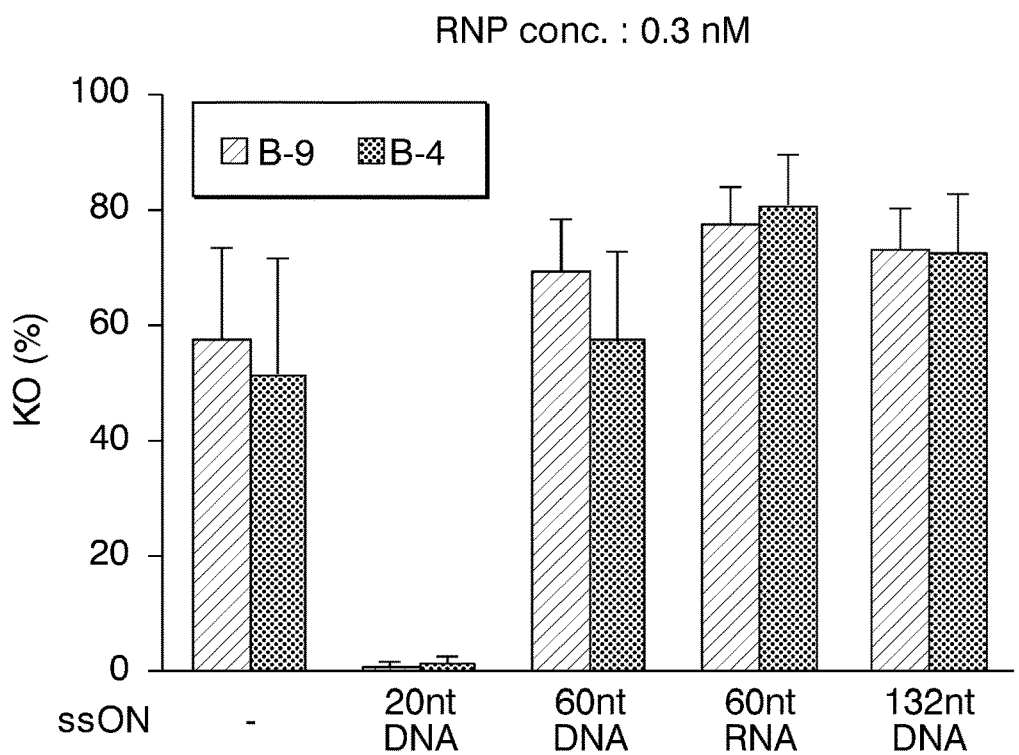
FIG. 16B is a drawing showing measurement results of the GFP knockout efficiency (%) in HeLa-GFP cells cultured in the medium in which the RNP-loaded lipid nanoparticle B-4 or B-9 was added such that the concentration of Cas9 protein was 0.3 nM in Example 4.

RNP-loaded lipid nanoparticles B-9 and B-4 were prepared in a similar manner to that of Example 2, except that DNA having a 132-base length, DNA having a 20-base length, DNA having a 60-base length, or RNA having a 60-base length was used as ssON. Then, the RNP-loaded lipid nanoparticles were added to the culture medium of HeLa-GFP cells seeded the day before such that the concentration of the Cas9 protein became 0.1 nM or 0.3 nM, and then cultured. After two days had passed from addition of the RNP-loaded lipid nanoparticles, the culture medium was replaced, and then the cells were further cultured for additional three days, followed by collecting the cells to measure the GFP knockout efficiency (%) (the ratio (%) of cells which did not express GFP fluorescence to entire cells) by flow cytometry. Results of cells in which the RNP-loaded lipid nanoparticles were introduced such that the concentration of the Cas9 protein became 0.1 nM are shown in FIG. 16A, and results of cells in which the RNP-loaded lipid nanoparticles were introduced such that the concentration of the Cas9 protein became 0.3 nM are shown in FIG. 16B.

It was observed from the results of both the RNP-loaded lipid nanoparticles B-4 and B-9 that the longer the base length of the ssON, the higher the gene knockout activity. In addition, it was observed that, in the case of uniform base length, the knockout activity of RNA as ssON was higher than that of DNA as ssON.

Example 5

Lipid nanoparticles on which RNA-dependent DNA nuclease Cpf1 was loaded instead of Cas9 were prepared and then the gene knockout activity thereof was investigated.

The RNP-loaded lipid nanoparticles B-9 were prepared in a similar manner to that of Example 2, except that Cpf1 protein (product name: "Alt-R A.s. Cas12a (Cpf1) Ultra", manufactured by Integrated DNA technologies) was used instead of the Cas9 protein, RNA having a 41-base length (SEQ. ID. NO. 8) or RNA having a 100-base length (SEQ. ID. NO. 9) was used as gRNA instead of crRNA and tracrRNA used in Reference Example 1, and RNA having a 120-base length (SEQ. ID. NO. 10) or RNA having a 60-base length (base sequence identical to the 27$^{th}$ to 86$^{th}$ region of SEQ. ID. NO. 10; SEQ. ID. NO. 11) was used as ssON. Then, the RNP-loaded lipid nanoparticles were added to the culture medium of HeLa-GFP cells seeded the day before such that the concentration of the Cpf1 protein became 0.5 nM, 1 nM, or 2 nM, and then cultured. After two days had passed from addition of the RNP-loaded lipid nanoparticles, the culture medium was replaced, and then the cells were further cultured for additional three days, followed by collecting the cells to measure the GFP knockout efficiency (%) (the ratio (%) of cells which did not express GFP fluorescence to entire cells) by flow cytometry.

Figure 17:
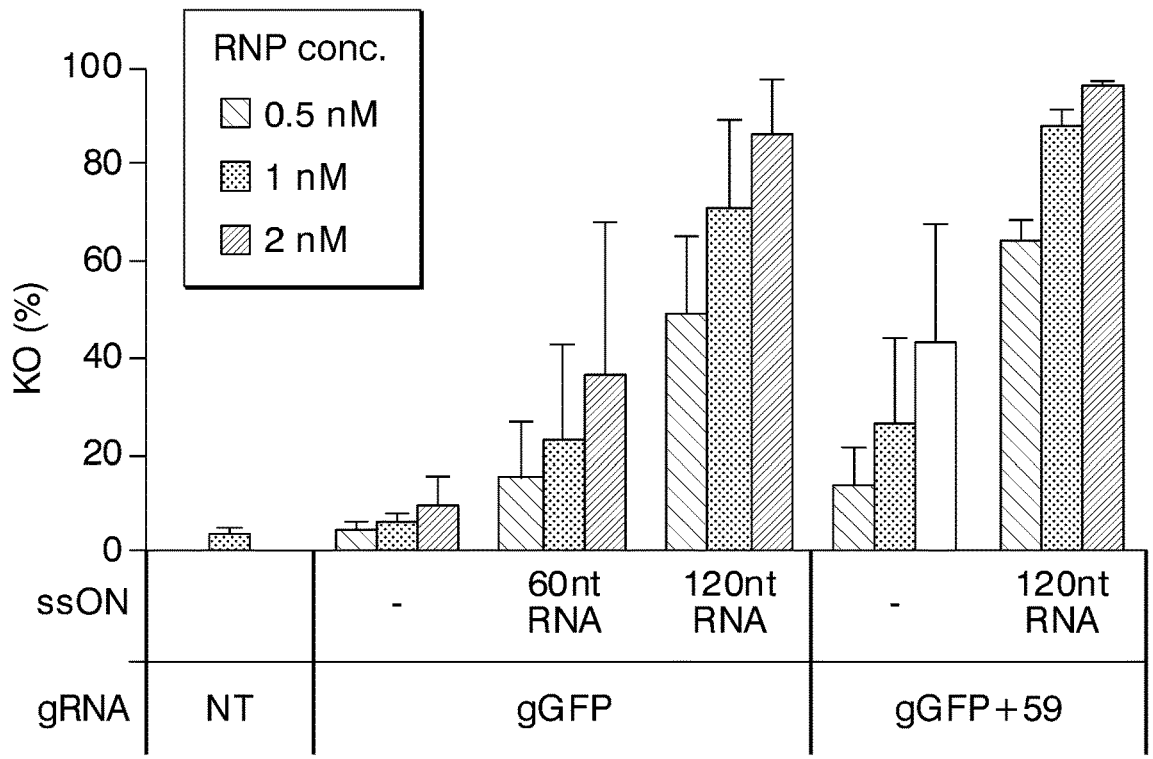
FIG. 17 is a drawing showing measurement results of the GFP knockout efficiency (%) in HeLa-GFP cells cultured in the medium in which the RNP-loaded lipid nanoparticle was added such that the concentration of Cpf1 protein was 0.5 nM, 1 nM or 2 nM in Example 5.

Measurement results of the GFP knockout efficiency are shown in FIG. 17. In the figure, the result of "NT" indicates the result of cells which were cultured in the culture medium to which the RNP-loaded lipid nanoparticles were not added. The results of "gGFP" indicate the results of cells which were cultured in the culture medium to which the RNP-loaded lipid nanoparticles using RNA having a 41-base length (SEQ. ID. NO. 8) were not added, and the results of "gGFP+59" indicate the results of cells which were cultured in the culture medium to which the RNP-loaded lipid nanoparticles using RNA having a 100-base length (SEQ. ID. NO. 9) were not added. In the column "ssON", the results of "-" indicate the results of cells which were cultured in the culture medium to which the RNP-loaded lipid nanoparticles free from ssON were not added. In addition, the results of "0.5 nM", "1 nM", or "2 nM" indicate the results of cells which were cultured in the culture medium to which the RNP-loaded lipid nanoparticles were added such that the concentration of the Cpf1 protein became 0.5 nM, 1 nM, or 2 nM, respectively.

The GFP knockout activity was improved by adding ssON to RNP in a similar manner to that of the case where the Cas9 protein was used, as shown in FIG. 17. In addition, the tendency was observed in which the longer the base length of the added ssON, the higher the knockout activity. It was apparent from the results that the lipid nanoparticle according to the present invention was useful as a carrier to introduce RNP not only in the CRISPR/Cas9 system but also in the CRISPR/Cpf1 system.

Example 6

A double nicking method in which two pairs of Cas9 nickase (Cas9n) in which either RuvC nuclease activity or HNH nuclease activity is inactivated are used is known as a method of decreasing off-target effects (introduction of mutation in untargeted gRNA region). Lipid nanoparticles loaded with RNP used in the double nicking method were prepared and then the gene knockout activity thereof was investigated.

The RNP-loaded lipid nanoparticles B-9 were prepared in a similar manner to that of Example 2, except that Cas9n protein (product name: "Alt-R S.p. Cas9 D10A Nickase V3", manufactured by Integrated DNA technologies) was used instead of the Cas9 protein, tracrRNA used in Reference Example 1, crRNA (SEQ. ID. NO. 12, 36-base length) including a base sequence complementary to the first target sequence in the GFP gene, and crRNA (SEQ. ID. NO. 13, 36-base length) including a base sequence complementary to the second target sequence were used as gRNA, and ssON was not used. The RNP-loaded lipid nanoparticles B-9 on which RNP including the Cas9 protein was loaded were prepared as a reference control in a similar manner to that of Example 2.

Then, the RNP-loaded lipid nanoparticles were added to the culture medium of HeLa-GFP cells seeded the day before such that the concentration of the Cas9n protein or the Cas9 protein became 0.1 nM, 0.3 nM, 1 nM, or 2 nM, and then cultured. After two days had passed from addition of the RNP-loaded lipid nanoparticles, the culture medium was replaced, and then the cells were further cultured for additional three days, followed by collecting the cells to measure the GFP knockout efficiency (%) (the ratio (%) of cells which did not express GFP fluorescence to entire cells) by flow cytometry.

Figure 18:
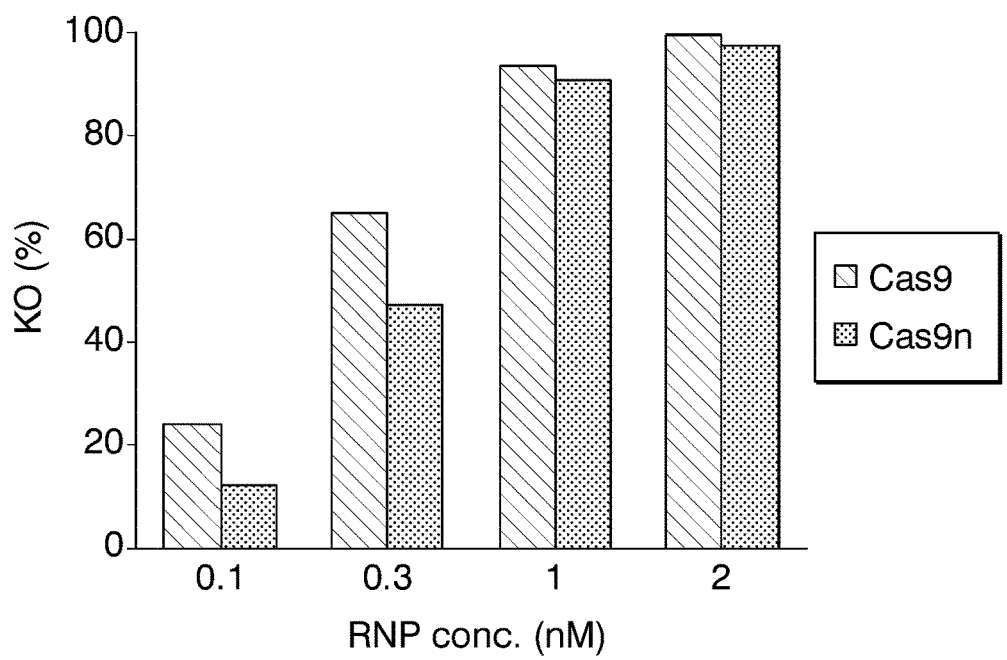
FIG. 18 is a drawing showing measurement results of the GFP knockout efficiency (%) in HeLa-GFP cells cultured in the medium in which the RNP-loaded lipid nanoparticle containing Cas9n protein or the RNP-loaded lipid nanoparticle containing Cas9 protein was added such that the concentration of Cas9n protein or the like was 0.1 nM, 0.3 nM, 1 nM or 2 nM in Example 6.

Measurement results are shown in FIG. 18. The RNP-loaded lipid nanoparticles on which the Cas9n protein was loaded exhibited a high GFP knockout activity in a similar manner to the RNP-loaded lipid nanoparticles on which the Cas9 protein was loaded. Particularly, 98% of the GFP knockout efficiency was confirmed in the cells to which the addition was conducted such that the concentration of the Cas9n protein became 2 nM. It was apparent from the results that the lipid nanoparticle having a particular lipid constitution according to the present invention was useful as a carrier to introduce RNP in the double nicking method in which the Cas9n protein was used, and it was suggested that RNP in which ssONs hybridizable with the respective gRNA were further included in the RNP used in the double nicking method was also useful as a carrier to introduce RNP in the double nicking method.

Example 7

Figure 19A:
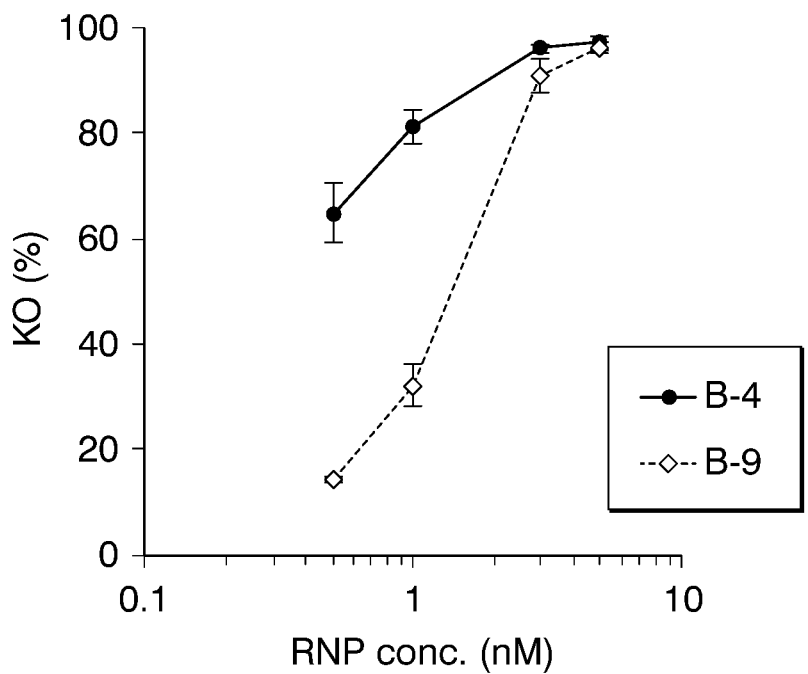
FIG. 19A is a drawing showing measurement results of the GFP knockout efficiency (%) in HEK-GFP cells cultured in the medium in which the RNP-loaded lipid nanoparticle B-4 or B-9 was added such that the concentration of Cas9 protein was 0.5 nM, 1 nM, 3 nM or 5 nM in Example 7.
Figure 19B:
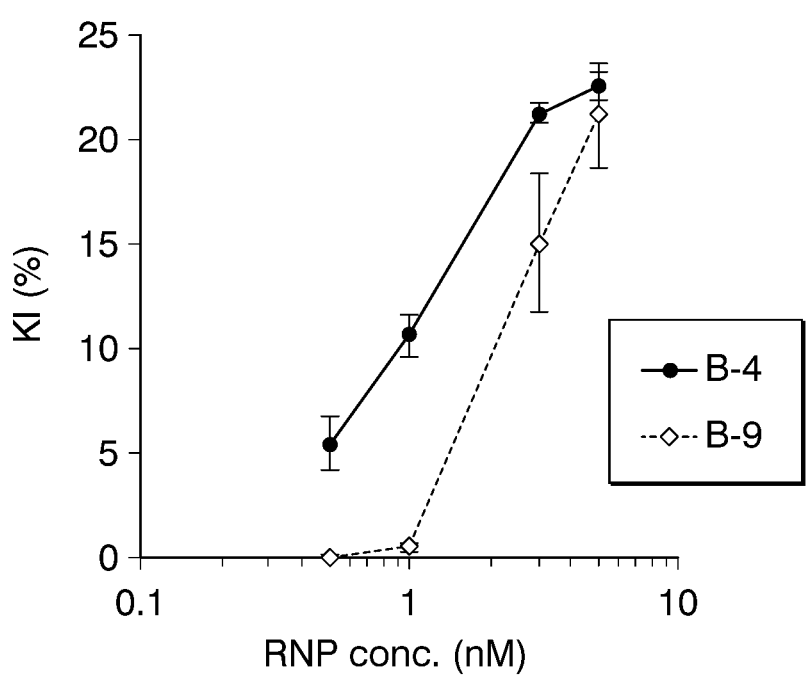
FIG. 19B is a drawing showing measurement results of the ratio (%) of the BFP positive cells in HEK-GFP cells cultured in the medium in which the RNP-loaded lipid nanoparticle B-4 or B-9 was added such that the concentration of Cas9 protein was 0.5 nM, 1 nM, 3 nM or 5 nM in Example 7.
Figure 20:
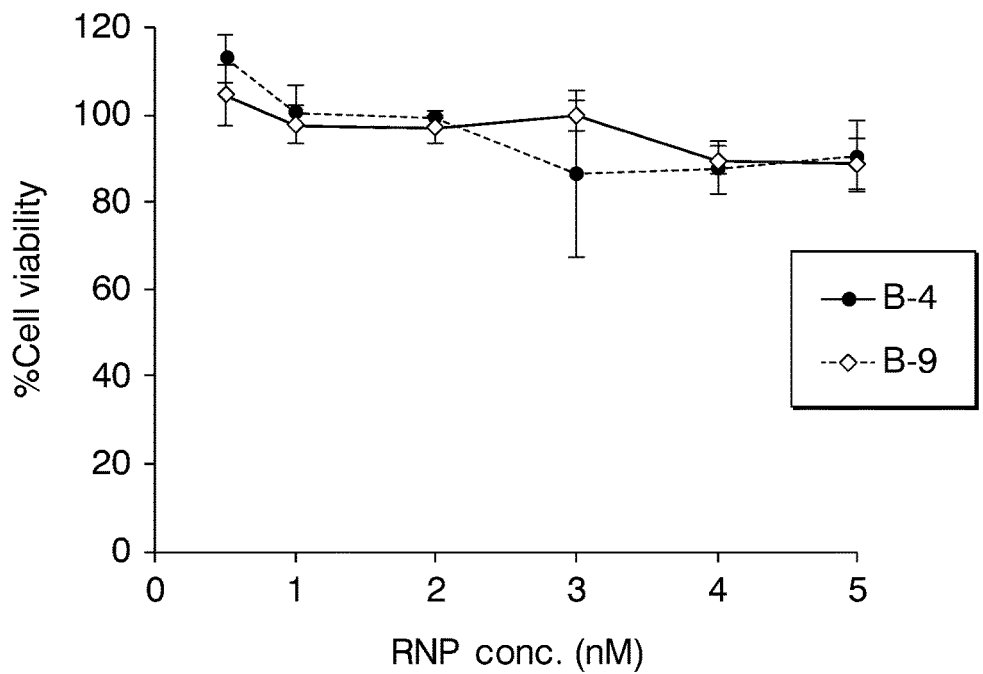
FIG. 20 is a drawing showing measurement results of the cell viability (%) of cells to which the RNP-loaded lipid nanoparticle B-4 or B-9 was added in Example 7.

The RNP-loaded lipid nanoparticles B-4 and B-9 prepared in Example 2 were introduced into GFP-stably-expressing HEK (HEK-GFP) cells to investigate the knockout activity, the knockin activity, and the cytotoxicity.
<Measurement of GFP Knockout Activity>
The RNP-loaded lipid nanoparticles B-9 and B-4 including ssON available to conduct knockout of GFP were prepared in the same way as that of Example 2. Then, the RNP-loaded lipid nanoparticles were added to the culture medium of HEK-GFP cells seeded the day before such that the concentration of the Cas9 protein became 0.5 nM, 1 nM, 3 nM, or 5 nM, and then cultured. After three days had passed from addition of the RNP-loaded lipid nanoparticles, the culture medium was replaced, and then the cells were further cultured for additional three days, followed by collecting the cells to measure the knockout efficiency (%) (the ratio (%) of cells which did not express GFP fluorescence to entire cells) by flow cytometry. Measurement results are shown in FIG. 19A. Both the cells in which RNP-loaded lipid nanoparticles B-9 were introduced and the cells in which RNP-loaded lipid nanoparticles B-4 were introduced exhibited approximately 97% of the knockout efficiency at the maximum.
<Measurement of GFP Knockin Activity>
The RNP-loaded lipid nanoparticles B-9 and B-4 were prepared in a similar manner to that of Example 2, except that ssON used to conduct knockin of GFP in Example 1 was used instead of the ssON available to conduct knockout of GFP. Then, the RNP-loaded lipid nanoparticles were introduced into the HEK-GFP cells and then cultured in a similar manner to that conducted to measure the GFP knockout activity as mentioned above, followed by collecting the cells to measure the knockin efficiency (%) (the ratio (%) of cells which expressed BFP fluorescence to entire cells) by flow cytometry. Measurement results are shown in FIG. 19B. Both the cells in which the RNP-loaded lipid nanoparticles B-9 were introduced and the cells in which the RNP-loaded lipid nanoparticles B-4 were introduced exhibited approximately 23% of the knockin efficiency at the maximum.
<Cytotoxicity>
The RNP-loaded lipid nanoparticles were added to the culture medium of HEK-GFP cells seeded the day before such that the concentration of the Cas9 protein became 0.5 nM, 1 nM, 2 nM, 3 nM, 4 nM, or 5 nM, and then cultured. After one day had passed from addition of the RNP-loaded lipid nanoparticles, the WST-8 assay was conducted in a similar manner to that of Example 3 to measure the cell viability (%). Results are shown in FIG. 20. The cell viability of the cells in which the RNP-loaded lipid nanoparticles B-4 or B-9 were introduced was almost 100%. In other words, the RNP-loaded lipid nanoparticles did not exhibit significant cytotoxicity in the HEK cells in a similar manner to the HeLa cells.

Example 8

The RNP-loaded lipid nanoparticles B-9 prepared in Example 2 were introduced in bone-marrow-derived macrophages (BMDMs) which constantly express GFP to measure the GFP knockout activity.
<BMDMs Constantly Expressing GFP>
The BMDMs constantly expressing GFP were collected from GFP-constantly-expressing-mice (C57BL/6-Tg (CAG-EGFP) mice) (female, aged 6 seeks). Specifically, bone marrow cells were collected from the femur and tibia of GFP-constantly expressing mice, passed through a 40 μm cell strainer, and red blood cells were removed therefrom using a solubilizing buffer (product name: ACK lysing buffer, manufactured by GIBCO BRL). Then, the bone marrow cells were cultured in the culture medium containing recombinant mouse M-CSF (final concentration: 50 ng/mL, manufactured by BioLegend, Inc.) and inactivated FBS (final concentration: 10%) for seven days to obtain the BMDMs.
<Measurement of GFP Knockout Activity>
The RNP-loaded lipid nanoparticles B-9 containing ssON available to conduct knockout of GFP were prepared in a similar manner to that of Example 2. Then, the RNP-loaded lipid nanoparticles were added to the culture medium in which the BMDMs were cultured such that the concentration of the Cas9 protein became 8 nM, and then cultured. After one day had passed from the addition of the RNP-loaded lipid nanoparticles, the culture medium was replaced, and the cells were collected after two days to be subjected to flow cytometry.

Figure 21:
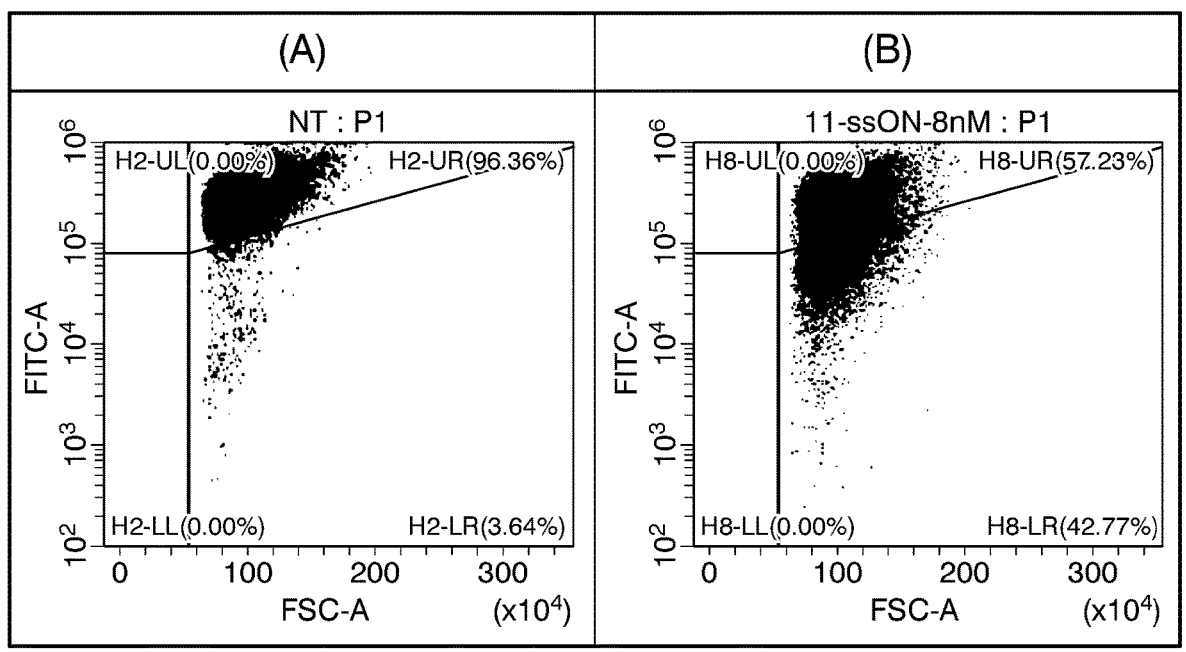
FIG. 21 is a drawing showing the result (A) of flow cytometry of BMDMs constantly expressing GFP before introducing the RNP-loaded lipid nanoparticle, and the result (B) of flow cytometry of BMDMs constantly expressing GFP after introducing the RNP-loaded lipid nanoparticle in Example 8.

Results of the flow cytometry of the BMDMs before introducing the RNP-loaded lipid nanoparticles therein are shown in FIG. 21(A), and results of the flow cytometry of the BMDMs after introducing the RNP-loaded lipid nanoparticles therein are shown in FIG. 21(B). Although almost all of the BMDMs before introducing the RNP-loaded lipid nanoparticles expressed GFP fluorescence, the ratio of the BMDMs which did not express GFP fluorescence after introducing the RNP-loaded lipid nanoparticles therein was increased. It was apparent from the results that the lipid nanoparticle according to the present invention was useful as a carrier to introduce RNP used in genome editing or the like in cells collected from living organisms.

Example 9

RNP-loaded lipid nanoparticles were prepared using a device in which the mixer-embedded micro flow channel 104 of the manufacturing device shown in FIG. 2 used in Reference Example 1 and the like was replaced with a flow channel 107 having three introducing passages as shown in FIG. 1B, and the physical property and the GFP knockout activity thereof were investigated.

<Preparation of RNP-Loaded Lipid Nanoparticles B-9>

The RNP-loaded lipid nanoparticles B-9 were prepared in a similar manner to that of Example 2, except that, in a similar manner to that shown in FIG. 1B, an ethanol solution of lipid was introduced from the first introducing passage (an introducing passage on the upper side of the figure), an RNP solution was introduced from the second introducing passage (an introducing passage on the lower side of the figure), and PBS(−) was introduced from the third introducing passage (an introducing passage in the center of the figure), at each FRR (flow rate: [flow rate (x) of the ethanol solution of lipid]/[flow rate (y) of PBS(−)]/[flow rate (z) of the RNP solution) as shown in Table 17. In the case where the FRR satisfied x/y/z=9/0/1 as shown in Table 16, the manufacturing device having two introducing passages, which was used in Reference Example 1, was used to prepare the particles.

The number-weighted average particle size (nm) of the resultant RNP-loaded lipid nanoparticles, the PdI thereof, and the encapsulation ratio (%) of gRAN and ssON in lipid nanoparticles were measured in the same way as that of Example 1. Measurement results are shown in Table 17. As a result, the RNP-loaded lipid nanoparticles had physical properties equal to or greater than those of the RNP-loaded lipid nanoparticles obtained in Example 2 using the manufacturing device having two introducing passages, even in the case where the manufacturing device having three introducing passages was used.

TABLE 17

| FRR (x/y/z) | Number-weighted average particle size (nm) | PdI | Encapsulation ratio (%) |
| --- | --- | --- | --- |
| 9/0/1 | 147.4 | 0.213 | 95.0 |
| 8/1/1 | 130.5 | 0.121 | 94.8 |
| 7/2/1 | 115.8 | 0.134 | 95.2 |
| 6/3/1 | 115.2 | 0.128 | 93.6 |
| 5/4/1 | 131.1 | 0.117 | 94.6 |

When the manufacturing device was checked after manufacturing, aggregates were formed at the interface between the ethanol solution of lipid and the RNP solution in the vicinity of the inlet of the dilution flow channel, in the case where the manufacturing device having two introducing passages, which was used in Reference Example 1, was used. In contrast, no aggregates were formed in the dilution flow channel, in the case where a manufacturing device having three introducing passages was used to introduce PBS from an introducing passage at the center thereof.

Figure 22:
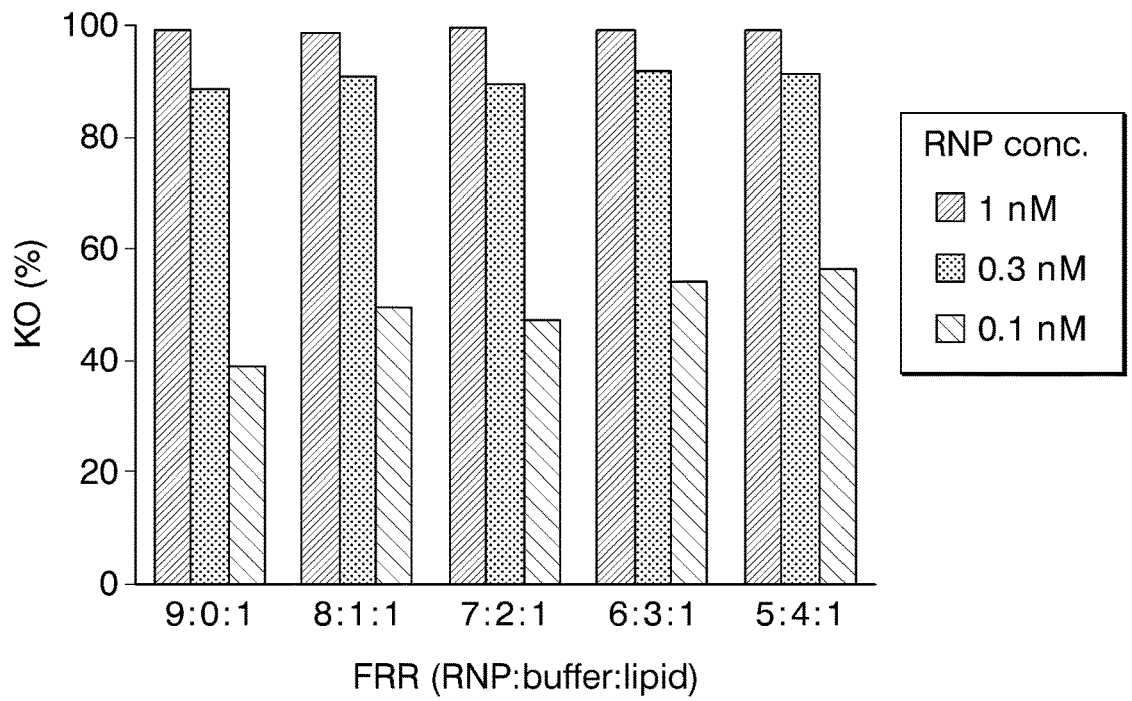
FIG. 22 is a drawing showing measurement results of the GFP knockout efficiency (%) in HeLa-GFP cells cultured in the medium in which the RNP-loaded lipid nanoparticle B-9 was added such that the concentration of Cas9 protein was 0.1 nM, 0.3 nM, or 1 nM, in Example 9.

The resultant RNP-loaded lipid nanoparticles were added to the culture medium in the same way as that of Example 4, such that the concentration of the Cas9 protein became 0.1 nM, 0.3 nM, or 1 nM, to allow the introduction thereof in the HeLa-GFP cells, and the GFP knockout activity thereof was investigated. Results are shown in FIG. 22. All RNP-loaded lipid nanoparticles had GFP knockout activity equal to or higher than the RNP-loaded lipid nanoparticles obtained in Example 2.

It was confirmed from the results that the use of the mixer-embedded micro flow channel having three introducing passages as shown in FIG. 1B made it possible to stably prepare RNP-loaded lipid nanoparticles having sufficient physical properties and gene knockout activity while avoiding the formation of aggregates in the mixer-embedded micro flow channel.

Example 10

Effects of the pH of the RNP solution when the RNP-loaded lipid nanoparticles were prepared on the knockout activity of the resultant RNP-loaded lipid nanoparticles were investigated.

The RNP-loaded lipid nanoparticles containing Cas9 protein were prepared in a similar manner to that of the RNP-loaded lipid nanoparticles B-9 prepared in Example 2, except that MES buffer (20 mM MES, 50 mM NaCl, pH 6.0 or 6.3) as a buffer having a pH of 6.0 or 6.3, or citrate buffer (20 mM citric acid, 50 mM NaCl, pH 4.0, 5.0, or 5.5) as a buffer having a pH of 4.0, 5.0, or 5.5 was used as the buffer to prepare an RNP solution. In addition, the RNP-loaded lipid nanoparticles containing Cpf1 protein were similarly prepared except that the Cpf1 protein used in Example 5 was used instead of the Cas9 protein.

Figure 23A:
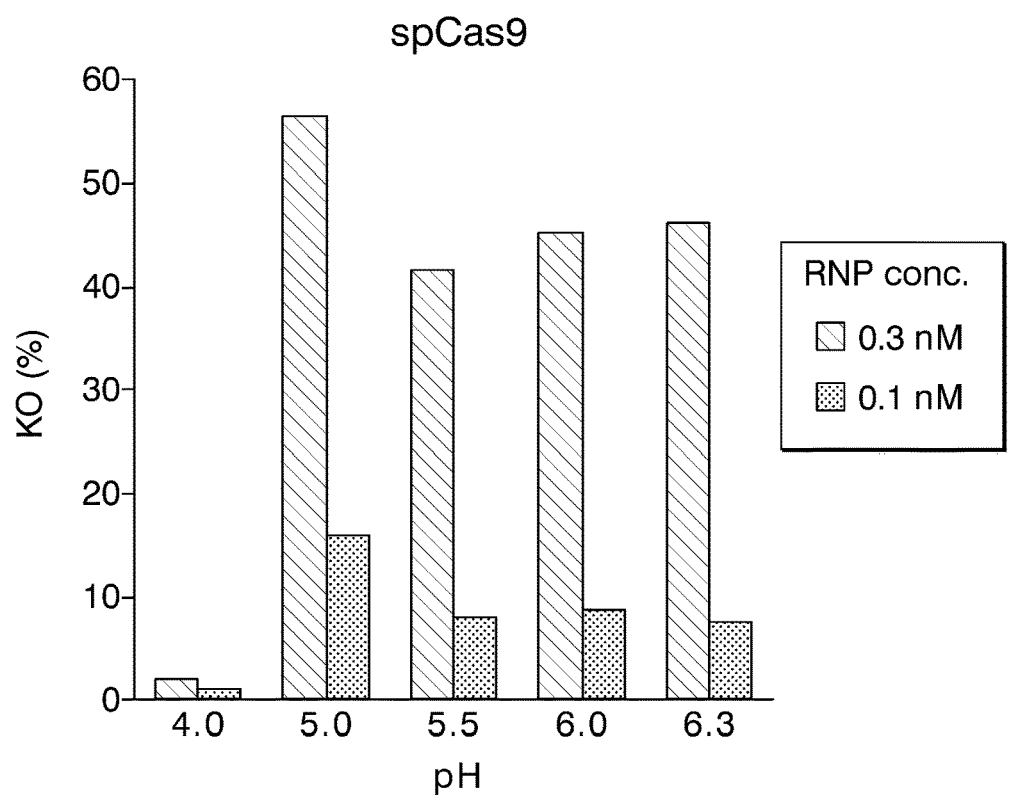
FIG. 23A is a drawing showing measurement results of the GFP knockout efficiency (%) in HeLa-GFP cells cultured in the medium in which the RNP-loaded lipid nanoparticle containing Cas9 protein was added in Example 10.
Figure 23B:
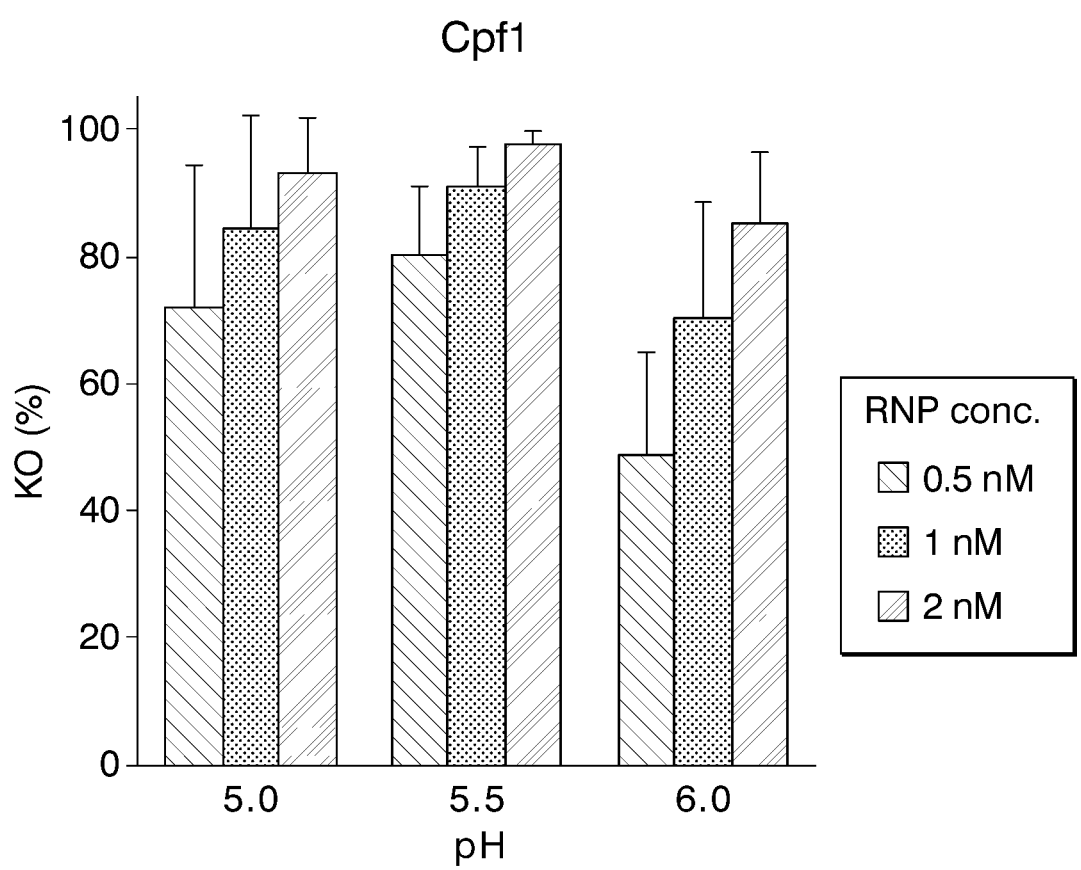
FIG. 23B is a drawing showing measurement results of the GFP knockout efficiency (%) in HeLa-GFP cells cultured in the medium in which the RNP-loaded lipid nanoparticle containing Cpf1 protein was added in Example 10.

Then, the RNP-loaded lipid nanoparticles were added to the culture medium of HeLa-GFP cells seeded the day before such that the concentration of the Cas9 protein became 0.1 nM or 0.3 nM, or the concentration of the Cpf1 protein became 0.5 nM, 1.0 nM, or 2.0 nM, and then cultured. After two days had passed from addition of the RNP-loaded lipid nanoparticles, the culture medium was replaced, and then the cells were further cultured for additional three days, followed by collecting the cells to measure the knockout efficiency (%) (the ratio (%) of cells which did not express GFP fluorescence to entire cells) by flow cytometry. Results of cells in which the RNP-loaded lipid nanoparticles including the Cas9 protein were introduced are shown in FIG. 23A, and results of cells in which the RNP-loaded lipid nanoparticles including the Cpf1 protein were introduced are shown in FIG. 23B.

As a result, the RNP-loaded lipid nanoparticles containing any of the Cas9 protein and the Cpf1 protein maintained gene knockout activity, in the case where the pH at the time of preparation was 5.0 or more.

EXPLANATION OF REFERENCE NUMERALS

10 First introducing passage
20 Second introducing passage
30 Dilution flow channel
31 Confluence
40 Structural element
50 Bent-flow channel portion
60 Third introducing passage
101, 102 Syringe
103 Flow quantity control device
104 Mixer-embedded micro flow channel
104a Inlet of first introducing passage
104b Inlet of second introducing passage
104c Dilution flow channel
104d Outlet of dilution flow channel
105 Tube
106 Collection container
107 Chaotic mixer-embedded micro flow channel
107a Inlet of first introducing passage
107b Inlet of second introducing passage
107c Dilution flow channel
107d Outlet of dilution flow channel

The invention claimed is:

1. A lipid nanoparticle comprising: lipid components; a DNA nuclease; a guide RNA; and a single-stranded oligonucleotide, wherein the lipid components comprise: a pH-sensitive cationic lipid of general formula (I):

$$(R^1)(R^2)C(OH)-(CH_2)a-(O-CO)b-X \quad (I)$$

wherein the formula (I), a is an integer of 3 to 5; b is 0 or 1; $R^1$ and $R^2$ are each independently a group of general formula (A):

$$CH_3-(CH_2)q-(CH=CH)r-(CH_2)s-(CH=CH)t-(CH_2)u-(CO-O)c-(CH_2)v- \quad (A)$$

wherein in the formula (A), q is an integer of 1 to 9; r is 0 or 1; s is an integer of 1 to 3; t is 0 or 1; u is an integer of 1 to 8; c is 0 or 1; v is an integer of 4 to 12; and q+2r+s+2t+u+c+v is an integer of 19 or more, but groups in which both b and c are 0, q is an integer of 3 to 5, both r and t are 1, s is 1, and u+v is an integer of 6 to 10 are excluded; and wherein X is a group of general formula (B):

$$-(CH_2)d-N(R^3)(R^4) \quad (B)$$

wherein in the formula (B), d is an integer of 0 to 3; $R^3$ and $R^4$ are each independently a $C_{1-4}$ alkyl group or a $C_{2-4}$ alkenyl group, wherein 1 or 2 hydrogen atoms of the $C_{1-4}$ alkyl group or the $C_{2-4}$ alkenyl group may be substituted with a phenyl group, $R^3$ and $R^4$ may be bonded together to form a 5-membered to 7-membered non-aromatic hetero ring, wherein 1 or 2 hydrogen atoms of the ring may be substituted with a $C_{1-4}$ alkyl group or a $C_{2-4}$ alkenyl group, or a 5-membered to 7-membered non-aromatic hetero ring group, wherein a carbon atom of the group is bonded to (O-CO)b-, and 1 or 2 hydrogen atoms of the ring may be substituted with a $C_{1-4}$ alkyl group or a $C_{2-4}$ alkenyl group;

a neutral phospholipid; and a polyalkylene glycol-modified lipid, wherein a ratio of the pH-sensitive cationic lipid relative to a total amount of lipids constituting the lipid nanoparticle is 30% by mol to 50% by mol, wherein a ratio of the neutral phospholipid relative to the total amount of lipids constituting the lipid nanoparticle is 20% by mol to 50% by mol, wherein a ratio of the polyalkylene glycol-modified lipid relative to the total amount of lipids constituting the lipid nanoparticle is 1% by mol to 4% by mol, and wherein the single-stranded oligonucleotide comprises a region which hybridizes with the guide RNA constituting a complex with the DNA nuclease.

2. The lipid nanoparticle according to claim 1, wherein the neutral phospholipid is a neutral glycerophospholipid having a C12-24 saturated or unsaturated fatty-acid residue.

3. The lipid nanoparticle according to claim 1, wherein the neutral phospholipid is a phosphatidylethanolamine having a C12-24 unsaturated fatty-acid residue.

4. The lipid nanoparticle according to claim 1, wherein the pH-sensitive cationic lipid is a polyethylene glycol-modified lipid.

5. The lipid nanoparticle according to claim 1, wherein the DNA nuclease is a Cas9 protein, and
the guide RNA comprises a crRNA and a tracrRNA.

6. The lipid nanoparticle according to claim 5, wherein the Cas9 protein is a protein having either RuvC nuclease activity or HNH nuclease activity.

7. The lipid nanoparticle according to claim 1, wherein the DNA nuclease is a Cpf1 protein.

8. A genome editing method comprising introducing a lipid nanoparticle of claim 1 into cells.

9. A preparation method of a lipid nanoparticle of claim 1, comprising using a flow channel structure, wherein
the flow channel structure comprises a first introducing passage configured to introduce a first fluid and a second introducing passage configured to introduce a second fluid, which are mutually independent and join together while each having fixed lengths to form a single dilution flow channel,
the dilution flow channel comprises a two-dimensionally bent-flow channel portion in at least a portion thereof,
the bent-flow channel portion is configured such that an axial direction of the dilution flow channel upstream therefrom or an extending direction thereof is defined as an X direction, a width direction of the dilution flow channel that perpendicularly intersects with the X direction is defined as a Y direction, and the flow channel width of the dilution flow channel upstream therefrom is defined as $y_0$, and at least two structural elements which define flow channel widths of the dilution flow channel by alternately protruding from two side surfaces, facing each other in the Y direction, of the dilution flow channel towards a center of the flow channel at a fixed height $h_1, h_2, \ldots$ of $\frac{1}{2}y_0$ or more and less than $1_{y0}$ in an approximate Y direction (approximate +Y direction or approximate −Y direction) and at a fixed width $X_1, X_2, \ldots$ in the X direction are provided at fixed intervals $d_1, d_2, \ldots$, and
a lipid solution in which lipid components are dissolved in ethanol and which is introduced from the first introducing passage; and an aqueous solution which contains a DNA nuclease, a guide RNA and a single-stranded oligonucleotide, and which is introduced from the second introducing passage, and which has a pH of at least 5.0, have a total flow rate of 1 µL/minute to 100 mL/minute, and a ratio of a flow rate of the lipid solution to a flow rate of the aqueous solution of at least 7.

10. The preparation method of the lipid nanoparticle according to claim 9, wherein the flow channel structure further comprises a third introducing passage configured to introduce a third fluid, and
the first introducing passage, the second introducing passage, and the third introducing passage join together while each having fixed lengths to form a single dilution flow channel such that the first fluid introduced from the first introducing passage contacts with the third fluid introduced from the third introducing passage before joining the second fluid introduced from the second introducing passage.

* * * * *

SEQUENCE LISTING

<160> NUMBER OF SEQ ID NOS: 13

<210> SEQ ID NO 1
<211> LENGTH: 20
<212> TYPE: DNA
<213> ORGANISM: Aequorea coerulescens
<220> FEATURE:
<223> OTHER INFORMATION: partial of GFP gene

<400> SEQUENCE: 1
acggcgtgca gtgcttcagc                                               20

<210> SEQ ID NO 2
<211> LENGTH: 36
<212> TYPE: RNA
<213> ORGANISM: Artificial Sequence
<220> FEATURE:
<223> OTHER INFORMATION: Description of Artificial Sequence: Synthesized
      crRNA

<400> SEQUENCE: 2
gcugaagcac ugcacgccgu guuuuagagc uaugcu                              36

<210> SEQ ID NO 3
<211> LENGTH: 67
<212> TYPE: RNA
<213> ORGANISM: Artificial Sequence
<220> FEATURE:
<223> OTHER INFORMATION: Description of Artificial Sequence: Synthesized
      tracrRNA

<400> SEQUENCE: 3
agcauagcaa guuaaaauaa ggcuaguccg uuaucaacuu gaaaaagugg caccgagucg    60
gugcuuu                                                              67

<210> SEQ ID NO 4
<211> LENGTH: 617
<212> TYPE: DNA
<213> ORGANISM: Artificial Sequence
<220> FEATURE:
<223> OTHER INFORMATION: Description of Artificial Sequence: Synthesized
      dsDNA

<400> SEQUENCE: 4
tgcccatcct ggtcgagctg gacggcgacg taaacggcca caagttcagc gtgtccggcg    60
agggcgaggg cgatgccacc tacggcaagc tgaccctgaa gttcatctgc accaccggca   120
agctgcccgt gccctggccc accctcgtga ccaccctgac ctacggcgtg cagtgcttca   180
gccgctaccc cgaccacatg aagcagcacg acttcttcaa gtccgccatg cccgaaggct   240
acgtccagga gcgcaccatc ttcttcaagg acgacggcaa ctacaagacc cgcgccgagg   300
tgaagttcga gggcgacacc ctggtgaacc gcatcgagct gaagggcatc gacttcaagg   360
aggacggcaa catcctgggg cacaagctgg agtacaacta caacagccac aacgtctata   420
tcatggccga caagcagaag aacggcatca aggtgaactt caagatccgc cacaacatcg   480
aggacggcag cgtgcagctc gccgaccact accagcagaa cacccccatc ggcgacggcc   540
ccgtgctgct gcccgacaac cactacctga gcacccagtc cgccctgagc aaagacccca   600
acgagaagcg cgatcac                                                  617

<210> SEQ ID NO 5
<211> LENGTH: 132
<212> TYPE: DNA

```
<213> ORGANISM: Artificial Sequence
<220> FEATURE:
<223> OTHER INFORMATION: Description of Artificial Sequence: Synthesized
      ssODN for GFP knock out

<400> SEQUENCE: 5
ctgaagttca tctgcaccac cggcaagctg cccgtgccct ggcccaccct cgtgaccacc       60
ctgacctacg gcgtgcagtg cttcagccgc taccccgacc acatgaagca gcacgacttc      120
ttcaagtccg cc                                                          132

<210> SEQ ID NO 6
<211> LENGTH: 132
<212> TYPE: DNA
<213> ORGANISM: Artificial Sequence
<220> FEATURE:
<223> OTHER INFORMATION: Description of Artificial Sequence: Synthesized
      ssODN for BFP knock in

<400> SEQUENCE: 6
ctgaagttca tctgcaccac cggcaagctg cccgtgccct ggcccaccct cgtgaccacc       60
ctgagccacg gggtgcagtg cttcagccgc taccccgacc acatgaagca gcacgacttc      120
ttcaagtccg cc                                                          132

<210> SEQ ID NO 7
<211> LENGTH: 60
<212> TYPE: RNA
<213> ORGANISM: Artificial Sequence
<220> FEATURE:
<223> OTHER INFORMATION: Description of Artificial Sequence: Synthesized
      ssODN for GFP knock out

<400> SEQUENCE: 7
ccucgugacc acccugaccu acggcgugca gugcuucagc cgcuaccccg accacaugaa       60

<210> SEQ ID NO 8
<211> LENGTH: 41
<212> TYPE: RNA
<213> ORGANISM: Artificial Sequence
<220> FEATURE:
<223> OTHER INFORMATION: Description of Artificial Sequence: Synthesized
      gRNA

<400> SEQUENCE: 8
uaauuucuac ucuuguagau cgucgccguc cagcucgacc a                          41

<210> SEQ ID NO 9
<211> LENGTH: 100
<212> TYPE: RNA
<213> ORGANISM: Artificial Sequence
<220> FEATURE:
<223> OTHER INFORMATION: Description of Artificial Sequence: Synthesized
      gRNA

<400> SEQUENCE: 9
cgaucgcucg guuaggagag accccagacg cuccggccau acgcgagucc accaugaauu       60
aauuucuacu cuuguagauc gucgccgucc agcucgacca                            100

<210> SEQ ID NO 10
<211> LENGTH: 120
<212> TYPE: RNA
<213> ORGANISM: Artificial Sequence
<220> FEATURE:
<223> OTHER INFORMATION: Description of Artificial Sequence: Synthesized
      ssODN
```

```
<400> SEQUENCE: 10
auggugagca agggcgagga gcuguucacc gggguggugc ccauccuggu cgagcuggac      60
ggcgacguaa acggccacaa guucagcgug uccggcgagg gcgagggcga gggcgaugcc     120

<210> SEQ ID NO 11
<211> LENGTH: 60
<212> TYPE: RNA
<213> ORGANISM: Artificial Sequence
<220> FEATURE:
<223> OTHER INFORMATION: Description of Artificial Sequence: Synthesized
      ssODN

<400> SEQUENCE: 11
caccggggug gugcccaucc uggucgagcu ggacggcgac guaaacggcc acaaguucag      60

<210> SEQ ID NO 12
<211> LENGTH: 36
<212> TYPE: RNA
<213> ORGANISM: Artificial Sequence
<220> FEATURE:
<223> OTHER INFORMATION: Description of Artificial Sequence: Synthesized
      crRNA

<400> SEQUENCE: 12
gggcacgggc agcuugccgg guuuuagagc uaugcu                                36

<210> SEQ ID NO 13
<211> LENGTH: 36
<212> TYPE: RNA
<213> ORGANISM: Artificial Sequence
<220> FEATURE:
<223> OTHER INFORMATION: Description of Artificial Sequence: Synthesized
      crRNA

<400> SEQUENCE: 13
cucgugacca cccugaccua guuuuagagc uaugcu                                36
```